US010928389B2

(12) United States Patent
Fan et al.

(10) Patent No.: US 10,928,389 B2
(45) Date of Patent: Feb. 23, 2021

(54) ARRAYS, SUBSTRATES, DEVICES, METHODS AND SYSTEMS FOR DETECTING TARGET MOLECULES

(71) Applicant: CALIFORNIA INSTITUTE OF TECHNOLOGY, Pasadena, CA (US)

(72) Inventors: Rong Fan, Pasadena, CA (US); Habib Ahmad, Los Angeles, CA (US); James R. Heath, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/359,464

(22) Filed: Nov. 22, 2016

(65) Prior Publication Data

US 2017/0138942 A1   May 18, 2017

Related U.S. Application Data

(63) Continuation of application No. 14/694,340, filed on Apr. 23, 2015, now abandoned, which is a continuation of application No. 12/174,601, filed on Jul. 16, 2008, now abandoned.

(60) Provisional application No. 60/998,981, filed on Oct. 15, 2007, provisional application No. 60/959,666, filed on Jul. 16, 2007.

(51) Int. Cl.
| | |
|---|---|
| *G01N 33/543* | (2006.01) |
| *B01L 3/00* | (2006.01) |
| *B01J 19/00* | (2006.01) |
| *G01N 33/58* | (2006.01) |

(52) U.S. Cl.
CPC .... *G01N 33/54393* (2013.01); *B01J 19/0046* (2013.01); *B01L 3/502746* (2013.01); *B01L 3/502753* (2013.01); *G01N 33/54366* (2013.01); *G01N 33/582* (2013.01); *B01J 2219/0074* (2013.01); *B01J 2219/00547* (2013.01); *B01J 2219/00596* (2013.01); *B01J 2219/00605* (2013.01); *B01J 2219/00621* (2013.01); *B01J 2219/00722* (2013.01); *B01J 2219/00725* (2013.01); *B01L 3/5025* (2013.01); *B01L 3/502715* (2013.01); *B01L 2300/0636* (2013.01); *B01L 2300/0864* (2013.01); *B01L 2300/0867* (2013.01); *B01L 2400/0487* (2013.01); *B01L 2400/084* (2013.01); *G01N 2458/10* (2013.01)

(58) Field of Classification Search
None
See application file for complete search history.

(56) References Cited

U.S. PATENT DOCUMENTS

| | | | |
|---|---|---|---|
| 5,858,801 A * | 1/1999 | Brizzolara | G01N 33/54386 422/503 |
| 6,039,897 A | 3/2000 | Lochhead et al. | |
| 6,165,739 A | 12/2000 | Clatch | |
| 6,429,027 B1 | 8/2002 | Chee et al. | |
| 6,524,790 B1 | 2/2003 | Kopf et al. | |
| 6,699,665 B1 | 3/2004 | Kim et al. | |
| 6,924,153 B1 * | 8/2005 | Boehringer | G01N 33/558 422/420 |
| 8,105,845 B2 * | 1/2012 | Notcovich | B01L 3/5027 436/518 |
| 9,188,586 B2 | 11/2015 | Fan et al. | |
| 9,506,917 B2 | 11/2016 | Fan et al. | |
| 9,824,870 B1 * | 11/2017 | Straume | G01N 27/622 |
| 2001/0016320 A1 * | 8/2001 | He | C12N 15/1034 435/6.14 |
| 2002/0090649 A1 * | 7/2002 | Chan | B01J 19/0046 435/7.1 |
| 2002/0100714 A1 * | 8/2002 | Staats | B01L 3/5027 210/85 |
| 2002/0131974 A1 * | 9/2002 | Segal | A61K 39/385 424/184.1 |
| 2002/0146745 A1 | 10/2002 | Natan et al. | |
| 2003/0013091 A1 | 1/2003 | Dimitrov | |
| 2003/0082601 A1 | 5/2003 | Dill | |
| 2003/0096232 A1 | 5/2003 | Kris et al. | |
| 2003/0104486 A1 * | 6/2003 | Selvan | B01J 19/0046 506/3 |
| 2003/0127610 A1 * | 7/2003 | Gallagher | G01B 11/14 250/574 |
| 2003/0190608 A1 | 10/2003 | Blackburn | |
| 2003/0190689 A1 * | 10/2003 | Crosby | G01N 33/5041 435/7.23 |
| 2004/0092032 A1 * | 5/2004 | Winkler | B01J 19/0046 436/174 |
| 2004/0191124 A1 | 9/2004 | Noetzel et al. | |

(Continued)

FOREIGN PATENT DOCUMENTS

| | | |
|---|---|---|
| DE | 10127221 A1 | 11/2002 |
| EP | 1 816 476 A1 | 8/2007 |

(Continued)

OTHER PUBLICATIONS

Ivanova, "Polymer Microstructures Fabricated via Laser Ablation Used for Multianalyte Protein Microassay", Langmuir, 2002, 18, 9539-9546.*
Adler et al. (2005) "Detection of femtogram amounts of biogenic amines using self-assembled DNA-protein nanostructures," Nature Methods. 2(2):147-149.
Anderson et al. (2002) "The human plasma proteome: history, character, and diagnostic prospects," Mol. Cell. Proteomics. 1:845-867.

(Continued)

*Primary Examiner* — Ann Y Lam
(74) *Attorney, Agent, or Firm* — Lathrop GPM LLP

(57) ABSTRACT

Arrays and substrates comprising a material, in particular capture agents and/or detectable targets, attached to the substrates along substantially parallel lines forming a barcoded pattern and related methods and systems.

16 Claims, 31 Drawing Sheets

Specification includes a Sequence Listing.

(56) References Cited

U.S. PATENT DOCUMENTS

| | | | |
|---|---|---|---|
| 2004/0224321 A1 | 11/2004 | Nicolau et al. | |
| 2004/0265889 A1* | 12/2004 | Durham | G01N 33/5014 435/6.16 |
| 2005/0142033 A1* | 6/2005 | Glezer | B01L 3/5085 422/400 |
| 2006/0246475 A1* | 11/2006 | Peterson | C12Q 1/6827 435/6.18 |
| 2006/0263818 A1 | 11/2006 | Scherer | |
| 2006/0286549 A1* | 12/2006 | Sohn | G01N 15/1031 435/5 |
| 2007/0074972 A1 | 4/2007 | Nassef | |
| 2007/0122819 A1 | 5/2007 | Wu | |
| 2007/0202538 A1 | 8/2007 | Glezer et al. | |
| 2008/0200343 A1* | 8/2008 | Clemens | B01L 3/502715 506/9 |
| 2009/0017455 A1 | 1/2009 | Kwong | |
| 2009/0036324 A1* | 2/2009 | Fan | G01N 33/582 506/9 |
| 2009/0053732 A1 | 2/2009 | Vermesh et al. | |
| 2010/0009335 A1* | 1/2010 | Joseph | C12M 23/12 435/3 |
| 2017/0067887 A1 | 3/2017 | Fan et al. | |
| 2017/0138942 A1 | 5/2017 | Fan et al. | |

FOREIGN PATENT DOCUMENTS

| | | | |
|---|---|---|---|
| WO | 2003/048736 A2 | 6/2003 | |
| WO | 2005/007892 A1 | 1/2005 | |
| WO | 2005/081867 A2 | 9/2005 | |
| WO | 2005/090972 A1 | 9/2005 | |
| WO | 2006/117541 A1 | 11/2006 | |
| WO | 2007/014267 A2 | 2/2007 | |
| WO | WO 2007/035633 A2 | 3/2007 | |
| WO | 2008/016680 A1 | 2/2008 | |
| WO | 2009/012340 A2 | 1/2009 | |
| WO | 2009/012343 A2 | 1/2009 | |

OTHER PUBLICATIONS

Andrade et al. (1986) "Protein adsorption and materials biocompatibility: A tutorial review and suggested hypotheses," Advances in Polymer Science. 79:1-63.
Arenkov et al. (2000) "Protein microchips: use for immunoassays and enzymatic reactions," Anal. Biochem. 278:123-131.
Armstrong et al. (2000) "Suspension arrays for high throughput, multiplexed single nucleotide polymorphism genotyping," 40(2):102-108.
Ashton et al. (1973) "Smoking and carboxhemoglobin," Lancet. 2:857-858.
Bailey et al. (2007) "DNA-Encoded Antibody Libraries: A Unified Platform for Multiplexed Cell Sorting and Detection of Genes and Proteins," Journal of the American Chemical Society. 129:1959-1967.
BD Biosciences (2007) "Purified Mouse Anti-Human IL-2," Accessible on the Internet at URL: http://www.bdbiosciences.com/ptProduct.jsp?prodid=6725.
BD Pharmingen (2003) "Technical data sheet: Purified mouse anti-human IL-2 monoclonal antibody (ELISA capture)," BD Biosciences. Accessible on the Internet at URL: http://www.bdbiosciences.com/ds/pm/tds/555051.pdf.
Becker et al. (2005) "Direct readout of protein-protein interactions by mass spectrometry from protein-DNA microarrays," Angew. Chemie. Int. Ed. 44:7635-7639.
Bernard et al. (2001) "Micromosaic immunoassays," Analytical Chemistry. 73:8-12.
Betensky et al. (2002) "Influence of unrecognized molecular heterogeneity on randomized clinical trials," J. Clin. Oncol. 20:2495-2499.
Boozer et al. (2004) "DNA directed protein immobilization on mixed ssDNA/oligo(ethylene glycol) self-assembled monolayers for sensitive biosensors," Anal. Chem. 76:6967-6972.

Boozer et al. (2006) "DNA-Directed Protein Immobilization for Simultaneous Detection of Multiple Analytes by Surface Plasmon Resonance Biosensor," Analytical Chemistry. 78:1515-1519.
Breslauer et al. (2006) "Microfluidic-based systems biology," Mol. Biosyst. 2:97-112.
Bunimovich et al. (2006) "Quantitative Real-Time Measurements of DNA Hybridization with Alkylated Nonoxidized Silicon Nanowires in Electrolyte Solution," J. Am. Chem. Soc. 128:16323-16331.
Campbell et al. (2002) "A monomeric red fluorescent protein," Proc. Natl. Acad. Sci. USA. 99(12):7877-7882.
Cardoso et al. (1995) "AAn improved panning technique for the selection of CD34+ human bone marrow hematopoietic cells with high recovery of early progenitors," Exp. Hematol. 23:407-412.
Chen et al. (2002) "Discordant protein and mRNA expression in lung adenocarcinomas," Mol. Cell. Proteomics. 1:304-313.
Chen et al. (2004) "Plasma proteome of severe acute respiratory syndrome analyzed by two-dimensional gel electrophoresis and mass spectrometry," Proc. Natl. Acad. Sci. USA. 101:17039-17044.
Chen et al. (2005) "Marked Differences in Human Melanoma Antigen-Specific T Cell Responsiveness after Vaccination Using a Functional Microarray," PLoS Medicine. 2(10)1018-1030.
Chou et al. (2000) "Sorting biomolecules with microdevices," Electrophoresis. 21:81-90.
Coussens et al. (2002) "Inflammation and cancer," Nature. 420:860-867.
Crowley et al. (2005) "Isolation of plasma from whole blood using planar microfilters for lab-on-a-chip applications," Lab on a Chip. 5:922-929.
Dandy et al. (2007) "Array feature size influences nucleic acid surface capture in DNA microarrays," Proc Natl. Acad. Sci. USA. 104:8223-8228.
De Marzo et al. (2007) "Inflammation in prostate carcinogenesis," Nature Reviews Cancer. 7:256-269.
Degenaar et al. (2001) "A method for micrometer resolution patterning of primary culture neurons for SPM analysis," J. Biochem. 130:367-376.
Dehqanzada et al. (2005) "Assessing serum cytokine profiles in breast cancer patients receiving a HER2/neu vaccine using Luminex technology," Annals of Surgical Oncology. 12:S47-S48.
Delamarche et al. (1997) "Patterned delivery of immunoglobulins to surfaces using microfluidic networks," Science. 276:779-781.
Dirks et al. (2004) "Paradigms for computational nucleic acid design," Nucleic Acids Research. 32(4):1392-1403.
Engvall et al. (1972) "Enzyme-linked immunosorbent assay, Elisa. 3. Quantitation of specific antibodies by enzyme-labeled anti-immunoglobulin in antigen-coated tubes," J. Immunol. 109:129-135.
Erickson et al. (2003) "Modeling of DNA hybridization kinetics for spatially resolved biochips," Anal. Biochem. 317:186-200.
Fainerman et al. (1998) "Adsorption of surfactants and proteins at fluid interfaces," Colloids and Surfaces. 143:141-165.
Fuji et al. (2005) "Clinical-scale high-throughput human plasma proteome analysis: lung adenocarcinoma," Proteomics. 5:1150-1159.
Fung (1973) "Stochastic flow in capillary blood vessels," Microvasc. Res. 5:34-38.
Gorelik et al. (2005) "Multiplexed immunobead-based cytokine profiling for early detection of ovarian cancer," Cancer Epidemiol. Biomarkers Prev. 14:981-987.
Groves et al. (1995) "In vitro maturation of clonal CD4+CD8+ cell lines in response to TCR engagement," J. Immunol. 154:5011-5022.
Guan et al. (2004) "Recombinant protein-based enzyme-linked immunosorbent assay and immunochromatographic tests for detection of immunoglobulin G antibodies to severe acute respiratory syndrome (SARS) coronavirus in SARS patients," Clinical and Diagnostics Laboratory Immunology. 11(2)287-291.
Hainfeld et al. (2002) "Silver and Gold-Based Autometallography of Nanogold," Ch. 3 In; Gold and Silver Staining. CRC Press. Washington, DC. pp. 29-46.
Heath et al. (2007) "Nanotechnology and cancer," Annual Review of Medicine. 59:251-265.

(56) References Cited

OTHER PUBLICATIONS

Holland et al. (1991) "Detection of specific polymerase chain reaction product by utilizing the 5'—3' exonuclease activity of Thermus aquaticus DNA polymerase" Proc. Natl. Acad. Sci. USA. 88:7276-7280.
Hong et al. (2003) "Integrated nanoliter systems," Nature Biotechnology. 21:1179-1183.
Hong et al. (2004) "A nanoliter-scale nucleic acid processor with parallel architecture," Nature Biotechnology. 22 (4):435-439.
Hsieh et al. (2006) "Systematical evaluation of the effects of sample collection procedures on low-molecular-weight serum/plasma proteome profiling," Proteomics. 6:3189-3198.
Huang et al. (2001) "Detection of multiple proteins in an antibody-based protein microarray system," Journal of Immunological Methods. 255:1-13.
Huang et al. (2004) "Continuous particle separation through deterministic lateral displacement," Science. 304:987-990.
Huang et al. (2007) "Counting low-copy number proteins in a single cell," Science. 315:81-84.
Huber et al. (2004) "Comparison of proteomic and genomic analyses of the human breast cancer cell line T47D and the antiestrogen-resistant derivative 147D-r," Molec. Cell. Proteomics. 3:43-55.
Hughes et al. (2003) "Molecular Monitoring of Chronic Myeloid Leukemia," Seminars in Hematology. 40(2):62-68.
Iannone et al. (1999) "Multiplexed single nucleotide polymorphism genotyping by oligonucleotide ligation and flow cytometry," Cytometry. 39(2):131-140.
Thirumalapura et al. (2005) "Lipopolysaccharide microarrays for the detection of antibodies," Journal of Immunological Methods. 298:73-81.
Thorsen et al. (2002) "Microfluidic large-scale integration," Science. 298:580-584.
Thuillier et al. (2005) "Development of a low cost hybrid Si/PDMS multi-layered pneumatic microvalve," Microsystem Technologies. 12(1):180-185.
Tian et al. (2004) "Integrated genomic and proteomic analyses of gene expression in mammalian cells," Mol. Cell. Proteomics. 3:960-969.
Toner et al. (2005) "Blood-on-a-chip," Annual Review of Biomedical Engineering. 7:77-103.
Van Duijn et al. (2002) "Detection of genetically modified organisms in foods by protein- and DNA-based techniques: bridging the methods," J AOAC Int. 85(3):787-791.
Wacker (2004) "DDi-microFIA—A readily configurable microarray-fluorescence immunoassay based on DNA-directed immobilization of proteins," Chembiochem. 5:453-459.
Wegner et al. (2003) "Fabrication of Histidine-Tagged Fusion Protein Arrays for Surface Plasmon Resonance Imaging Studies of Protein-Protein and Protein-DNA Interactions," Analytical Chemistry. 75:4740-4746.
Whitesides et al. (2001) "Soft lithography in biology and biochemistry," Annual Review of Biomedical Engineering. 3:335-373.
Wysocki et al. (1978) "Panning for lymphocytes: a method for cell selection," Proc. Natl. Acad. Sci. USA. 75 (6):2844-2848.
Yang et al. (2006) "A microfluidic device for continuous, real time blood plasma separation," Lab on a Chip. 6:871-880.
Yu et al. (2005) "Contextual interactions determine whether the *Drosophila* homeodomain protein, Vnd, acts as a repressor or activator," Nucleic Acids Research. 33(8):1-11.
Zimmermann et al. (2005) "Modeling and optimization of high-sensitivity, low-volume microfluidic-based surface immunoassays," Biomedical Microdevices. 7(2):99-110.
European Search Report corresponding to European Patent Application No. 08796213.0, dated Oct. 4, 2013.
International Search Report corresponding to International Patent Application No. PCT/US2008/070232, dated Dec. 18, 2008.
International Search Report corresponding to International Patent Application No. PCT/US2008/070236, dated Feb. 6, 2009.
International Search Report corresponding to International Patent Application No. PCT/US2009/040106, dated Dec. 16, 2009.

Office Action corresponding to U.S. Appl. No. 11/888,502, dated Jul. 8, 2009.
Office Action corresponding to U.S. Appl. No. 12/174,598, dated Jun. 29, 2009.
Office Action corresponding to U.S. Appl. No. 12/174,601, dated May 17, 2011.
Office Action corresponding to U.S. Appl. No. 12/174,601, dated Oct. 24, 2014.
Office Action corresponding to U.S. Appl. No. 12/174,601, dated Oct. 28, 2010.
Restriction Requirement corresponding to U.S. Appl. No. 11/888,502, dated Jan. 30, 2009.
Restriction Requirement corresponding to U.S. Appl. No. 12/174,601, dated Jul. 8, 2010.
Written Opinion corresponding to International Patent Application No. PCT/US2007/017258, completed Dec. 18, 2007.
Written Opinion corresponding to International Patent Application No. PCT/US2008/070232, completed Dec. 18, 2008.
Written Opinion corresponding to International Patent Application No. PCT/US2008/070236, completed Feb. 6, 2009.
Written Opinion corresponding to International Patent Application No. PCT/US2009/040106, completed Dec. 10, 2009.
Inerowicz et al. (2002) "Multiprotein immunoassay arrays fabricated by microcontact printing," Langmuir. 18:5263-5268.
Ivanova et al. (2002) "Polymer Microstructures Fabricated via Laser Ablation Used for Multianalyte Protein Microassay," Langmuir. 18:9539-9546.
Jeon et al. (1991) "Protein—surface interactions in the presence of polyethylene oxide: I. Simplified theory," Journal of Colloid and Interface Science. 142(1):149-158.
Jeon et al. (1991) "Protein—surface interactions in the presence of polyethylene oxide: II. Effect of protein size," Journal of Colloid and Interface Science. 142(1):159-166.
Kim et al. (1979) "Establishment and characterization of BALB/c lymphoma lines with B cell properties," J. Immunol. 122:549-554.
Kiyonaka et al. (2004) "Semi-wet peptide/protein array using supramolecular hygrogel," Nature Materials. 3:58-64.
Kozlov et al. (2004) "Efficient strategies for the conjugation of oligonucleotides to antibodies enabling highly sensitive protein detection," Biopolymers. 73:621-630.
Kwon et al. (2004) "Antibody arrays prepared by cutinase-mediated immobilization on self-assembled monolayers," Anal. Chem. 76:5713-5720.
Kwong et al. (2005) "Synchronous global assessment of gene and protein expression in colorectal cancer progression," Genomics. 86:142-158.
Lamb et al. (2006) "The Connectivity Map: using gene-expression signatures to connect small molecules, genes, and disease," Science. 313(5795):1929-1935.
Lambeck et al. (2007) "Serum cytokine profiling as a diagnostic and prognostic tool in ovarian cancer: a potential role for interleukin 7," Clinical Cancer Research. 13:2385-2391.
Lange et al. (2004) "Microcontact printing of DNA molecules," Analytical Chemistry. 76:1641-1647.
Lathrop (2003) "Therapeutic potential of the plasma proteome," Current Opinion in Molecular Therapeutics. 5:250-257.
Lee et al. (2001) "SPR Imaging Measurements of 1-D and 2-D DNA Microarrays Created from Microfluidic Channels on Gold Thin Films," Analytical Chemistry. 73(22):5525-5531.
Lin et al. (2005) "Evidence for the Presence of Disease-Perturbed Networks in Prostate Cancer Cells by Genomic and Proteomic Analyses: A Systems Approach to Disease," Cancer Res. 65:3081-3091.
Lin et al. (2007) "A cytokine-mediated link between innate immunity, inflammation, and cancer," Journal of Clinical Investigation. 117:1175-1183.
Liu et al. (2000) "Photopatterning of antibodies on biosensors," Bioconjugate Chem. 11:755-761.
Macbeath et al. (2000) "Printing proteins as microarrays for high-throughput function determination," Science. 289:1760-1763.
Madoz-Gúrpide et al. (2001) "Protein based microarrays: A tool for probing the proteome of cancer cells and tissues," Proteomics. 1(10):1279-1287.

(56) References Cited

OTHER PUBLICATIONS

Martin et al. (2006) "Molecular biology of breast cancer," Clin. Trans. Oncol. 8(1):7-14.
Mellinghoff et al. (2006) "Molecular determinants of the response of glioblastomas to EGFR kinase inhibitors," N. Engl. J. Med. 353:2012-2024.
Michel et al. (2002) "Printing meets lithography: Soft approaches to high-resolution patterning," Chimia. 56:527-542.
Mischel et al. (2004) "DNA-microarray analysis of brain cancer: molecular classification for therapy," Nature Rev. Neurosci. 5:782-794.
Nagrath et al. (2007) "Isolation of rare circulating tumour cells in cancer patients by microchip technology," Nature. 450:1235-1239.
Nam et al. (2003) "Nanoparticle-based bio-bar codes for the ultrasensitive detection of proteins," Science. 301:1884-1886.
Nam et al. (2003) "Nanoparticle-based bio-bar codes for the ultrasensitive detection of proteins," Science. 301:1884-1886.—Supporting Material pp. 1 to 12.
Niemeyer (2007) "Functional devices from DNA and proteins," Nano Today. 2:42-52.
Niemeyer et al. (2005) "Immuno-PCR: high sensitivity detection of proteins by nucleic acid amplification," Trends in Biotechnology. 23:208-216.
Ottesen et al. (2006) "Microfluidic digital PCR enables multigene analysis of individual environmental bacteria," Science. 314:1464-1467.
Pal et al. (2006) "Differential Phosphoprotein Mapping in Cancer Cells Using Protein Microarrays Produced from 2-D Liquid Fractionation," Anal. Chem. 78:702-710.
Park et al. (2002) "Array-Based Electrical Detection of DNA with Nanoparticle Probes," Science. 295:1503-1506.
Peluso et al. (2003) "Optimizing antibody immobilization strategies for the construction of protein arrays," Anal. Biochem. 312:113-124.
Phillips (2004) "Rapid analysis of inflammatory cytokines in cerebrospinal fluid using chip-based immunoaffinity electrophoresis," Electrophoresis. 25:1652-1659.
Pirrung (2002) "How to make a DNA chip," Angew. Chem. Int. Ed. 41:1276-1289.
Prados et al. (2003) "Temozolomide + OSI-774," Proc. Am. Soc. Clin. Oncology. 22:99.
Prime et al. (1991) "Self-assembled organic monolayers: model systems for studying adsorption of proteins at surfaces," Science. 252:1164-1167.
Prime et al. (1993) "Adsorption of proteins onto surfaces containing end-attached oligo(ethylene oxide): a model system using self-assembled monolayers," J. Am. Chem. Soc. 115(23)10714-10721.
Quake et al. (2000) "From Micro- to Nanofabrication with Soft Materials," Science. 290:1536-1540.
Radich et al. (2006) "Gene expression changes associated with progression and response in chronic myeloid leukemia," Proc. Natl. Acad. Sci. USA. 103(8):2794-2799.
Ramsden (1995) "Puzzles and Paradox in Protein Adsorption," J. Chem. Soc. Rev. 24:73-78.
Rich et al. (2004) "Phase II trial of gefitinib in recurrent glioblastoma," J. Clin. Oncology 22:133-142.
Sano et al. (1992) "Immuno-PCR: very sensitive antigen detection by means of specific antibody-DNA conjugates," Science. 258:120-122.
Schena et al. (1995) "Quantitative monitoring of gene expression patterns with a complementary DNA microarray," Science. 270:467-470.
Schweitzer et al. (2002) "Multiplexed protein profiling on microarrays by rolling-circle amplification," Nature Biotechnology. 20:359-365.
Seigel et al. (1997) "On-line detection of nonspecific protein absorption at artificial surfaces," Anal. Chem. 69:3321-3328.
Sia et al. (2003) "Microfluidic devices fabricated in poly(dimethylsiloxane) for biological studies," Electrophoresis. 24:3563-3576.
Soen et al. (2003) "Detection and characterization of cellular immune responses using peptide-MHC microarrays," PLoS Biology. 1(3):429-438.
Spiro et al. (2000) "A bead-based method for multiplexed identification and quantitation of DNA sequences using flow cytometry," 66(10):4258-4265.
Svanes et al. (1968) "Variations in small blood vessel hematocrits produced in hypthermic rats by micro-occlusion," Microvascular Research. 1:210-220.
Taton et al. (2000) "Scanometric DNA array detection with nanoparticle probes," Science. 289:1757-1760.
Canadian Patent Application No. 2,694,545, Office Action dated Jan. 17, 2018, 4 pp.
European Patent Application No. 08796213.0, Office Action dated Feb. 8, 2018, 4 pp.
Partial European Search Report in corresponding European Patent Application No. EP 19 18 0665, dated Jan. 2, 2020 (13 pages).
Fan et al., "Integrated barcode chips for rapid, multiplexed analysis of proteins in microliter quantities of blood", Nature Biotechnology, 2008, vol. 26, No. 12, p. 1373-1378.
Liotta et al., "Protein microarrays: Meeting analytical challenges for clinical applications", Cancer Cell, 2003, vol. 3, p. 317-325.
Love et al., "A microengraving method for rapid selection of single cells producing antigenspecific antibodies", Nature Biotechnology, 2006, vol. 24, No. 6, p. 703-707.
Sorger, P. "Microfluidics closes in on point-of-care assays", Nature Biotechnology, 2008, vol. 26, No. 12, p. 1345-1346.
Unger et al., "Monolithic microfabricated valves and pumps by multilayer soft lithography", Science, 2000, vol. 288, p. 113-116.

\* cited by examiner

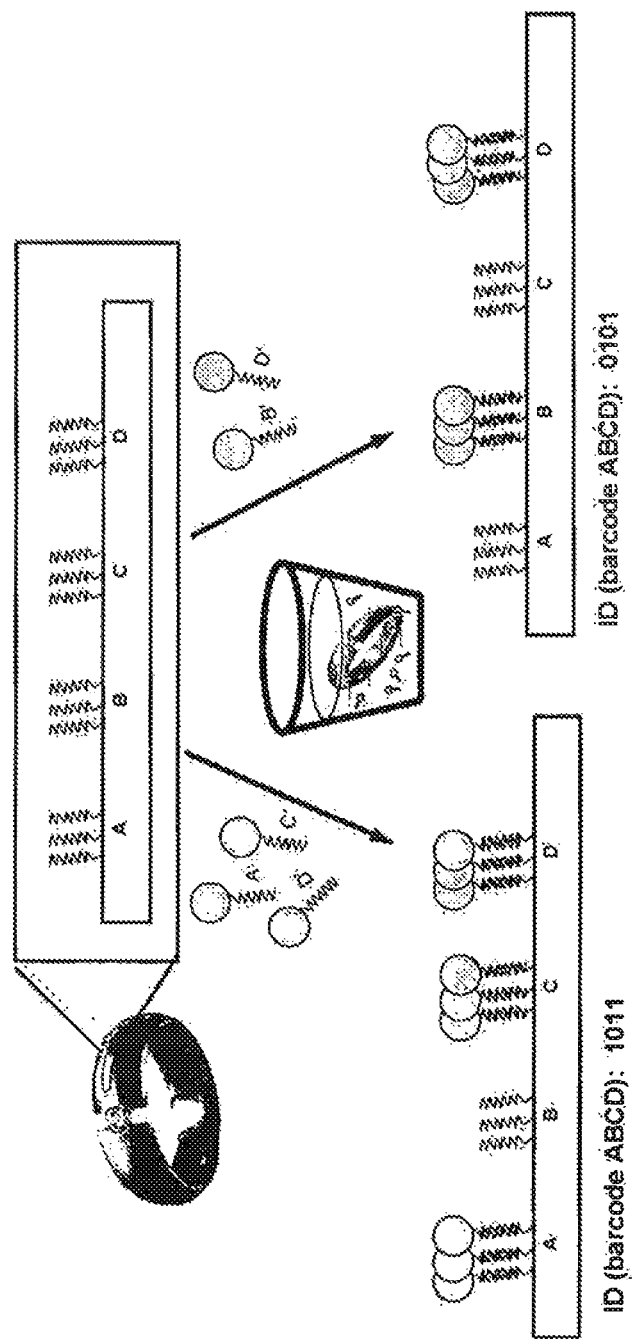

ARRAYS, SUBSTRATES, DEVICES, METHODS AND SYSTEMS FOR DETECTING TARGET MOLECULES

CROSS REFERENCE TO RELATED APPLICATIONS

This application is a continuation of U.S. patent application Ser. No. 14/694,340 filed Apr. 23, 2015, which is a continuation of U.S. patent application Ser. No. 12/174,601 filed Jul. 16, 2008, now abandoned, which claims priority to U.S. Provisional Patent Application No. 60/998,981, filed on Oct. 15, 2007, and to U.S. Provisional Patent Application No. 60/959,666, filed on Jul. 16, 2007, the disclosures of which are incorporated herein by reference in their entirety.

STATEMENT OF GOVERNMENT GRANT

This invention was made with government support under Grant No. CA119347 awarded by the National Institutes of Health. The government has certain rights in the invention.

TECHNICAL FIELD

The present disclosure relates to patterning of materials, performance of assays and in particular detection of target molecules in a sample. More specifically, it relates to arrays, devices, methods and systems for detecting a plurality of target molecules in a sample.

BACKGROUND

Detection of target molecules and in particular of biomarkers has been a challenge in the field of biological molecule analysis. In particular, qualitative and quantitative detection of biomarkers is often a critical step in several applications ranging from diagnostics to fundamental biology studies.

In particular, qualitative and quantitative detection of multiple biomarkers has become increasingly important in several applications, such as clinical diagnostic wherein accurate detection of a plurality of biomarkers is desired. More particularly, in some of those applications detection of the multiple biomarkers is directed to identify a biological profile (e.g. proteome and/or metabolome) which can be associated to an indication of interest (e.g. a diagnostic indication).

Detection of multiple biomarkers is performed by several surface-bound assays known in the art. In those assays capture agents (e.g. primary antibodies) attached to a surface (e.g. a substrate surface) bind the targets of interest in capture agent binding complexes. The capture agent binding complexes are then detected, typically through further binding of the targets with labeling molecules (e.g. secondary antibodies coupled with fluorescent dyes).

A number of critical parameters is associated with successful execution of a surface-bound assay and include: a) sensitivity of the assay, or minimum concentration, of the biomolecule that can be detected, b) concentration range over which that biomolecule can be detected, c) numbers of different biomolecules that can simultaneously be detected, d) variability from measurement to measurement, e) numbers of different types of biomolecules (e.g. mRNAs, proteins, etc.) that can simultaneously be detected, f) minimum sample size required for the measurement, and g) speed at which the measurement can be performed.

A number of those assays are typically performed in a microfluidic environment. Microfluidics-based assays are particularly attractive for applications where minimum sample size and short time of execution are desired, because they require only small amounts of biological materials and small amounts of capture agents, materials and associated reagents.

SUMMARY

Provided herein, are devices, methods and systems for detection of a plurality of targets that allow a fast and sensitive detection of a large number of multiple targets in a sample and/or provide results in an easily readable fashion.

According to a first aspect, an array for detecting at least one target in a sample, and in particular a plurality of targets in a sample is disclosed. The array comprises, at least one capture agent or component thereof attached to a substrate, the at least one capture agent capable of specifically binding the at least one target to form a capture agent target binding complex. In the array, the at least one capture agent or component thereof arranged on the array so that capture agent target binding complexes are detectable along substantially parallel lines forming a barcoded pattern. The at least one target can be a plurality of targets, the capture agent can be a plurality of capture agents, with each capture agent of the plurality of capture agents bindingly distinguishable and positionally distinguishable from another and capable of specifically binding each target of the plurality of targets to form a capture agent target binding complex.

According to a second aspect, a microfluidic device is disclosed that comprises an array according to the present disclosure.

According to a third aspect, a system for the detection of a plurality of targets in a sample is disclosed. The system comprises an array disclosed herein and a device for detecting the barcoded pattern on the array.

According to a fourth aspect, a method for detecting a plurality of targets in a sample is disclosed. The method comprises: contacting said sample with an array herein disclosed for a time and under conditions to allow binding of said plurality of targets with said plurality of capture agents to form capture agent target binding complexes; and detecting said capture agent target binding complexes.

According to a fifth aspect, a substrate is disclosed, the substrate for detecting a target, and in particular a plurality of targets, in a sample. The substrate is configured to allow attachment of the target on the substrate so that said target is detectable along substantially parallel lines forming a barcoded pattern.

According to a sixth aspect, a microfluidic device is disclosed that comprises a substrate according to the present disclosure.

According to a seventh aspect, a system for the detection of a target, and in particular a plurality of targets, in a sample is disclosed. The system comprises a substrate disclosed herein and a device for detecting the barcoded pattern on the substrate.

According to an eighth aspect, a method for detecting a target and, in particular, a plurality of targets, in a sample is disclosed. The method comprises: contacting said sample with a substrate herein disclosed for a time and under conditions to allow binding of said target with said substrate; and detecting said target attached to the substrate.

According to a ninth aspect, a method to attach a molecule on a microfluidic support along a predetermined microfluidic pattern is disclosed. The method comprises: providing a mold comprising microfluidic channels, the microfluidic channels having an inlet and an outlet, the outlets of the channels configured to form part of the predetermined pattern, providing the support, said support suitable to be coupled with the mold, coupling the mold with the support, providing the molecule in the microfluidic channels for a time and under conditions to allow attachment of the molecule on the support; and decoupling the mold from the support.

According to a tenth aspect a system to attach a molecule on a microfluidic support along a predetermined microfluidic pattern is disclosed. The system comprises: a mold comprising microfluidic channels, the microfluidic channels having an inlet and an outlet, the outlets of the channels configured to form part of the predetermined pattern, and a support suitable to be coupled with the mold.

The methods and systems for attaching a molecule on a support on a microfluidic support along a predetermined microfluidic pattern can be used to manufacture an array and/or a substrate according to the present disclosure, in embodiments wherein the pattern is composed of substantially parallel lines forming a barcoded pattern.

Arrays, substrates, devices, methods and systems herein disclosed provide information in a one-dimensional fashion which can be detected with a single line scan (line profile) perpendicular to the strip direction to complete reading all information. In this way, is possible to obtain all the necessary information without need of a precise move of a reader (e.g. a scan head) which is instead required in imaging 2D array of the art. This feature can allow, in certain embodiments, the reading of barcode DNA array as easy as scanning the product barcode in supermarket.

Arrays, substrates, devices, methods and systems herein disclosed can provide an increased concentration of capture agents suitable to bind the target and, therefore, increased detection sensitivity (e.g. up to 0.1 picomolar) when compared to prior art techniques.

Arrays, substrates, devices, methods and systems herein disclosed can allow an increased number of locations for a specific capture agent on a surface (herein also indicated as spots). Accordingly, the arrays, devices methods and systems herein disclosed also allow detection of an increased number of targets or target related parameters (e.g. 50 targets or more) in comparison with the ones detectable with prior art techniques.

Arrays, substrates, devices, methods and systems herein disclosed are also compatible with microfluidic fabrication techniques, since the spots can be placed in positions that can be defined not only with respect to each other, but also with respect to microfluidic channels and/or other structure on the surface.

Arrays, substrates, devices, methods and systems herein disclosed allow providing high density capture agents on a substrate, with a decreased level of impurities in comparison to prior art techniques.

Arrays, substrates, devices, methods and systems herein disclosed also allow detection of a larger number of biomarkers in a reduced time (e.g. about 9 minutes) with respect prior art techniques, in particular in embodiments wherein the array is integrated with microfluidics.

Arrays, substrates, devices, methods and systems herein disclosed allow detection from a sample reduced in size (e.g. 500 nano liter per barcode and/or protein sections from only one cell) in comparison to the samples analyzed with prior art techniques, in particular in embodiments wherein the array is integrated with microfluidics Additionally, since the arrays, substrates, devices, systems and methods herein disclosed allow detection of multiple biomarkers within the same environment, and in particular the same microfluidics environment, using a single assay technique, the relative error associated with measurements of different biomarkers from the same sample is minimized.

The arrays, substrates, devices, methods and systems herein disclosed are applicable to performance of the detection of various types of target molecules that can bind to immobilized capture agents. Suitable target molecules include, but are not limited to, proteins, peptide, polypeptide, ligands, metabolites, nucleic acid, polynucleotide, carbohydrate, amino acid, hormone, steroid, vitamin, drug, drug candidate, virus, bacteria, cells, microorganisms, fragments, portions, components, products, epitopes of virus, bacteria, microorganisms and/or cells, polysaccharides, lipids, lipopolysaccharides, glycoproteins, cell surface markers, receptors, immunoglobulins, albumin, hemoglobin, coagulation factors, volatile gas molecules, particles, metal ions and the antibodies to any of the above substrates.

The arrays, substrates, devices, methods and systems herein disclosed are applicable to performance of assays including diagnostic assays, environmental monitoring assays, heath/drug response monitoring assays and assays performed for research purposes. Exemplary assays that can be performed include but are not limited to detection of cancer biomarkers (e.g. prostate cancer antigen (PSA), and human chorionic gonadotropin (hCG)), detection of liver toxicity biomarker C-reactive protein (CRP) and plasminogen, detection of immuno complement proteins like C3, detection of cytokines such as interferon gamma (IFN-gamma), tumor necrosis factor alpha (TNF-a), interleukin 1 alpha (IL-1 alpha), interleukin 1 beta (IL-1 beta), transforming growth factor beta (TGF beta), interleukin 6 (IL-6), interleukin 10 (IL-10), interleukin 12 (IL-12), granulocyte macrophage colony stimulating factor (GM-CSF) etc, detection of chemokines: CCL2 (also called monocyte chemoattractive protein-1, MCP-1), and demonstration of detection of complementary DNA molecules.

Additional applications of the arrays, substrates, devices, methods and systems herein disclosed include but are not limited to use the patterning technique to make a barcode array of gas selective polymers as gas sensors; patterning liquid crystal film for LCD, and assemble magnetic particle array using DNA-iron oxide nanoparticle conjugates (just like the antibody-DNA conjugates) for magnetic barcodes (product ID).

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the disclosure.

FIG. 24 shows an exemplary detection of a target at different concentration ranges according to an embodiment herein disclosed.

FIG. 25 shows data concerning the exemplary detection of a biological profile of FIG. 20A.

FIG. 31 shows a schematic representation of the method to manufacture a patterned substrate according to an embodiment herein disclosed.

DETAILED DESCRIPTION

Figure 1:
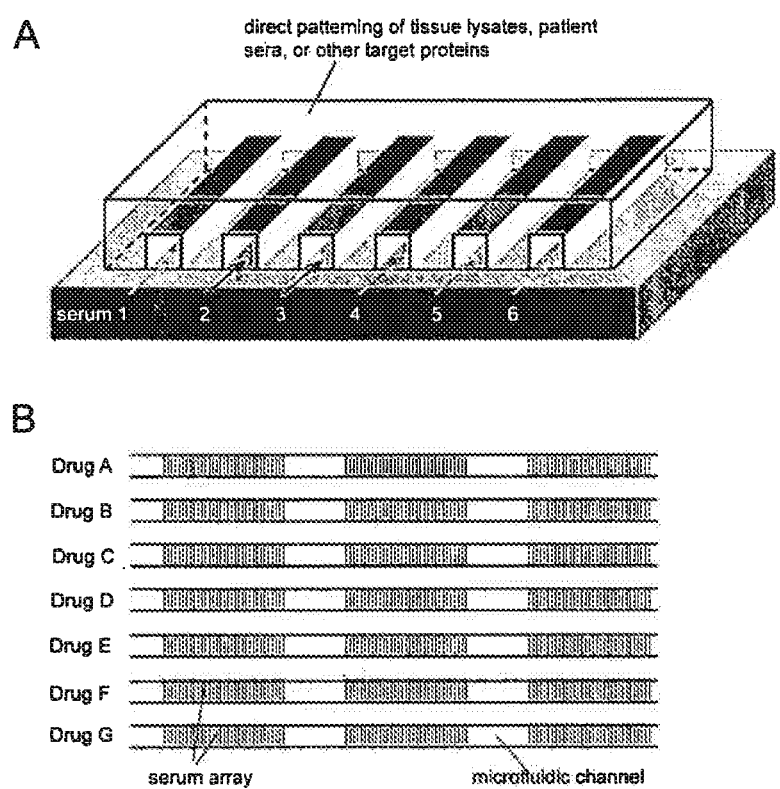
FIG. 1 shows a schematic representation of the method to manufacture a reversed or inversed phase barcoded array according to an embodiment herein disclosed. Panel A shows a barcode pattern including a number of stripes or bars corresponding to immobilized serum molecules from various patients. Panel B shows a barcode pattern wherein the bars are provided by microfluidic channels formed on top of the array of Panel A.

Arrays, substrates, devices, methods and systems for detecting a target, and in particular, a plurality of target molecules in a sample are herein disclosed.

The term "detect" or "detection" as used herein indicates the determination of the existence, presence or fact of a target or signal in a limited portion of space, including but not limited to a sample, a reaction mixture, a molecular complex and a substrate. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

The term "target" or "target molecule" as used herein indicates an analyte of interest. The term "analyte" refers to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, amino acids, peptides proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state. Exemplary biomarkers include breast cancer marker HER2, ovarian cancer marker CA125, and heart disease marker thrombin.

The term "sample" as used herein indicates a limited quantity of something that is indicative of a larger quantity of that something, including but not limited to fluids from a biological environment, specimen, cultures, tissues, commercial recombinant proteins, synthetic compounds or portions thereof.

In some embodiments, arrays, substrates, methods and systems are herein disclosed for the detection of multiple, distinct targets, such as biomolecules, or a panel of biomarkers. In the arrays, substrates, devices methods and systems herein disclosed each target is detected in a particular location on a surface, and the collection of detected biomolecules forms a pattern, or a barcode. In particular, the arrays, devices, methods and systems herein disclosed can apply to the detection of the biomarker panel within a micro fluidics environment.

In some embodiments of the arrays, substrates devices methods and systems herein disclosed a plurality of capture agents attached to a substrate.

The wording "capture agents" as used herein indicate a molecule capable of specific binding with a predetermined binding. Exemplary capture agents include but are not limited to polynucleotides and proteins, and in particular antibodies.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar, joined to a purine or pyrimidine base and to a phosphate group and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term polynucleotide includes nucleic acids of any length DNA RNA analogs and fragments thereof. A polynucleotide of three or more nucleotides is also called nucleotidic oligomers or oligonucleotide.

The term "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer or oligopeptide. As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules.

The term "antibody" as used herein refers to a protein that is produced by activated B cells after stimulation by an antigen and binds specifically to the antigen promoting an immune response in biological systems and that typically consists of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab Fv, Fab' F(ab')2 and the like. A monoclonal antibody is an antibody that specifically binds to and is thereby defined as complementary to a single particular spatial and polar organization of another biomolecule which is termed an "epitope". A polyclonal antibody refers to a mixture of monoclonal antibodies with each monoclonal antibody binding to a different antigenic epitope. Antibodies can be prepared by techniques that are well known in the art, such as immunization of a host and collection of sera (polyclonal) or by preparing continuous hybridoma cell lines and collecting the secreted protein (monoclonal).

The wording "specific" "specifically" or specificity" as used herein with reference to the binding of a molecule to another refers to the recognition, contact and formation of a stable complex between the molecule and the another, together with substantially less to no recognition, contact and formation of a stable complex between each of the molecule and the another with other molecules. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence.

The term "attach" or "attached" as used herein, refers to connecting or uniting by a bond, link, force or tie in order to keep two or more components together, which encompasses either direct or indirect attachment such that for example where a first molecule is directly bound to a second molecule or material, and the embodiments wherein one or more intermediate molecules are disposed between the first molecule and the second molecule or material.

The term "substrate" as used herein indicates an underlying support or substratum. Exemplary substrates include solid substrates, such as glass plates, microtiter well plates, magnetic beads, silicon wafers and additional substrates identifiable by a skilled person upon reading of the present disclosure.

In some embodiments, the capture agents used in the arrays, devices, methods and systems herein disclosed can be either directly deposited onto substrate to form an array or immobilized by linker molecules that are pre-deposited onto substrate and capable to specific binding to capture agent for form an array. Since they are functional to the attachment of capture agents to a substrate, linker molecules can be considered as capture agent components.

In the arrays, substrates, devices, methods and systems herein disclosed, wherein multiple capture agents are used, each capture agent can be bindingly distinguishable and/or positionally distinguishable from another.

The wording "bindingly distinguishable" as used herein with reference to molecules, indicates molecules that are distinguishable based on their ability to specifically bind to, and are thereby defined as complementary to a specific molecule. Accordingly, a first molecule is bindingly distinguishable from a second molecule if the first molecule specifically binds and is thereby defined as complementary to a third molecule and the second molecule specifically binds and is thereby defined as complementary to a fourth molecule, with the fourth molecule distinct from the third molecule.

The wording "positionally distinguishable" as used herein refers to with reference to molecules, indicates molecules that are distinguishable based on the point or area occupied by the molecules. Accordingly, positionally distinguishable capture agents are substrate polynucleotide that occupy different points or areas on the assaying channel and are thereby positionally distinguishable.

In arrays herein disclosed, each capture agent of the plurality of capture agents is capable of specifically binding each target of the plurality of targets to form a capture agent target binding complex, and the plurality of capture agents arranged on the array so that capture agent target binding complexes are detectable along substantially parallel lines forming a barcoded pattern.

In other embodiments, substrates systems and methods are herein disclosed wherein the substrate is configured to allow attachment of targets (herein also reverse barcode or inversed-phase barcode), and in particular detectable targets, along substantially parallel lines forming a barcoded pattern. An exemplary illustration of reverse barcode is illustrated in FIG. 1, wherein a barcoded pattern including a number of bars corresponding to immobilized serum molecules from various patients and microfluidic channels for providing various drugs to be contacted with the serum of the patients for a bio-assay, are shown.

In some embodiments, detection of the attached target and/or capture agent target complex is performed by providing a labeled molecule, which includes any molecule that can specifically bind a capture agent target complex to be detected (e.g. an antibody, aptamers, peptides etc) and a label that provides a labeling signal, the label compound attached to the molecule. The labeled molecule is contacted with the attached target and/or capture agent target complex and the labeling signal from the label compound bound to attached target and/or the capture agent-target complex on the substrate can then be detected, according to procedure identifiable by a skilled upon reading of the present disclosure and, in particular, of the Examples section.

In particular, the signal readout that is used in the arrays, devices, methods and systems herein disclosed can be realized using labels such as probes that transduce the capture event of target molecule into optical, electrical or magnetic signal. Exemplary probes include, but not limited to, fluorescent dyes, gold nanoparticles, silver nanoparticles, semiconductor nanoparticles (e.g. CdSe, ZnSe and/or their core-shell nanoparticles), and iron oxide nanoparticles.

The terms "label" and "labeled molecule" as used herein as a component of a complex or molecule refer to a molecule capable of detection, including but not limited to radioactive isotopes, fluorophores, chemoluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence the wording and "labeling signal" as used herein indicates the signal emitted from the label that allows detection of the label, including but not limited to radioactivity, fluorescence, chemoluminescence, production of a compound in outcome of an enzymatic reaction and the likes.

In embodiments wherein one or more targets and/or a plurality of targets is detected described below in more details, the labeled molecule can be formed of a plurality of labeled molecules. Each labeled molecules comprises a molecule that specifically binds one target of the one or more targets/plurality of targets and a label compound attached to the molecule, the label compound providing a labeling signal, each labeled molecule detectably distinguishable from another.

The wording "detectably distinguishable" as used herein with reference to labeled molecule indicates molecules that are distinguishable on the basis of the labeling signal provided by the label compound attached to the molecule. Exemplary label compounds that can be use to provide detectably distinguishable labeled molecules, include but are not limited to radioactive isotopes, fluorophores, chemoluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and additional compounds identifiable by a skilled person upon reading of the present disclosure.

In embodiments, wherein bindingly distinguishable capture agents are used different analytes can be detected by use of detectably distinguishable labeled molecules each specific to a separate analyte of interest.

In some embodiments, the detection method can be carried via fluorescent based readouts, in which the labeled antibody is labeled with fluorophore which includes but is not limited to small molecular dyes, protein chromophores and quantum dots. In other embodiments, on-chip detection can be performed with methods other than fluorescence based techniques. Exemplary suitable techniques include, colorimetric detection, enzyme-catalyzed production of different colored or fluorescent dyes (with different colors being associated with distinct analytes), microparticle/nanoparticle based detection using electron microscopy, AFM, or dark-field microscopy, magnetic detection using magnetic micro/nanoparticles, electrical detection methods.

In some embodiments, detection can be performed by methods that use signal amplification such as gold nanoparticle based detection followed by gold or silver amplification. In particular, in some embodiments, in any of the methods and systems herein disclosed, detection can be carried out on gold nanoparticle-labeled secondary detection systems in which a common photographic development solution can amplify the gold nanoparticles as further described below. Also, if the readout comes from dark field scattering of gold particles, single molecule digital proteomics is enabled.

The detection can be performed with the aid of suitable equipments. In particular any equipment configured to read barcoded pattern can be used as long as the relevant sensitivity is applicable to the detection of choice.

Figure 2:
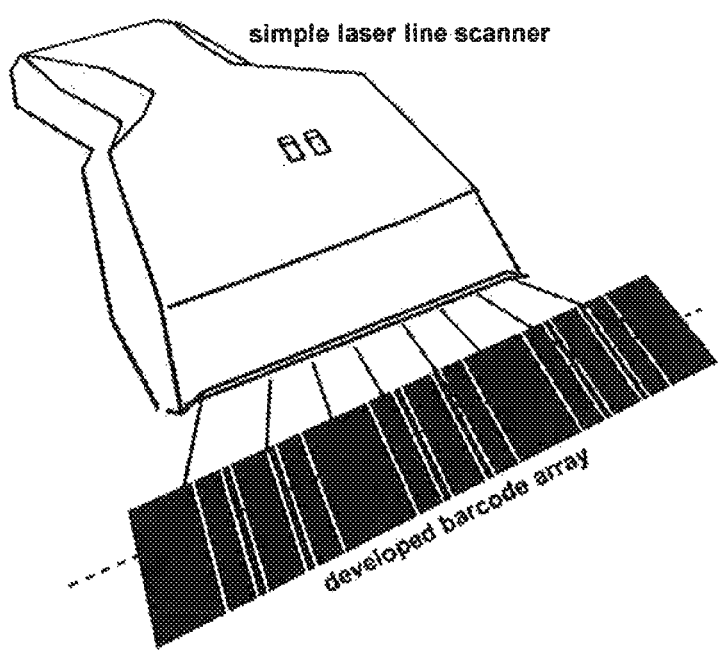
FIG. 2 shows a schematic representation of a method and equipment to detect a barcoded array according to an embodiment herein disclosed.
Figure 3:
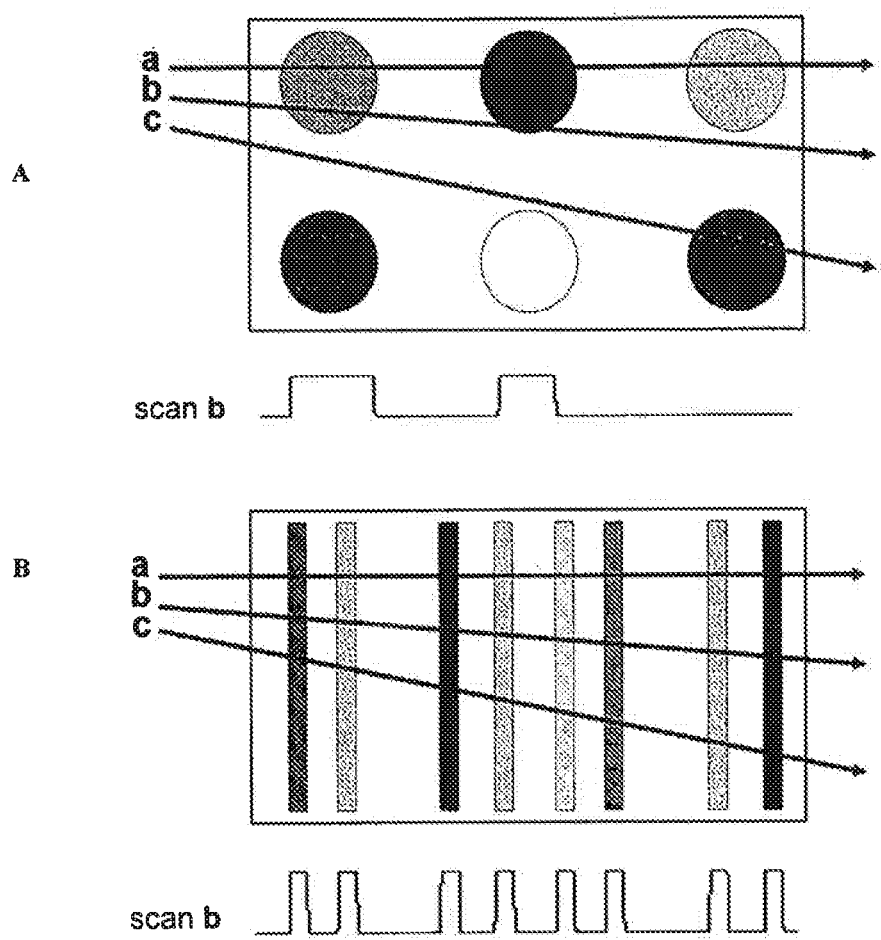
FIG. 3 shows a schematic representation of a comparative detection of a spot array and of a barcoded array according to an embodiment herein disclosed.

For example, in some embodiments, reading the information of the arrays herein disclosed can be performed using a simple line-scan reader such as the laser line scanner schematically illustrated in FIG. 2. The one-dimensional layout of the arrays renders a higher reliability as compared to the conventional circular spot arrays as schematically illustrated in FIG. 3. In the illustration of FIG. 3, is shown how a scan reading from a same line scanner (scan b) provides a higher reliability for a barcoded pattern (panel B) if compared with a spotted array (Panel A).

Additional equipment suitable to detect the array herein described can be identified by a skilled person upon reading of the present disclosure. For example. when fluorescent probes are used for signal readout, laser microarray scanner (such as. Axon Genepix 4000 series scanner, Affymetrix 300 scanner, etc), scanning laser confocal microscope (e.g. Nikon Eclipse C1si microscope) can be used to visualize the pattern. In particular, the parallel-stripe pattern allows a single scan of laser to read out full information with high fidelity and reliability as illustrated in FIGS. 2 and 3. This feature opens the possibility of implementing a simple laser line scanner similar as the barcode reader in supermarket for reading the barcode array described herein.

In other embodiments, wherein gold nanoparticles are used, light scattering microscope (such as Nikon® Eclipse LV100) can be used. In other embodiments, wherein electroless metal plating is used to enhance the nanoparticle signal, a flat bed scanner (such as Nanosphere Verigene® reader) can be used besides light scattering microscopes. In still other embodiments, wherein magnetic particles are used as probes, a magnetoresistive sensor similar to a scan head in a hard disk can be used to read out the barcode information.

Additional techniques are identifiable by a skilled person upon reading of the present disclosure and will not be further discussed in details.

Arrays and substrates herein disclosed can be manufactured using methods and systems to attach a material to a support along a predetermined pattern herein also disclosed (herein also indicated as patterning methods and systems). The methods and systems to attach material can be used to manufacture arrays and substrate according to any predetermined pattern. In embodiments, wherein the patterned material is configured along substantially parallel lines forming a barcoded pattern, the methods and systems herein disclosed can be used to manufacture barcoded arrays and substrates.

In some embodiments, the barcoded surface patterning can be performed as described below in the exemplary procedure illustrated with reference to microfluidics channels patterned from polydimethylsiloxane (PDMS) that are weakly or strongly bonded to glass substrates. A skilled person would understand that the patterning method is not limited the specific microfluidic features and materials used and that a different number of channels with different dimensions as well other materials, such as injection molded micro fluidics channels, semiconductor wafers, etc., all identifiable by a skilled person upon reading of the present disclosure, may all be utilized.

Figure 4:
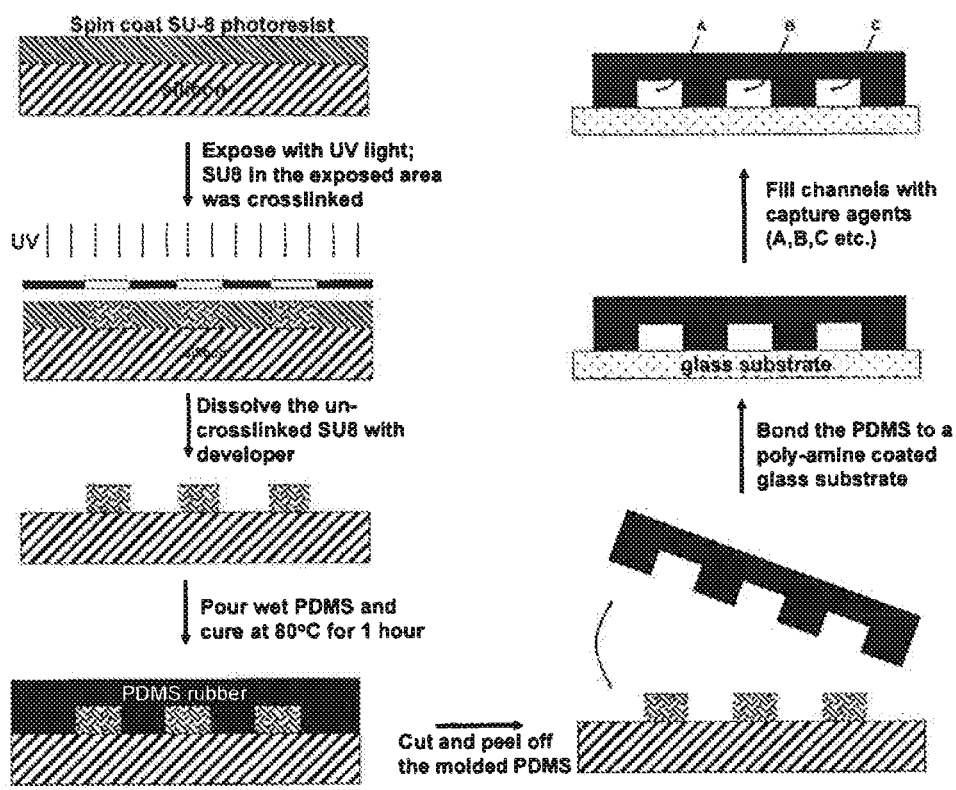
FIG. 4 shows a schematic representation of an exemplary passage in the pattering methods and systems for producing a barcoded array according to an embodiment herein disclosed.

In some embodiments, a mold can be fabricated by molding a polymer such as a PDMS elastomer from a master template, to include microchannels each having an inlet and an outlet and each of the outlets is such that it forms a portion of the desired pattern (in particular a barcoded pattern). In some embodiments, the polymer is molded using photolithography to create a photoresist pattern on a silicon wafer. Those embodiments, allow a particularly rapid prototyping. An exemplary illustration of a mold fabrication for the patterning methods and systems herein disclosed is illustrated in FIG. 4 wherein fabrication of a PDMS microchannel stamp for flow patterning of a barcode array is disclosed.

In another embodiment, the mold can be manufactured by providing a silicon "hard" master and by transferring the photolithographically-defined pattern into the underlying silicon wafer using a deep reactive ion etching (DRIE) process. Those embodiments allow a robust and reusable mold for higher throughput chip fabrication.

Figure 5:
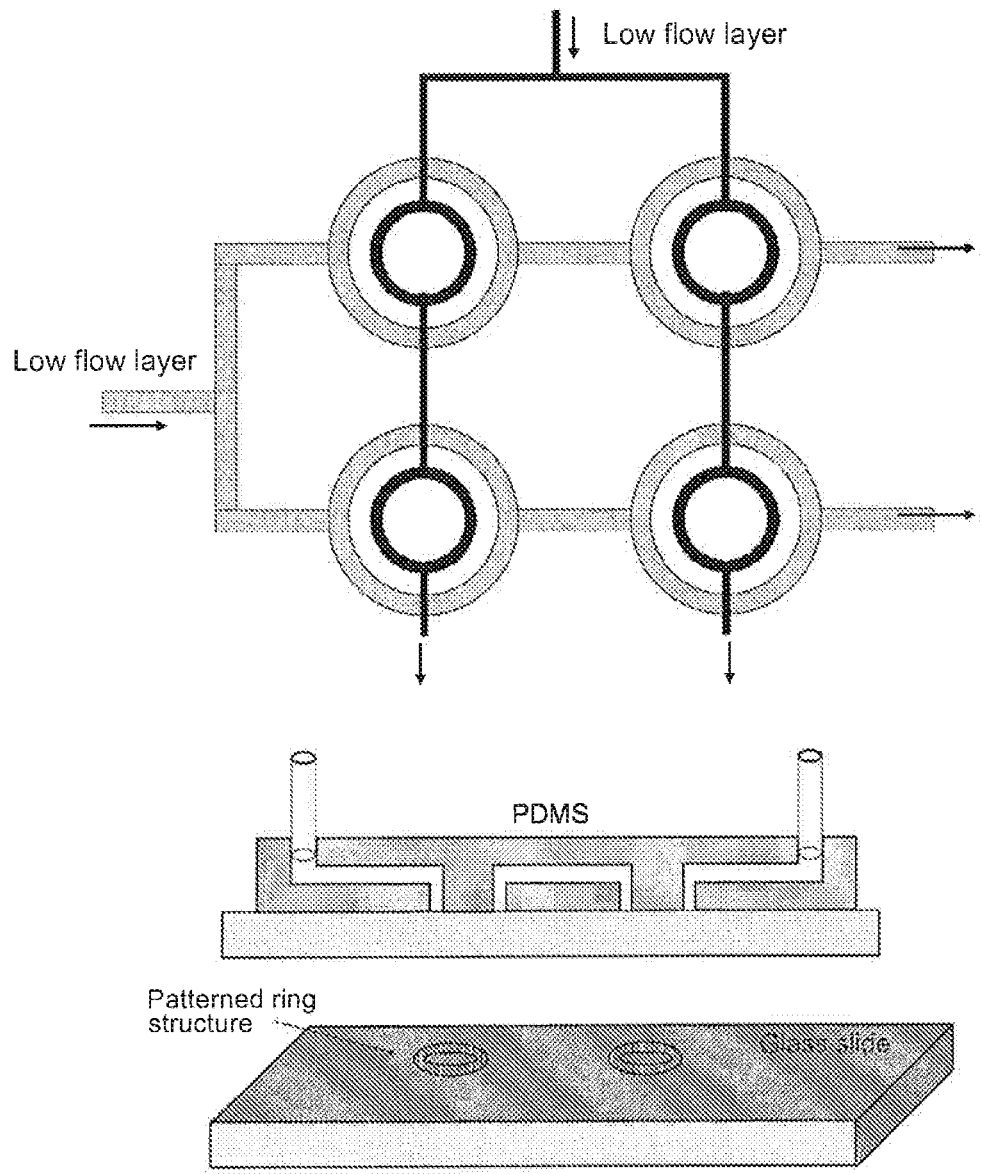
FIG. 5 shows a schematic representation of the method to manufacture a patterned substrate, using a multi-layer fluidic channel device according to an embodiment herein disclosed.

In some embodiments, the molded polymer can then be coupled and in particular bonded onto a support, such as a glass surface, which provides the floor for the channels of barcoded pattern. An exemplary illustration of a design two-layer PDMS fluidic channel device used for creating a multiple ring pattern (bull's eye) on a glass slide is shown in FIG. 5.

In some of embodiments, the substrate can be pre-coated with a material of interest. For example in embodiments wherein a barcode is manufacture using the DEAL technology further illustrate below, a polyamine polymer or poly-L-lysine polymer (Sigma-Aldrich), can be pre-coated prior to bonding to increase DNA loading of the final barcoded pattern (see below and in particular Example 2).

The number of microfluidic channels determines the size of the barcode array. In some exemplary embodiments the barcoded array comprises 13 to 20 parallel microchannels that wind back and forth to cover a large area (3 cm×2 cm) of the support with the DNA barcode microarray.

In some embodiments, patterning can be performed by contacting the capture agent or molecule of choice on the support for a time and under conditions to allow attachment on the support. More particularly, in some embodiments patterning can be performed by providing solutions, each containing the molecule of choice (e.g. a different strand of primary DNA oligomers prepared in 1×PBS buffer in embodiments wherein the array is coupled with DEAL technology), can be flowed into each of the microfluidic channels. Then, the solvent of the solution can be allowed to evaporate, e.g. by placing the solution-filled chip in a dessicator to allow solvent (e.g. water) to evaporate completely through the gas-permeable PDMS, leaving the molecules to be attached (e.g. DNA molecules) behind. In some embodiments, this process can take from several hours to overnight to complete.

Following patterning of the molecules, the mold is usually decoupled from the support. In some embodiments, once the mold is removed from the support the patterned molecule can be subjected to subsequent treatments (e.g. DNA molecule can be fixed to the glass surface by thermal treatment at 80 C for 4 hours, or by UV crosslinking; removal of salts or other precipitates that might have formed during one or more of the previous operations which can be removed, for example, by rapidly dipping the slide in deionized water prior to bonding the blood-assay chip to the slide). An exemplary procedure of the patterning method herein disclosed is illustrated in Example 15.

In particular, in some specific embodiments, a series of microfluidics channels is patterned into PDMS, and those channels bonded onto a glass surface so that one out of the 4 channel walls is the glass surface itself. The numbers of micro fluidics channels determines the size of the barcoded array. In this way, a solution flowing through the micro fluidics channel will come into contact with the glass substrate. Typical dimensions of these micro fluidics channels for barcoded used for biological assays are 10 micrometers or larger. In particular, in embodiments where material is patterned to be subjected to a bio assay, the channel width defines the width of an individual bio-assay measurement area within the final bar code. In those embodiments, if the final measurement of the biomolecule is done using optical methods, then a 10 micrometer wide area constitutes a size that is readily imaged using low-cost optics. Larger and smaller bars are also possible.

A different material and in particular a different biological species (or a different concentration of the same biological species), such as DNA oligomers, can then be flowed in to each of the individual micro fluidics channels.

The biological species or other patterned material can then be attached to the glass surface areas within those microfluidics channels using electrostatic or other chemical interactions. The glass may be pre-coated with some molecular component to increase the chemical interaction between the biological species and the glass surface (see above and below in particular Example 2).

The solvent from the solution containing the patterned material (e.g. the biological species) is then removed. If that solution is water and the fluidics (e.g. microfluidics) is fabricated from PDMS, then the water can be let naturally evaporate through the PDMS, leaving the patterned material attached to the substrate thus providing a the patterned array on the substrate. In some embodiments, it may be desirable to introduce additional channel (e.g. micro fluidics channels) at this point for handling and introducing the biological sample of interest.

The microfluidic bar-code patterning chip may be made by molding silicon elastomer from a master template. The master template may be fabricated from many materials. One method is to fabricate the master by using photolithography to expose an SU8 2015 photoresist. Regions of the photoresist are removed following lithographic exposure, and the remaining material constitutes the master. Alternatively, photolithographic patterning methods, coupled with deep reactive ion etching (DRIE), can be utilized to prepare a master from a silicon wafer. These various methods for preparing microfluidics molds and microfluidics channels from those molds are well known in the art. (Gael Thuillier and Chantal Khan Malek, *Microsys. Technol* 12, 180, 2005.)

The patterned material can comprise any substance of interest suitable to be attached to a support, including organic or inorganic substances, Exemplary inorganic material that can be patterned using the patterning methods and systems herein disclosed include but are not limited to gold nanoparticles that can attach to thiol functionalized substrate surface, iron oxide nanoparticles that can be deposited onto the substrate using magnetic field, and silica particles that can be immobilized by cationic polymer coated substrate, and so on.

Exemplary organic that can be patterned using the patterning methods and systems herein disclosed include but are not limited to living species and their mixtures such as cells, virus, bacteria and fungi, complex biospecimens and their mixtures such as tissue, tissue lysate, cell lysate, serum, saliva and joint fluid, monotypic molecule and their mixtures such as polynucleotides, proteins, antibodies, glycoproteins, polysaccharides, lipopolysaccharides, ligands, peptides, polypeptides, lipids, drugs, drug candidates, antigens and the fragments, potions, and components or any of above. The organic materials can also include non-biological materials such as polymers, oligomers, dye molecules, conducting polymers, responsive polymer, gas sensing polymers, liquid crystals and metal organic frameworks (MOFs), carbon nanotube, fullerene, grapheme, and their nano/microstructures. In some embodiments, the patterned material comprises capture agents. In some embodiments, the patterned material comprises detectable targets. In other embodiments, the patterned material comprises a material, such as cells or other biological material to be assayed. In other embodiments, the patterned material can comprise other organic or inorganic substance for which the barcoded configuration is desired (e.g. liquid crystal for LCD manufacturing, or gas selective polymers to be used as gas sensors).

According to the patterning methods and systems herein disclosed, a pattern and in particular a barcoded pattern or array can be created on very small area and patterning of magnetic ID or other material can therefore be performed onto small-sized products.

In some embodiments, wherein the pattern is used for the detection through capture agents, the capture agent is formed by a polynucleotide and in particular a DNA polynucleotide, that bind about 10 to 20 consecutive bases of a target RNA via complementary hybridization. In some of those embodiments the arrays, substrates, methods and systems herein disclosed can be used to detect messenger RNA (mRNA) and in particular mRNA from a biospecimen (e.g. tissue lysate). In some of those embodiments, another labeled DNA stand (e.g. fluorescently labeled) is designed to bind to ~10-20 different bases of the captured mRNA for signal read out. In some embodiments, a multiplexed measurement of a panel of mRNA molecules can be performed on a barcode array patterned with stripes of their capture agent DNA.

In some embodiments, wherein the pattern is used for the detection, the target is a microRNA (miRNA) a type of short RNA molecules (22 bases) that regulate gene expression at the post-transcription level In some embodiments, wherein the pattern is used for detection, the target can be a transcription factor, and the capture agent is a polynucleotide and in particular a DNA polynucleotide having the same sequence of the binding site of the transcription factor, or a portion thereof or an homologous sequence thereof. In some embodiments, fluorescence-labeled or biotin-labeled antibodies are then used for signal readout.

In some embodiments, the lines are formed by one or more channels configured to host the material to be patterned. In particular, in some embodiments the fluidic channel width can be made ranging from 0.5 µm to 1 cm. The height can be typically >$\frac{1}{10}$ of the channel width when a soft materials such as PDMS is employed, and can be less if a harder material (e.g. glass, silicon, polystyrene, PMMA, polycarbonate or epoxy) is used to make the fluidic channels.

In embodiments when a two-layer device is used for patterning arrays, the channel can be as short as 1 mm and up to meters when the channel is shaped to cover the entire substrate (e.g. a glass slide 1"×3") for example by turning back and forth on the substrate. In embodiments where a larger substrate is used, the channel length can be longer since the length is defined by the substrate and the application of interest.

Figure 6:
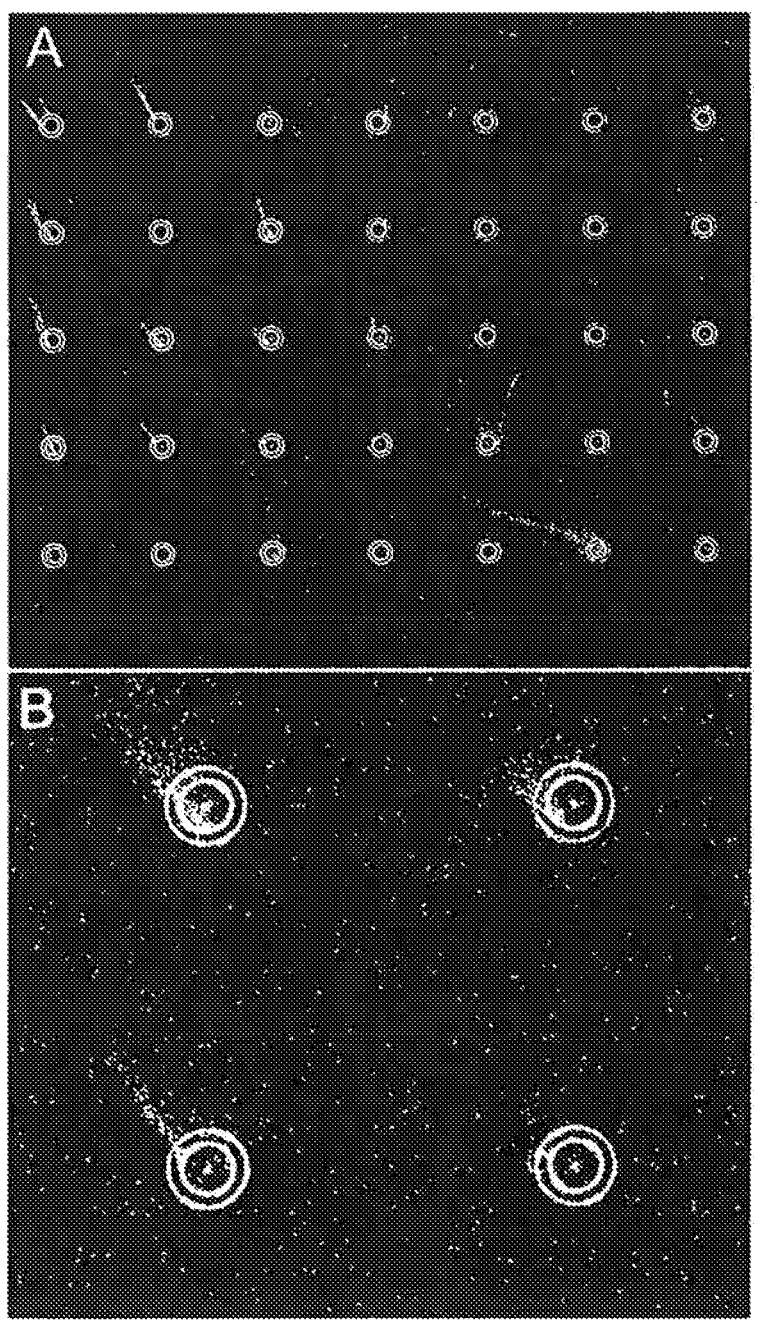
FIG. 6 shows an exemplary array according to an embodiment herein disclosed.

The array can be in principle made into any custom-designed shapes such as stripes, rings, concentric rings (see for example the illustration of FIGS. 5 and 6), triangles, rectangles, polyhedrons, stars, cross-bars, letters, pictures on flat, convex, concaved or irregular substrates. In particular in FIG. 6 a multiple ring pattern suitable to application such as a bio-assay for detection of targets secreted by a sample such as a cell placed in the middle, is shown. In particular the images of FIG. 6 show the detection of proteins IL-2 and TNF-α visualized by Cy3 and Cy5 fluorescent probes.

Figure 7:
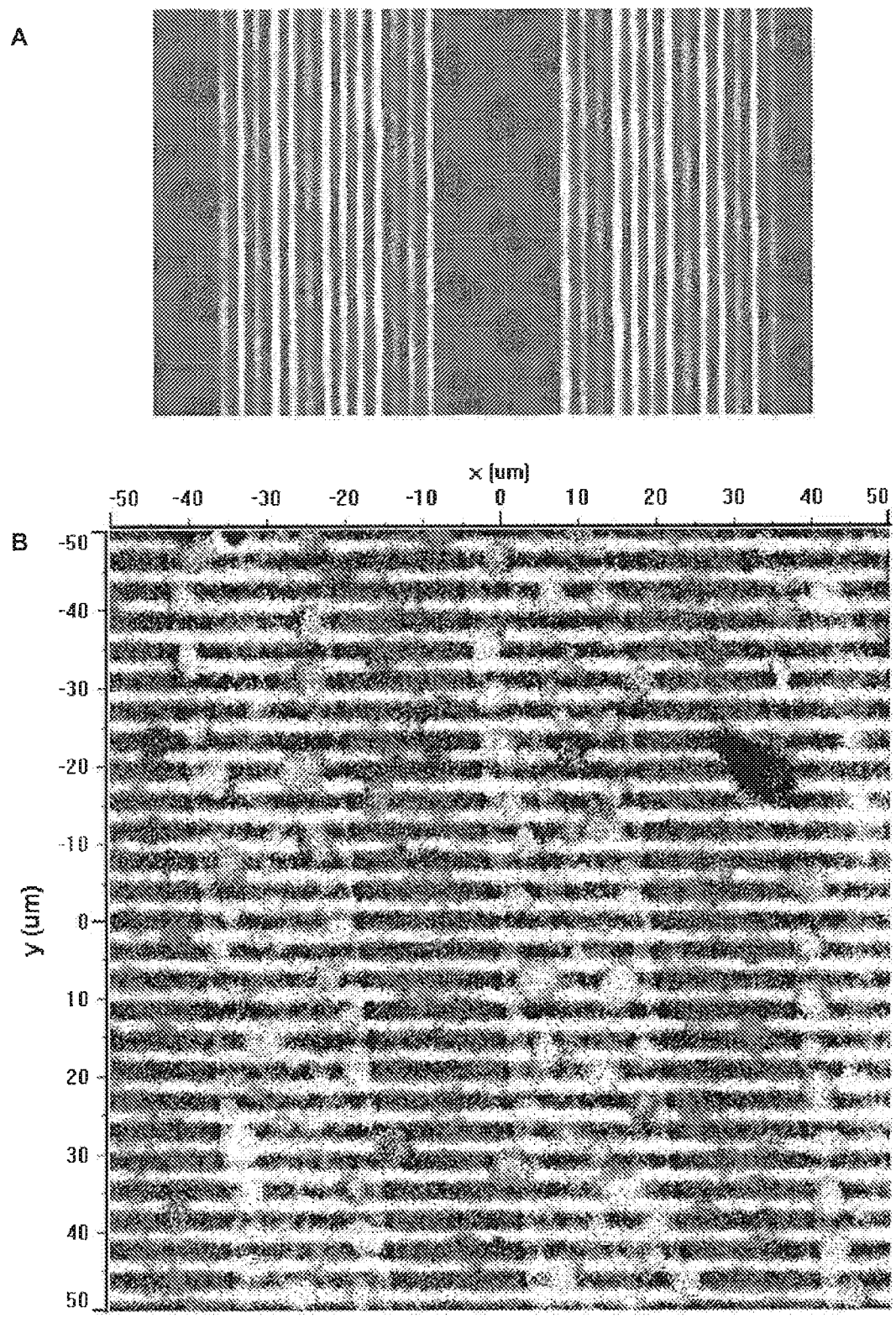
FIG. 7 shows two images corresponding to an exemplary molecular detection using a 20 µm barcoded array (panel A) and a 2 µm barcoded array (panel B) according to an embodiment herein disclosed.

In embodiments, wherein the channels are used to pattern polynucleotides (e.g. DNA) or proteins (e.g. antibodies), the channels width can be anywhere from 0.5 µm to 1 cm and the height can range from 1 µm to 1 cm, and the length can any that is allowed by the area of the given substrate. An exemplary 2-μm barcode array is shown in FIG. 7, wherein a barcoded array of fluorescent DNA molecules manufactured according to the teaching of the present disclosure, is illustrated. For optimum demonstrated performance of polynucleotide detection using a complementary DNA barcoded array, a channel width of 20 μm and a height of 20 μm are preferred when a 200-μM capture DNA solution is used and the developed array is visualized using fluorescence scanner. In embodiments, wherein a DNA barcoded array is used to immobilize DNA encoded antibodies and subsequent immuno-sandwich assay, the same channel width and height are preferred (see below description of DEAL technology).

Figure 8:
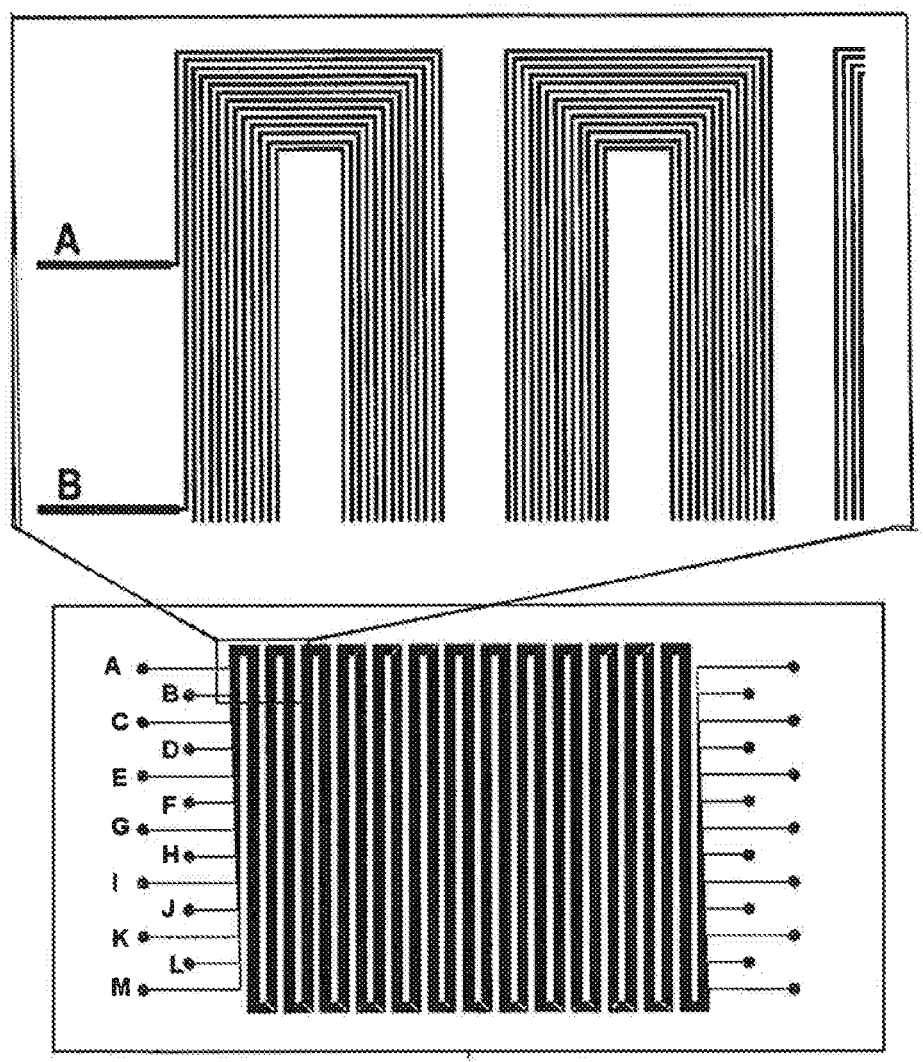
FIG. 8 shows a computer-aided design of the barcode array according to an embodiment herein disclosed and a related use. The panel on the bottom shows thirteen different capture agents (A-M) flowed into a set of parallel fluidic channels each channel having a width of 20 µm. The top panel is the enlarged view of a selected area.

In some embodiments, some or all of the substantially parallel lines are connected to one another through at least one of the ends. More particularly, in applications wherein the lines are formed by channels the substantially parallel lines can be connected to one another to form a single channels configured in a serpentine-like shape. Serpentine-like channels allow the fabrication of repeated barcode arrays over a large area, e.g. the entire glass slide (1"×3"), in a single step of flowing capture agents. It represents a significant advantage in large-scale, low cost manufacture of barcoded arrays for detection applications. In addition, it allows an assay to be executed in multiple repeats at the same thus reduce the statistic errors. An exemplary illustration of a serpentine-like channel is shown in FIG. 8. Additional connections between the substantially parallel lines of a pattern or multiple patterns (for example multiple barcoded patterns connected to form a pyramid to increase DNA loading in application wherein barcode is manufactured in connection with DEAL technology).

The material to be patterned can be disposed along the parallel lines according to a specific experimental design of choice. For example, in embodiments where a plurality of capture agents are patterned, the capture agents can be disposed with each capture agent disposed along one line, or with two or more capture agents located disposed along portions of a single channel. In other embodiments, the material to be tested (and in particular detected) can be patterned along one line or portion of a line of the barcode. Exemplary illustrations of those embodiments are shown in FIGS. 1 and 7.

In some embodiments, the patterned material can be used for target detection. In those embodiments, typically capture agents are patterned on the substrate, to form detectable capture agent target complexes. In other embodiments, detectable targets are patterned directly on the material. For example, a number of serum samples from multiple patients can be patterned into a barcoded array. In such array, each stripe contains the biomolecules in the entire plasma proteome of that patient. This array can be exploited to screen for antibodies, ligands, drug candidates, and comparison of biological profiles among patients. Those embodiments are exemplified for the barcoded arrays, substrates, methods and systems of Examples 3-14 and illustrated in the related figures and further described below.

Figure 9:
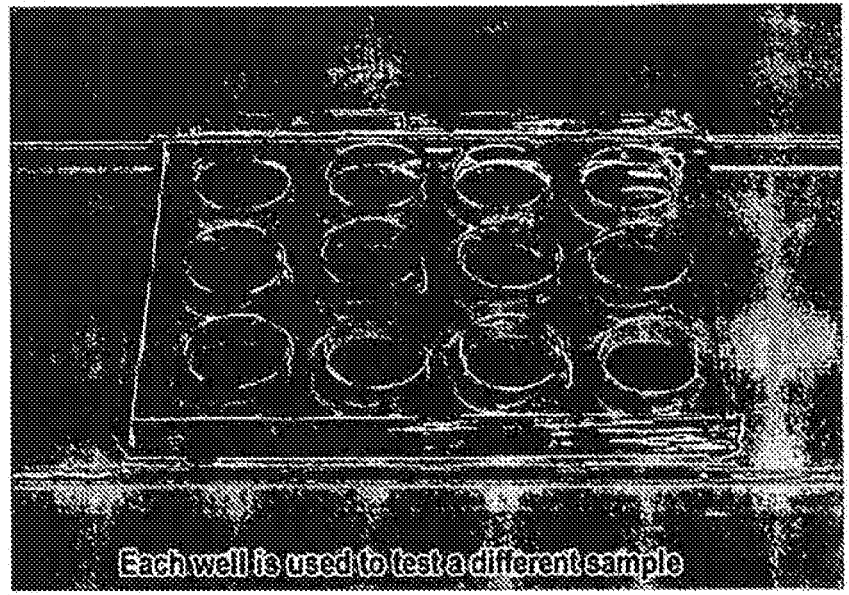
FIG. 9 shows the execution of multiple assays in twelve isolated wells using a barcoded array according to an embodiment herein disclosed. Panel A shows a barcoded array manufactured on a supporting glass slide. Panel B shows protein detection from the array of Panel A visualized by fluorescence imaging.
Figure 9:
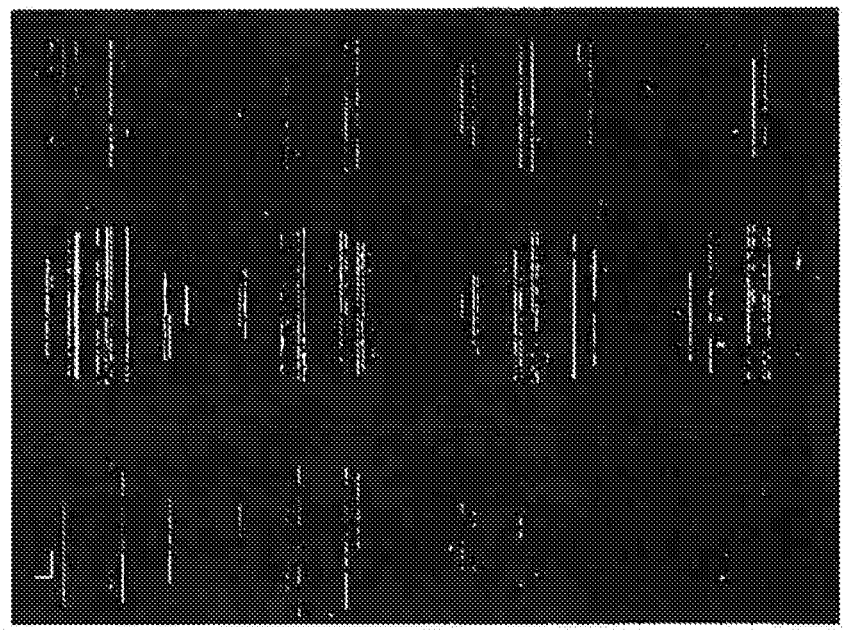

In some embodiments, assays are performed in a non-microfluidic environment. An exemplary illustration of those embodiments is shown in FIG. 9, wherein execution of multiple assays in twelve isolated wells using a barcoded array is illustrated. In particular, the barcoded array illustrated in FIG. 9 is manufactured on a supporting glass slide including wells, wherein. each well contains a different sample such as human serum. In the experiments illustrated in FIG. 9, protein detection from the different samples is visualized by fluorescence imaging.

In some embodiment, assays are performed in microfluidics which allows handling particularly small amounts of biospecimens (such as a finger prick of blood, tissue from skinny needle biopsy, etc).

In some embodiments, the barcode array can be used to detect multiple proteins and/or genes from a single cell via on-chip single cell culture, lysis, mRNA and protein isolation/purification, in particular using an integrated microfluidic device such as the one described in the U.S. Application entitled "Microfluidic Devices, Methods and Systems for Detecting Target Molecules" Ser. No. 11/164,737 filed on Jul. 16, 2008, incorporated herein by reference in its entirety.

A further description of the arrays, substrates, devices methods and systems of the present disclosure is provided with reference to microfluidic applications wherein the sample is a material of biological origin (bio sample) and the targets are biomarkers. A person skilled in the art will appreciate the applicability of the features described in detail for microfluidics and biomarkers for non-microfluidic applications and/or for other biologic, organic and inorganic samples and targets.

In some embodiments, the arrays, devices methods and systems herein disclosed can be used to perform a surface bound bioassay based on detection a biomolecule of interest in some biomaterial, such as blood, serum, biological tissue, or as a component of a cell culture (herein also indicated as bio-barcode assay).

The biological material can be pretreated so as to release the biomolecules of interest, to remove biological material that can interfere with binding of the biomolecules in the surface bound bioassay. An exemplary pretreatment procedure includes separating blood cells from blood plasma (or serum), and then measuring the proteins from the plasma. In other procedures the separated cells could be further separated into white and red blood cells, which can be therefore subjected to further analysis. An exemplary surface bound bioassay can be carried out as follows: The biomolecule of interest is bound to a (primary or 1°) surface-bound capture agent molecule (e.g. an antibody or complementary single-stranded DNA oligomer) that specifically recognizes and binds to the biomolecule of interest. Typically, a secondary (or 2°) capture agent containing some label for detection, such as a fluorescent molecule, is introduced to bind to the surface-bound biomolecule.

Figure 10:
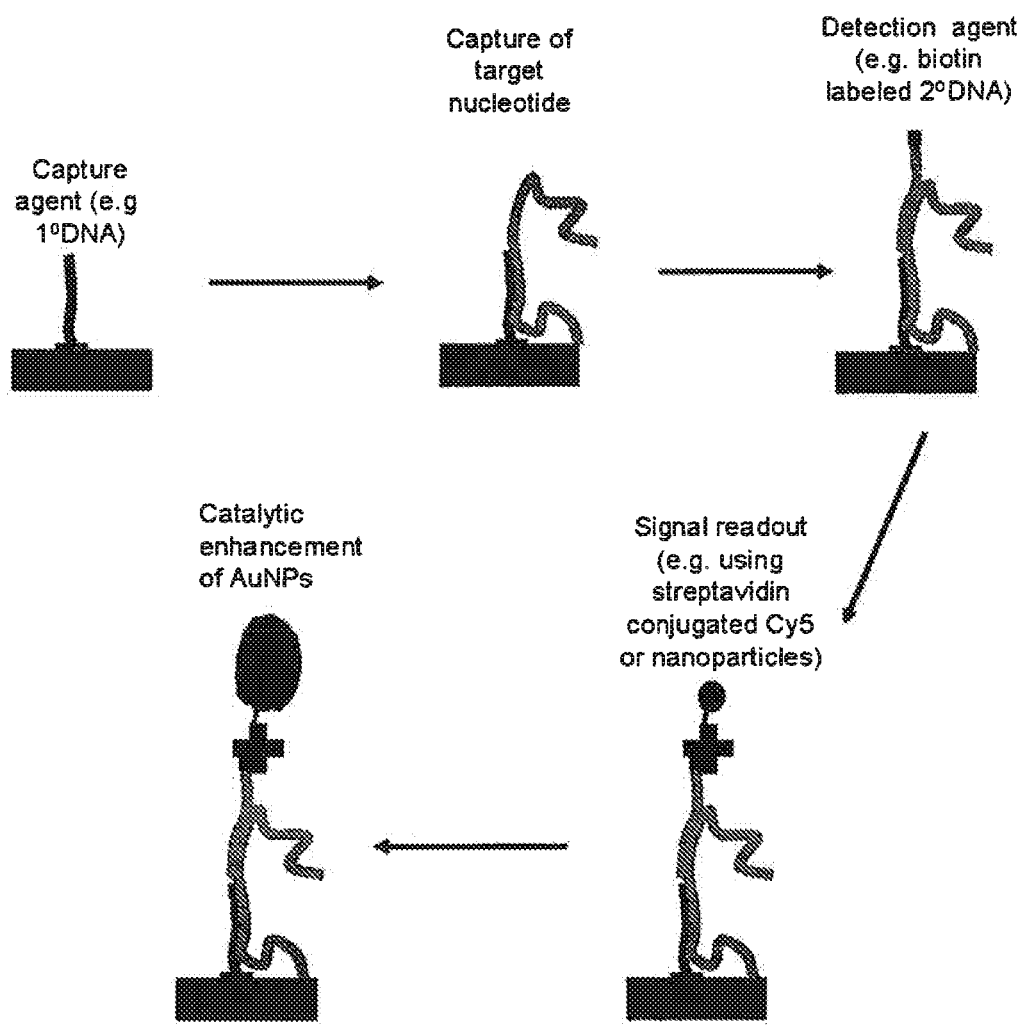
FIG. 10 shows a schematic representation of the method to detect target molecules using a group of distinct capture agents that are directly patterned into a barcoded array according to an embodiment herein disclosed.
Figure 11:
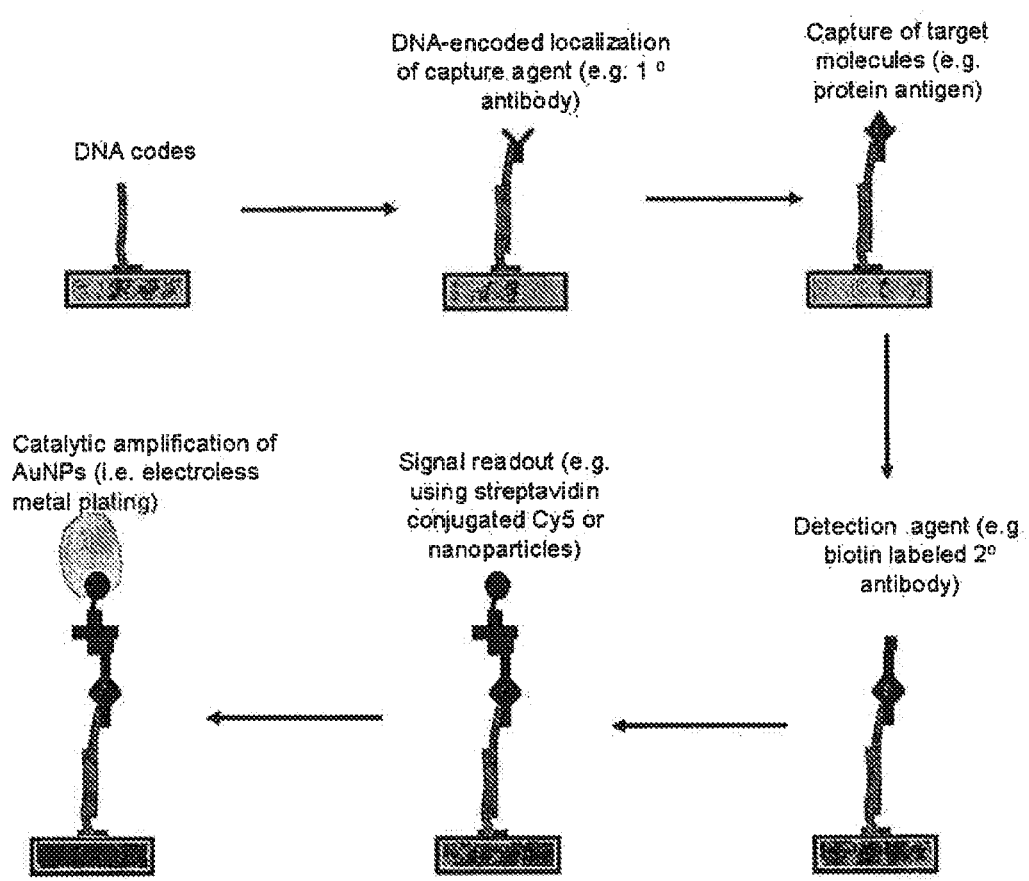
FIG. 11 shows a schematic representation of the method to detect target molecules using a group of distinct capture agents that are immobilized onto the specific location of a pre-determined barcoded array via a set of linkers according to an embodiment herein disclosed. This is exemplified by the detection of target antigen using captured antibodies encoded by a set of complementary DNA molecules.

The bio-barcode can be manufactured patterning the capture agents of choice on a substrate along substantially parallel lines. In certain microfluidic applications the substantially parallel lines can be formed by channels or channel portions. Exemplary illustration of different embodiments wherein capture agents are attached to a surface in a bio-barcode are shown in FIG. 10 (capture agents DNA molecules for detection of polynucleotide (e.g. mRNA and microRNA) to be configured in a barcoded array), FIG. 11 (DNA-encoding antibodies to enable immuno-sandwich assay on barcode array allowing detection of proteins, cell surface markers, glycoproteins, virus and bacteria in multiplex) and FIG. 12 (schematic illustration showing how increased DNA loading helps to enhance detection sensitivity in application wherein the bio-barcode is coupled with DEAL technology see below).

Patterning of capture agents, for example, antibody arrays for detecting proteins or complementary DNA arrays for detecting polynucleotides, results in an increased sensitivity of molecules such as polynucleotide, nucleic acid (mRNA, miRNA, DNA etc), An increased sensitivity could be in particular associated with two factors: (1) the increased loading of capture DNA using poly-amine to coat substrate surface (for embodiments wherein the capture agent is a polynucleotide and in particular DNA) and (2) the reduced feature size with respect to conventional pin spotted arrays (e.g. 20 µm in barcoded array vs. 200 µm in conventional pin-spotted array) lowers the diffusion barrier and leads to high binding efficiency.

In some embodiments the capture agents include one ore more component. In particular, in some embodiments the capture agents can be formed by a substrate polynucleotide and a polynucleotide encoded-protein in application of the technology (herein also identified as DEAL) described in U.S. patent application Ser. No. 11/888,502 herein incorporated by reference in its entirety.

Accordingly, the wording "substrate polynucleotide" as used herein refers to a polynucleotide that is attached to a substrate so to maintain the ability to bind to its complementary polynucleotide. A substrate polynucleotide can be in particular comprised of a sequence that specifically binds and is thereby defined as complementary with an encoding-polynucleotide of a polynucleotide encoded protein.

The wording "polynucleotide-encoded protein" refers to a polynucleotide-protein complex comprising a protein component that specifically binds to, and is thereby defined as complementary to, a target and an encoding polynucleotide attached to the protein component. In some embodiments, the encoding polynucleotide attached to the protein is protein-specific. Those embodiments can be used to perform assays that exploit the protein-specific interaction to detect other proteins, cytokines, chemokines, small molecules, DNA, RNA, lipids, etc., whenever a target is known, and sensitive detection of that target is required. The term "polynucleotide-encoded antibody" as used herein refers to a polynucleotide-encoded protein wherein the protein component is an antibody.

In the polynucleotide-encoded proteins herein disclosed each protein specifically binds to, and is thereby defined as complementary to, a pre-determined target, and each encoding polynucleotide-specifically binds to, and is thereby defined as complementary to, a pre-determined substrate polynucleotide.

Figure 12:
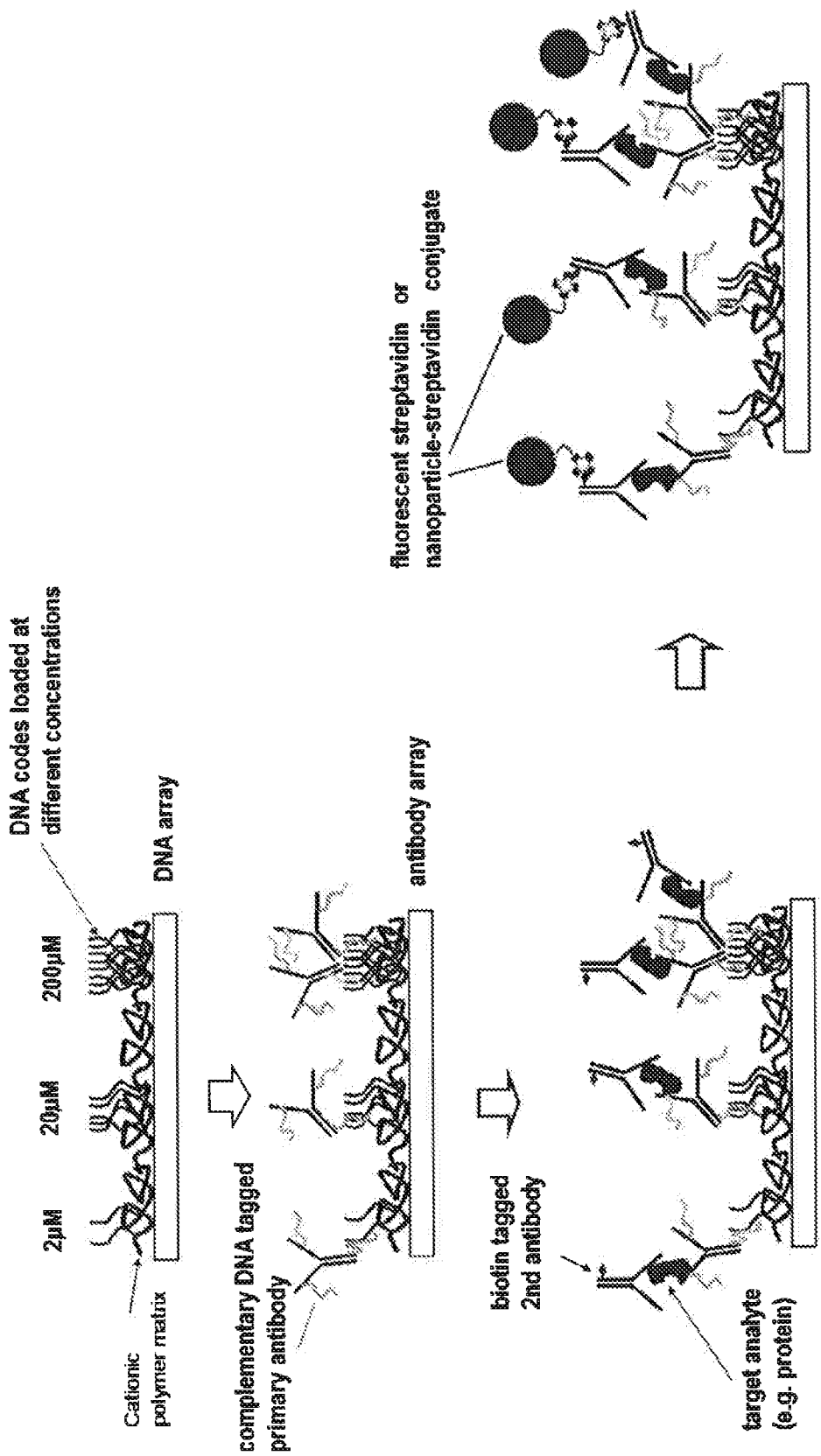
FIG. 12 shows a schematic representation of the method to vary the loading of capture agents and consequently the sensitivity and concentration range for the detection of targets using a barcoded array according to an embodiment herein disclosed.

In embodiments wherein the protein is an antibody, the protein-target interaction is an antibody-antigen interaction. In embodiments wherein the protein is other than an antibody, the interaction can be receptor-ligand, enzyme-substrate and additional protein-protein interactions identifiable by a skilled person upon reading of the present disclosure. For example, in embodiments where the protein is streptavidin, the protein-target interaction is a receptor-ligand interaction, where the receptor is streptavidin and the ligand is biotin, free or attached to any biomolecules. An exemplary schematic illustration is shown in FIG. 12.

When coupled with the DEAL technique, the amount of polynucleotides that is deposited onto a given spatial location within the bio-barcode array can be controlled in view of the desired sensitivity and concentration range over which the biomolecule of interest can be detected. By using two or more stripes within the same bio-barcode array, each optimized to detect the same biomolecule but over different concentration ranges, the concentration range over which that protein can be detected, as compared to a conventional assay, can be dramatically increased.

The concentration range of DNA detectable with a Bio-Barcode array coupled with DEAL can be as low as 1 pM to 100 nM using 200 µM loading of capture DNA on 20 µm barcode stripes. Target molecules suitable for this technique include messenger RNAs, micro RNAs, the fragments of genomic DNAs, viral DNA, bacterial DNA, and synthesized polynucleotides.

Some embodiments wherein the Bio-Barcode is coupled with DEAL shows an increased sensitivity if compared with embodiments wherein protein capture agents are patterned directly on a substrate. In particular, in some embodiments wherein antibodies are patterned directly into barcoded array with fabrication methods that require application of high temperatures when the antibodies are attached to the substrate, all the target molecules that can be detected by DEAL are in principle detectable, but a lower sensitivity might be seen due to the poor stability of the antibody in a dry state.

When coupled with the DEAL technique, the bio-barcode array withstands the processing conditions associated with micro fluidics chip fabrication. As a consequence, the Bio Bar. Bar Code array can be advantageously manufactured as illustrated in the exemplary procedure outlined below with reference to an exemplary array including 10 antibodies used as capture agents (10 CAs) labeled with single stranded DNA used as encoding polynucleotide.

The 10 antibodies against the biomarker of interest are chemically labeled with single-stranded DNA (ssDNA) oligomers. The complementary ssDNA' oligomers can be deposited onto regions of a surface. DNA hybridization assembles the 10 CAs to those particular regions.

The 10 CAs are patterned using microfluidics channels. The channel widths and densities are limited by what can be patterned—smaller channels and higher densities than are practical using other methods are readily achieved. Typically channels of widths of at least 10 micrometers, spaced by distances of at least 50 micrometers, are most practical for typical bioassays, such as analyzing multiple proteins from serum. This allows for large numbers of measurements to be carried out in a relatively small microfluidics channel.

Spot sizes significantly smaller than 10 micrometers are also possible with this technique, as are significantly higher spot densities. These may be useful for more specialized applications, such as would be required for measuring a panel of protein biomarkers and other biomolecules from circulating tumor cells, cancer stem cells, and other extremely rare cell types.

The bio-barcode patterned microfluidics channels are readily aligned with other microfluidics channels, such as are used for the handling of the biological specimen from which the assays are performed. For example, alignment markers that are utilized to align the bio-barcode micro fluidics channels can also be utilized to assemble the microfluidics channels for handling the biological sample. This is standard fabrication practice.

The density of 1° CAs that can be deposited onto such a small spot can be significantly higher than what can be achieved using spotting methods. Repeated depositions of 10 CAs through the same microfluidics channels can achieve a very high surface loading of the 10 CAs. Conversely, the DEAL technique utilizes single-stranded DNA (ssDNA) oligomers as capture agents for the 10 CA antibodies that are, in turn, utilized to detect proteins. The DNA can be loaded at very high levels using the bio-barcode Array because of the high solubility of DNA in water. This, in turn, can lead to very high coverage of the 1° antibody CAs.

Multiple numbers and classes of capture agents can be placed on specific, microscopic locations on a surface using microfluidic patterning of the 10 capture agents. In this way, the panel of biomolecules is detected by detecting labeling signals (for example, fluorescence) from the region of the surface where the pattern of 10 capture agents was placed.

In some embodiments, wherein the arrays, substrates methods and systems herein disclosed are performed in microfluidics, the capture agents can be attached on the location with a method to attach molecule along a predetermined pattern herein disclosed. In those embodiments, using a microchannel-guided flow-patterning approach, a barcode arrays can be manufactured that are at least an order of magnitude denser than conventional microarrays. In some embodiments, this result can be accomplished by creating a mold, e.g. a polydimethylsiloxane (PDMS) mold containing the desired number of microfluidic channels, e.g. 13-20 parallel microfluidic channels, with each channel conveying a different biomolecule capture agent. A skilled person will understand that the number of channels can readily be expanded to include 100 or more different capture agents; whereas in microcontact printing, the patterning difficulty increases exponentially as the number of proteins printed is increased, due to the challenges of aligning multiple stamps to print multiple proteins.

In some embodiments, the barcoded array is a DEAL barcoded array. In some of those embodiments poly-amine coated glass surfaces can be use to allow significantly higher DNA loading than do more traditional aminated surfaces. DNA "bars" of 2 micrometers in width could be successfully patterned. In some exemplary embodiments, described herein an about 20-micrometer (μm) channel width was chosen because the fluorescence microarray scanner has a resolution of 5 μm.

In those embodiments a 10-fold increase in array density is achieved as compared to a typical pin-spotted DNA array (i.e. 150 μm spot diameters at 300 μm pitch), and greatly expands the numbers of proteins that can be measured within a microfluidic chip disclosed herein for a given sample size. In particular, in some embodiments, simultaneous detection of 12 to 20, up to 50 or even more than 50 proteins. This feature can be used in applications where detection of multiple targets is desired, for example detection of a biological profiles but also a variety of waste gases (e.g. from car engine exhaustion) or pollutes in a sample.

The protein assay can be carried out on the 10 CAs array as described above. Use of DNA hybridization as an assembly strategy allows for multiple proteins to be detected within the same microenvironment, since the various 10 CA antibodies for the various proteins to be detected can be each labeled with a different ssDNA oligomer. Also use of DNA hybridization as an assembly strategy allows preparation of the substrate including ssDNA in early in the fabrication process so that a substrate including the ssDNA can be treated, dried out, heated, shipped and provided to the final user in a ready to use systems that also include complementary capture agents. Exemplary applications are described in Examples 1 to 7 and in the related figures describe the bar-code array patterning technique and DEAL bar-code chips for protein detection.

A person skilled in the art would understand that the array herein disclosed can include patterning a variety of biological materials, e.g. DNA, proteins, sera and tissue lysates, using micro fluidic channels. The Bio Bar-code Array method can be applied to the fabrication of bio-chips and integrated biosensing devices for high-density, multiplexed and sensitive detection of DNA and proteins in clinic diagnostics of human diseases like cancers, and for high-throughput drug screening. In some embodiments the patterning is based upon a new, yet simple and reliable approach—micro channel guided surface patterning of a large number of different biological species to fabricate a small-size, high-density array.

The systems herein disclosed can be provided in the form of arrays or kits of parts. An array sometimes referred to as a "microarray" includes any one, two or three dimensional arrangement of addressable regions bearing a particular molecule associated to that region. Usually the characteristic feature size for microarrays is micrometers.

In a kit of parts, various components can be comprised in the kit independently. In some embodiments, a patterned substrate can be provided together with a label and/or other reagents suitable to perform detection. In some embodiments, a device suitable for detecting the pattern can also be included.

In embodiments, wherein the patterned substrate is integrated with deal technology a system can include polynucleotide-encoded proteins and a patterned substrate comprised in the kit independently. Molecules comprised in the kit (e.g. the polynucleotide-encoded protein) can in particular be included in one or more compositions, with each molecule in a composition together with a suitable vehicle carrier or auxiliary agent.

The substrate provided in the system can have substrate polynucleotides attached thereto or other molecule attached according to the desired pattern. In some embodiments, the substrate polynucleotides, or the material to be patterned can be further provided as an additional component of the kit. Additional components can include labeled polynucleotides, labeled antibodies, labels, microfluidic chip, reference standards, and additional components identifiable by a skilled person upon reading of the present disclosure. In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Additional applications in which the patterned material is not limited to a biological sample will be identifiable by the person skilled in the art. In particular in some embodiments, the patterned material can be used for magnetic identity (ID) of small-sized products, which can include but are not limited to products carrying a biological material. For example, a magnetic ID bar has been widely used in tracking a product. But conventional magnetic ID pad is too large to be used for a small-sized subject such as a small camera CMOS chip, a fine jewel and a tiny artifact. Those embodiments are exemplified for the barcoded arrays, substrates, methods and systems in Example 15.

Further details concerning the identification of the suitable carrier agent or auxiliary agent of the compositions, and generally manufacturing and packaging of the kit, can be identified by the person skilled in the art upon reading of the present disclosure.

EXAMPLES

The methods and system herein disclosed are further illustrated in the following examples, which are provided by way of illustration and are not intended to be limiting the scope of the present disclosure.

Example 1: Fabrication and Use of a Barcoded Chip with Integrated DEAL Technology A Barcoded chip was fabricated according to the procedure schematically illustrated in FIG. 13 Panel A.

A silicon elastomer (PDMS) stamp was molded from a lithographically patterned silicon master. Then it was thermally bonded onto a poly-amine coated glass slide on which different biomolecule solutions are flowed into the parallel microchannels. Once the solutions evaporate completely, the PDMS stamp is peeled off and the glass side will be baked to create a robust Bio-Bar-code array. The bar-code stripes can be made 2-20 μm in width and spacing, leading to increased array density compare to conventional microarrays. In principle, there is no limit for the number of primary molecules like DNA that can be patterned using this technique. It indeed enables the fabrication of a large-scale, high-density biomolecule array for systems biology and disease diagnostics.

More particularly, a polydimethylsiloxane (PDMS) mold containing 13-20 parallel microfluidic channels, with each channel conveying a different DNA oligomer as DEAL code, was fabricated by soft lithography. The PDMS mold was bonded to a polylysine-coated glass slide via thermal treatment at 80° C. for 2 hours. The polyamine surfaces permit significantly higher DNA loading than do more traditional aminated surfaces. DNA "bars" of 2 micrometers in width have been successfully patterned using this technique. In the present study, a 20-micrometer (μm) channel width was chosen because the fluorescence microarray scanner used by applications has a resolution of 5 μm. Nevertheless, the current design already resulted in a DNA barcode array an order of magnitude denser than conventional microarrays fabricated by pin-spotting. The coding DNA solutions (A-M for the cancer serum test and AA-HH for the finger-prick blood test) prepared in 1×PBS were flowed into individual channels, and then allowed to evaporate completely. Finally, the PDMS was peeled off and the substrate with DNA barcode arrays was baked at 80° C. for 2-4 hours. The DNA solution concentration was ~100 μM in all experiments except in the hCG test, leading to a high loading of ~$6 \times 10^{13}$ molecules/cm$^2$ (assuming 50% was collected onto substrate).

Figure 13:
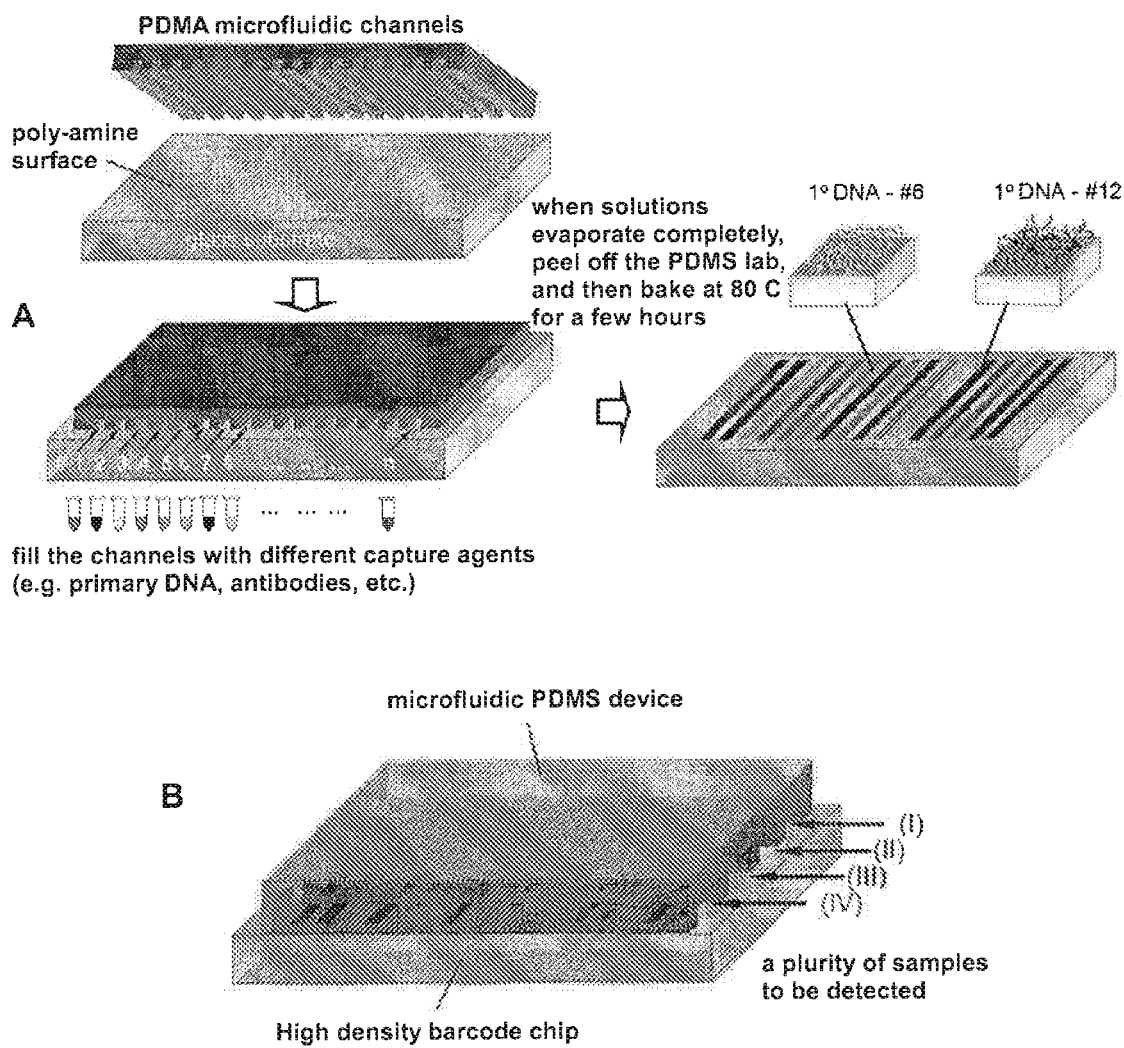
FIG. 13 shows a schematic representation of a method to manufacture a device including a barcoded array according to an embodiment herein disclosed and a related use.

The array so created was used in a bio assay as illustrated in FIG. 13 Panel B. An integrated microfluidic device was placed onto the bio-bar-code chip microfluidic channels. There was no need of fine alignment to integrate the bio-bar-code pattern with the microfluidic systems. Different samples such as patient sera, tissue lysates can be assayed in each microfluidic channels, respectively. The array depicted in FIG. 13 panel B enables high-through biodetection with minimum sample consumption.

The experiments described above can be modified to modulate sensitivity and detectable range of targets according to the experimental design of choice. A possible modification is illustrated in FIG. 8 which shows a schematic illustration of a mask design of a 13-channel patterning chip, wherein the letter A-M indicate the channels for flowing different DNA molecules. Additional modifications include subjecting the array to poly-amine surface modification, e.g. with the procedure exemplified in Example 2 below, to allow increased DNA loading. This modification leads to higher sensitivity and broader dynamic range as illustrate in the exemplary procedure of Example 3 below.

Figure 14:
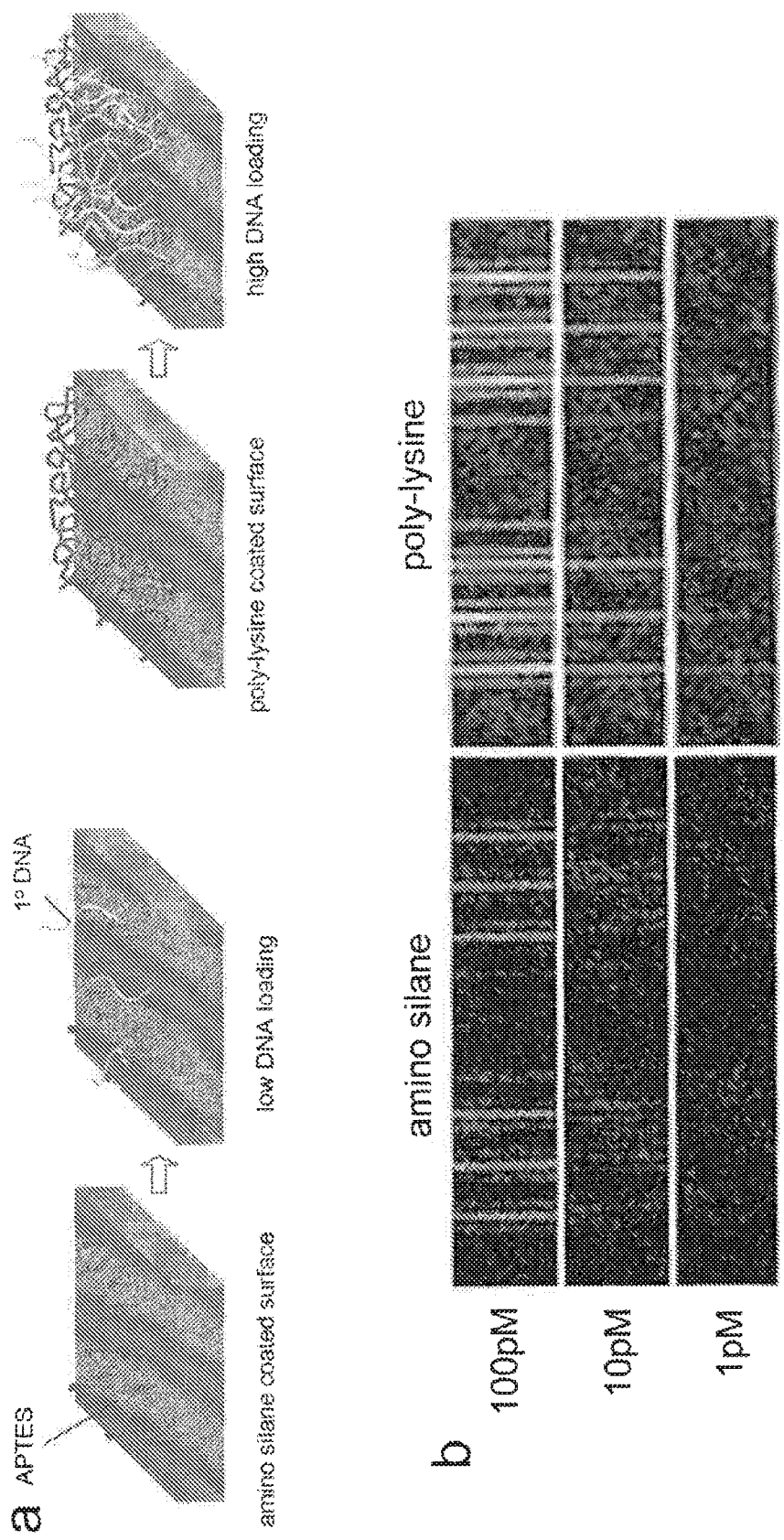
FIG. 14 shows an exemplary detection of protein targets according to an embodiment herein disclosed.

Example 2: Fabrication of a DEAL Barcoded Chip with an Increased DNA Loading During microchannel-guided flow-patterning of the DEAL barcode arrays, the glass surface was modified by treatment with poly-L-lysine (a poly-amine), yielding a three-dimensional matrix for DNA adsorption and markedly increasing the amount of DNA loading The results are illustrated in FIG. 14, which shows the effects of poly-lysine coating on an assay performed with DEAL technology. More particularly, FIG. 14 shows detection of protein targets using the barcoded array manufactured with low and high loading of primary DNA molecules and the resulting difference in the protein detection. As shown in the schematic illustration of panel (a) polylysine coating of the PDMS support results in an increased loading of DNA oligomer codes.

In particular, the DNA-loading density is estimated to be $6 \times 10^{13}$ molecules/cm$^2$ in our experiments, an order of magnitude higher than typical loading densities on amino-silane coated glass slides. As a result, the protein detection sensitivity was improved by an order of magnitude, and the dynamic range was increased to 4 orders of magnitude, as compared with 2-3 orders of magnitude for the small-molecule amine (i.e. amino-propyl-triethoxyl silane, APTES) functionalized glass surface. Exemplary results of this comparative analysis is illustrated in FIG. 14 Panel (b) detection of three human cytokines (IFN-γ, TNF-α, and IL-2) using substrates coated with amino-silane and polylysine, respectively is shown.

Example 3: Barcoded Chip with ELISA-Like Sensitivity

A series of experiments performed by the applicants showed that a barcode chip integrated with DEAL technology renders a high density array for multiplexed protein measurements. Moreover, the DEAL barcoded chip also demonstrates a marked improvement in sensitivity as compared to conventional pin-spotted microarrays.

In particular, a side-by-side comparison study was performed by running DEAL assays on three cytokines under identical conditions. Using the microchannel-guided flow patterning method, a glass slide was patterned with DNA oligomers A, B, C and a blank control O. Each bar was 20 μm in width. The DNA solutions were all 50-100 μM. The pin-spotted array was printed at the Institute for Systems Biology at 100 μM concentration. The typical spot size was 150-200 μm. Six sets of spots were printed corresponding to oligomers A, B, C, D, E, and F. Poly-1-lysine coated slides were used for both types of arrays.

Before the DEAL assay, the capture antibodies were conjugated to DNA oligomer codes as follows: A' to IFN-γ, B' to TNF-α, and C' to IL-2. Protein standards were diluted in 1% BSA/PBS solution at concentrations ranging from 1 fM to 1 nM. The incubation time for each step (blocking, conjugate hybridization, sample binding, detection-antibody binding, and fluorescent-molecule binding) was 30 min. The bar width was 20 μm.

Figure 15:
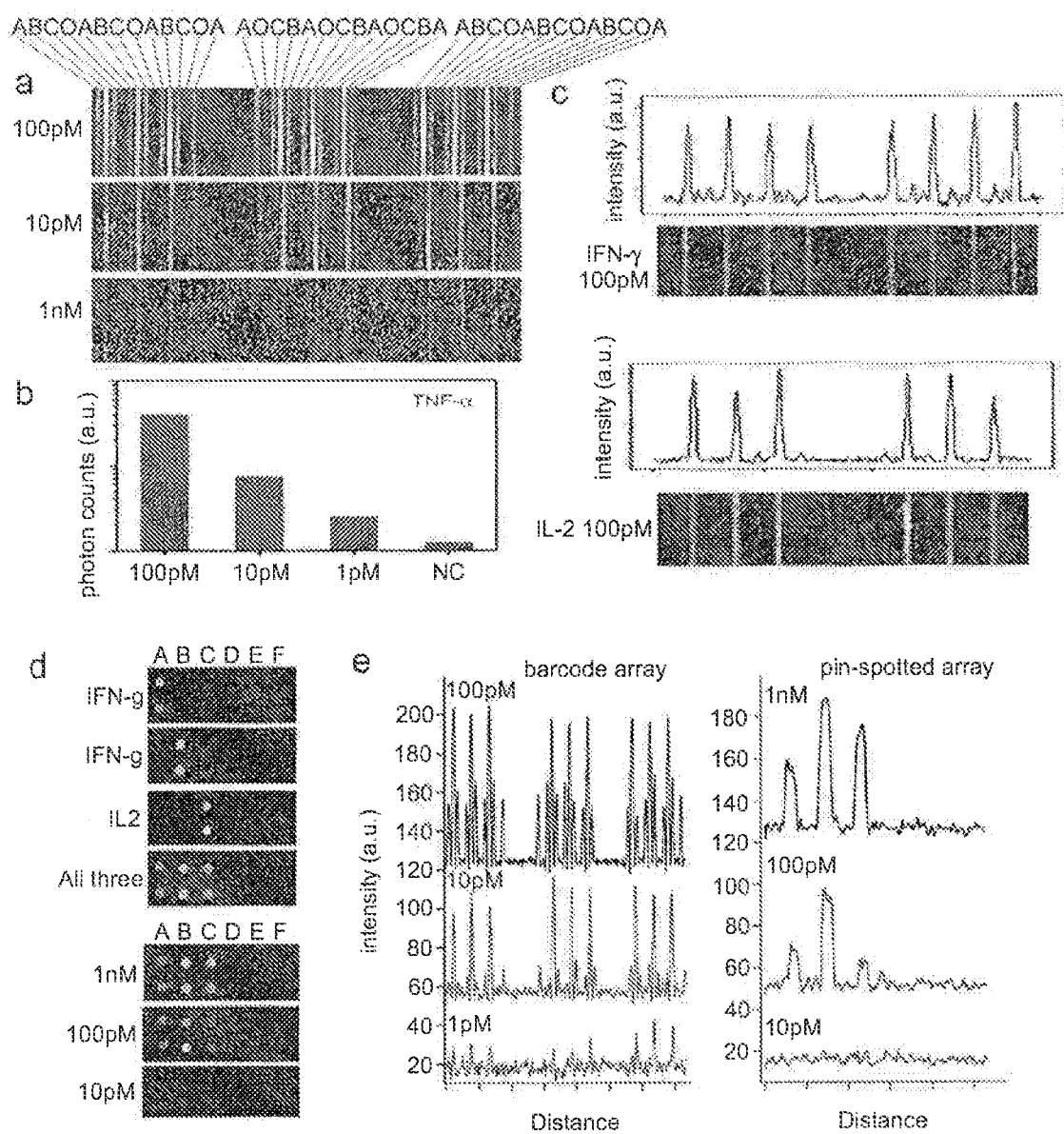
FIG. 15 shows an exemplary protein detection using a barcoded array according to an embodiment herein disclosed and comparison with the protein detection using a conventional pin-spotted array.

The results are illustrated in FIG. 15 wherein immunoassays run on DEAL barcode arrays is shown. In particular, as illustrated in Panel (a) detection of three human cytokines (A: IFN-γ, B: TNF-α, C: IL-2, O: negative control) was proven to be concentration dependent. In the illustration of Panel (a) the bar-code array has a sequence of ABCOAB-COABCOA (herein, "0" denotes that no 1° DNA was flowed in such microchannel). This data show proteins can be detected at concentration as low as 1 pM. Concentration dependence is indicated by the diagram of Panel (b) where quantitation of fluorescence intensity is plotted versus TNF-α concentration. The line profile for the results obtained with 1-pM protein sample as indicated in Panel (a), is shown in the diagrams of Panel (c).

As a further comparison, the sensitivity obtained in ELISA assays (using antibody pairs and protein standards from eBioscience) is projected to be ~10 pg/mL (0.8 pM) for TNF-α. Therefore, those experiments show that the DEAL barcode array combines ELISA-like sensitivity with a high degree of multiplexing for protein measurements.

In addition, the TNF-α detection sensitivity of the DEAL barcode arrays was higher and the projected sensitivity limit was better than 1 pM, as compared to 10-100 pM for conventional microarrays as illustrated in the comparative assay performed under the same condition using a conventional pin-spotting method of Panel (d) further illustrated in the comparative Example 6 below. These results confirmed that the barcoded chip has much higher sensitivity and increased linear range for protein measurements, as compared with a conventional assay.

Example 4: Use of a Barcoded Array for DNA Detection

A barcoded array was used in a bio assay for detection of DNA. In particular, a polynucleotide (DNA) was patterned on a substrate and used to detect a complementary polynucleotide in a sample. The results illustrated in FIG. 16 show that the patterned DNA oligomers exhibit a high affinity for binding their complementary strands.

Figure 16:
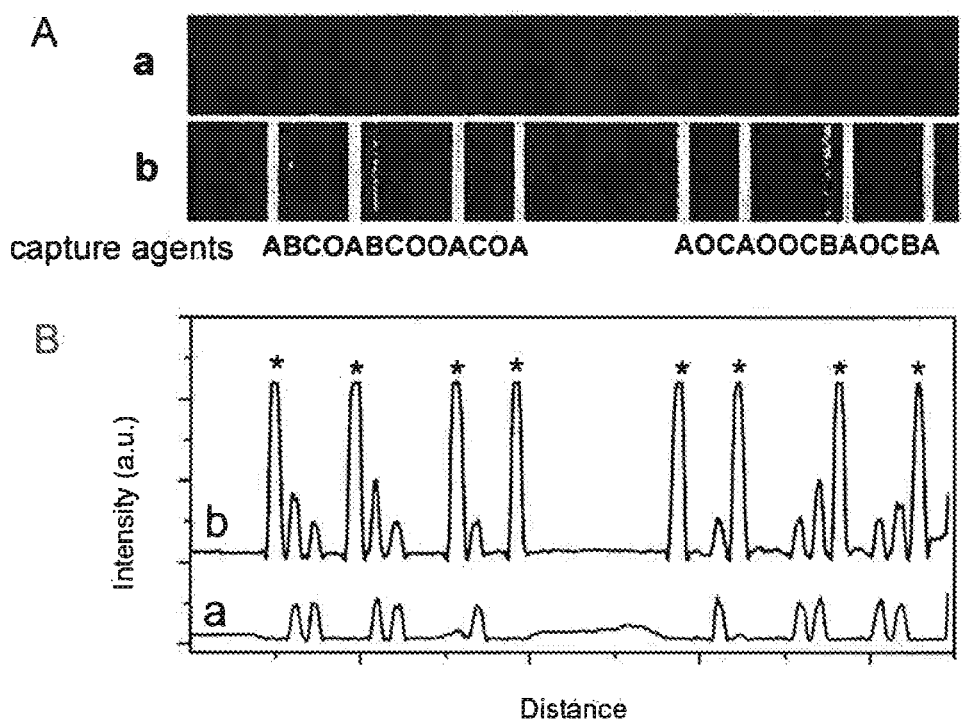
FIG. 16 shows an exemplary detection of target polynucleotides according to an embodiment herein disclosed.

In particular, in FIG. 16 panel A, fluorescence images are reported taken before and after hybridization of an A' strand to its Alexa 532 labeled complementary stand. Three different strands of DNA oligomers, nonfluorescent A, Alexa 532 labeled B (red) and Alexa 635 labeled (dark green) were flow-patterned on a polyL-lysine slide to form this bar-code chip. "0" denotes a non-patterned channel for bland control. After applying the Alexa-532 labeled A' molecule s (its concentration is 1 nanomolar, these DNA molecules are complementary to the surface bound A stands), a clear and strong green fluorescence band emerges, indicating highly effective and specific sensing of A' DNA molecules.

The line profile of fluorescence intensity across the whole set of bar-code array is shown in FIG. 16 Panel B. In the illustration of FIG. 16, A' is the target polynucleotide that was added into sample b and detected by fluorescence change in the location indicated by an asterisk.

Example 5: Use of Barcoded Array for Protein Detection

A barcoded array assembled as disclosed herein was used for protein detection according to an experimental approach developed by the applicants.

In particular, applicants developed a multiplexed assay of 12 plasma proteins using DEAL barcode arrays. In a first test, the level of cross-reactivity of each antigen with DEAL stripes that are not specific to that antigen was assessed. DNA-encoding capture antibodies and biotinylated detection antibodies for all 12 antigens were used as usual, but a distinct antigen (10 nM) was added to each assay lane. Cy5-Streptavidin (red-fluorescence tag) was run as usual to visualize the extent of analyte capture.

The reference marks (DNA strand M) were visualized in all lanes with fluorescent green Cy3-M' DNA molecules. The 12 proteins showed a negligible extent of cross-talk. In a second test, assays were performed on serial dilutions of all 12 proteins on the DEAL barcode chip in view of the limitation imposed by the particular devices used, each allowing a maximum of 12 parallel assays to be executed. In the specific experimental approach of choice for this setting 6 lanes were used for cross-talk validation and 6 lanes were used for dynamic range studies.

Figure 17:
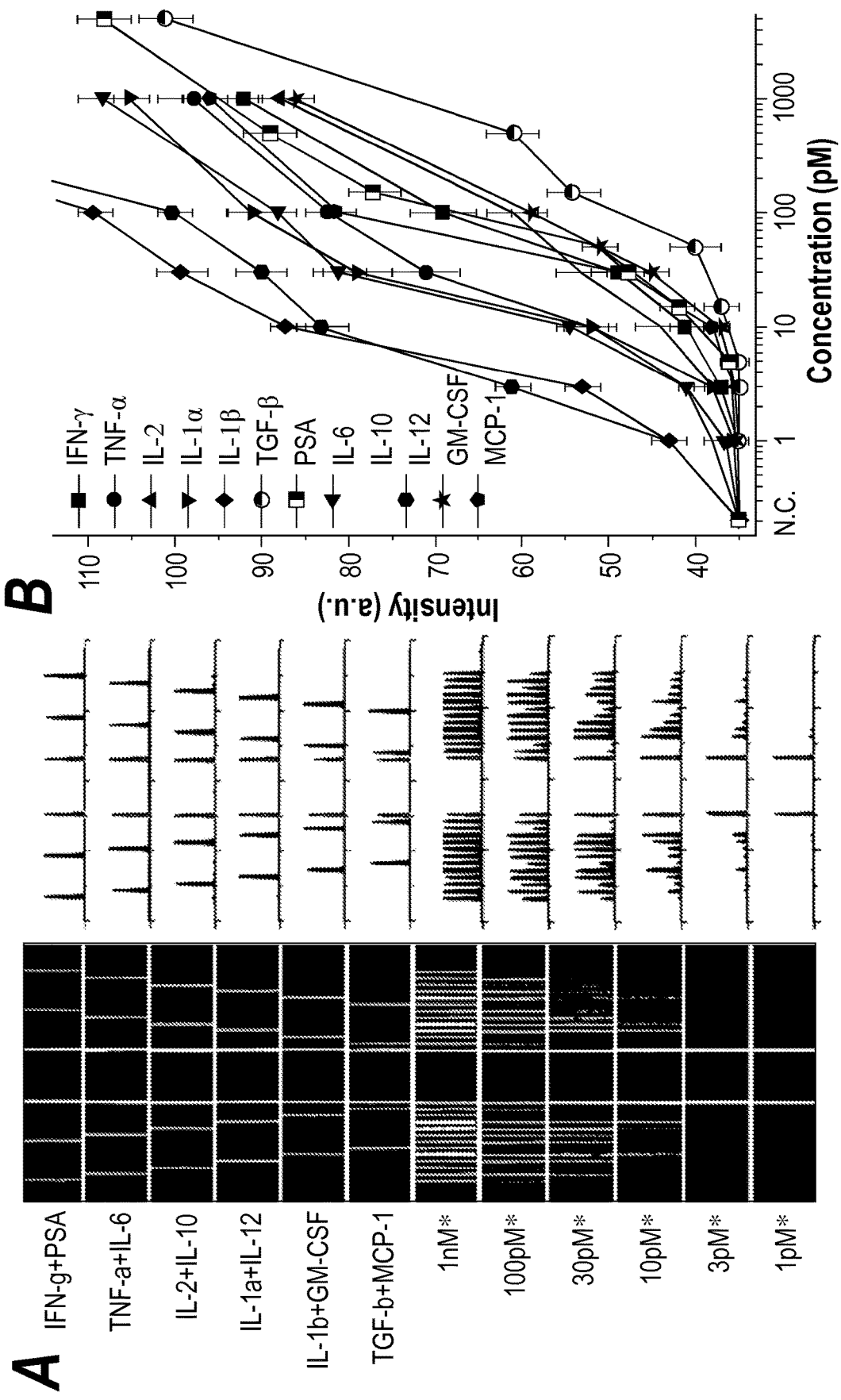
FIG. 17 shows an exemplary multiplexed detection of multiple protein targets in a sample using a barcoded array according to an embodiment herein disclosed.

The results are illustrated in FIG. 17 which shows cross-reactivity check and dilution curves for all 12 proteins. In particular, the DEAL barcode images and line profiles from a single device of panel (a) show minimal cross-talk and a series of standard antigens ranging from 1 nM to 1 pM for all 12 proteins. In the experiments shown in panel (a), 2 proteins were combined in each assay lane (FIG. 17 panel (a)).

All proteins were assayed on the same chip over the concentration range of 1 nM down to 1 pM (except PSA and TGF-b: 5 nM to 5 pM), and quantified the fluorescence signal vs. concentration for all 12 antigens as illustrated in FIG. 17 panel (b), where dilution curves for all 12 proteins are shown.

In this experiment, all the concentrations were imaged using the Genepix scanner at the same laser power (55 for 635 nm, 15 for 532 nm), optical gain (500 for 635 nm and 400 for 532 nm), and brightness/contrast (92/90) in order for quantitative comparison. Apparently, the estimated sensitivity varies a lot from ~0.3 pM (e.g. IL-1β and IL-12) to 30 pM (TGF-β) largely depending on the antibodies being used. For example, the TGF-b antibody pair has a relatively lower binding affinity and a poorer detection limit in ELISA (according to the spec sheet, it is ~70 pg/mL compared to 5-10 pg/mL for most other cytokines). Predictably, this gave rise to a poorer performance in the DEAL assay. Although these curves clearly show a dynamic response of DEAL signals with respect to antigen concentrations, the variation remains pretty large as compared to bulk-scale immunoassay such as ELISA.

Detection probes are not limited to fluorescent dyes, but can be any others that are capable to transduce signal from captured targets to optical, magnetic or electrical read out.

In particular, an alternative method of detection is provided by use of gold nanoparticles as probes. An exemplary illustration of detection performed using gold nanoparticles is shown in FIG. 18, wherein detection of target protein IL-1β using gold nanoparticles as the probe is shown.

Figure 18:
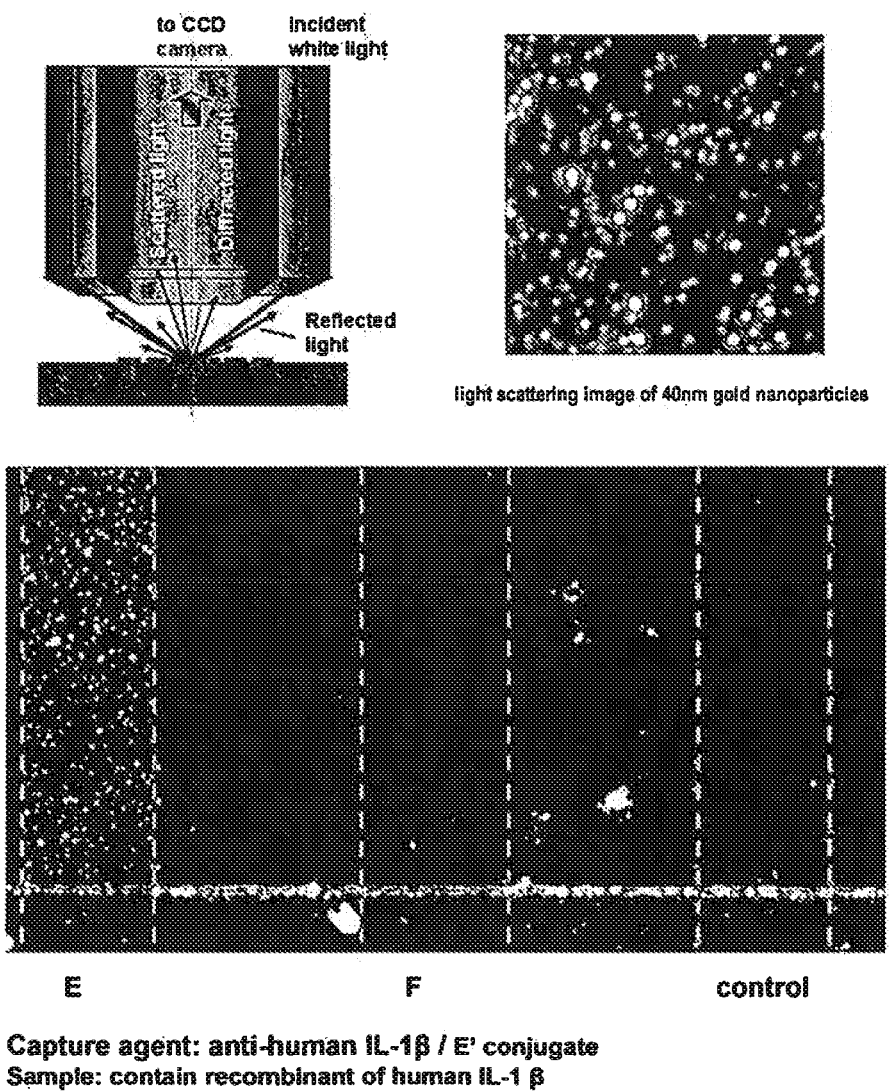
FIG. 18 shows an exemplary detection of a protein target according to an embodiment herein disclosed.

In particular, in the example of FIG. 18, 40-nm gold nanoparticles were used to visualize the captured protein (e.g. IL-1β) of interest from human serum).

Additional examples of labels and method of detections are illustrated the U.S. Application entitled "Methods and Systems for Detecting and/or Sorting Targets" Ser. No. 11/888,502 filed on Aug. 1, 2007, incorporated herein by reference in its entirety.

Example 6: Comparative Example Related to Use of a Barcoded Array and a Conventional Microarray for Protein Detection Comparative experiments were performed on the barcode array of example 3 and a conventional microarray printed using pin-spotting technique. The results illustrated in FIG. 15 panel d, show how apparently, the conventional microarray only achieved sensitivity 1-2 orders of magnitude worse than the DEAL barcoded chips.

A side-by-side comparison study was performed by running DEAL assays on three cytokines under identical conditions on a barcoded and a pin spotted microarrays under the experimental conditions illustrated in Example 3. The pin-spotted array was printed at the Institute for Systems Biology at 100 µM concentration. The typical spot size was 150-200 µm. Six sets of spots were printed corresponding to oligomers A, B, C, D, E, and F. Poly-1-lysine coated slides were used for both types of arrays. Further details are illustrated in Example 3.

The results illustrated in FIG. 15 panel e show that barcoded array exhibits greater performance with higher sensitivity than does the conventional array.

In particular, these results demonstrate that the detection sensitivity of the DEAL barcode arrays was higher and the projected sensitivity limit was better than 1 pM, as compared to 10-100 pM for conventional microarrays (FIG. 15 panel e).

The only difference between the barcoded and conventional pin-spotted platforms used in the experiment shown in FIG. 15 is the feature size. The barcode array has a line-width of 20 µm, whereas the spot size in conventional arrays is more than 150 µm. The mechanism for improved sensitivity in the DEAL barcode assay is not completely understood. A possible explanation which is not intended to be limited is that the improved sensitivity could be attributed to a reduced kinetic barrier and decreased diffusion time. These results are consistent with a recent report which demonstrated that DNA microarrays with smaller spot sizes could detect DNA with increased sensitivity.

Example 7: Use of a Barcoded Array for Detection of Multiple Different Targets

Figure 19:
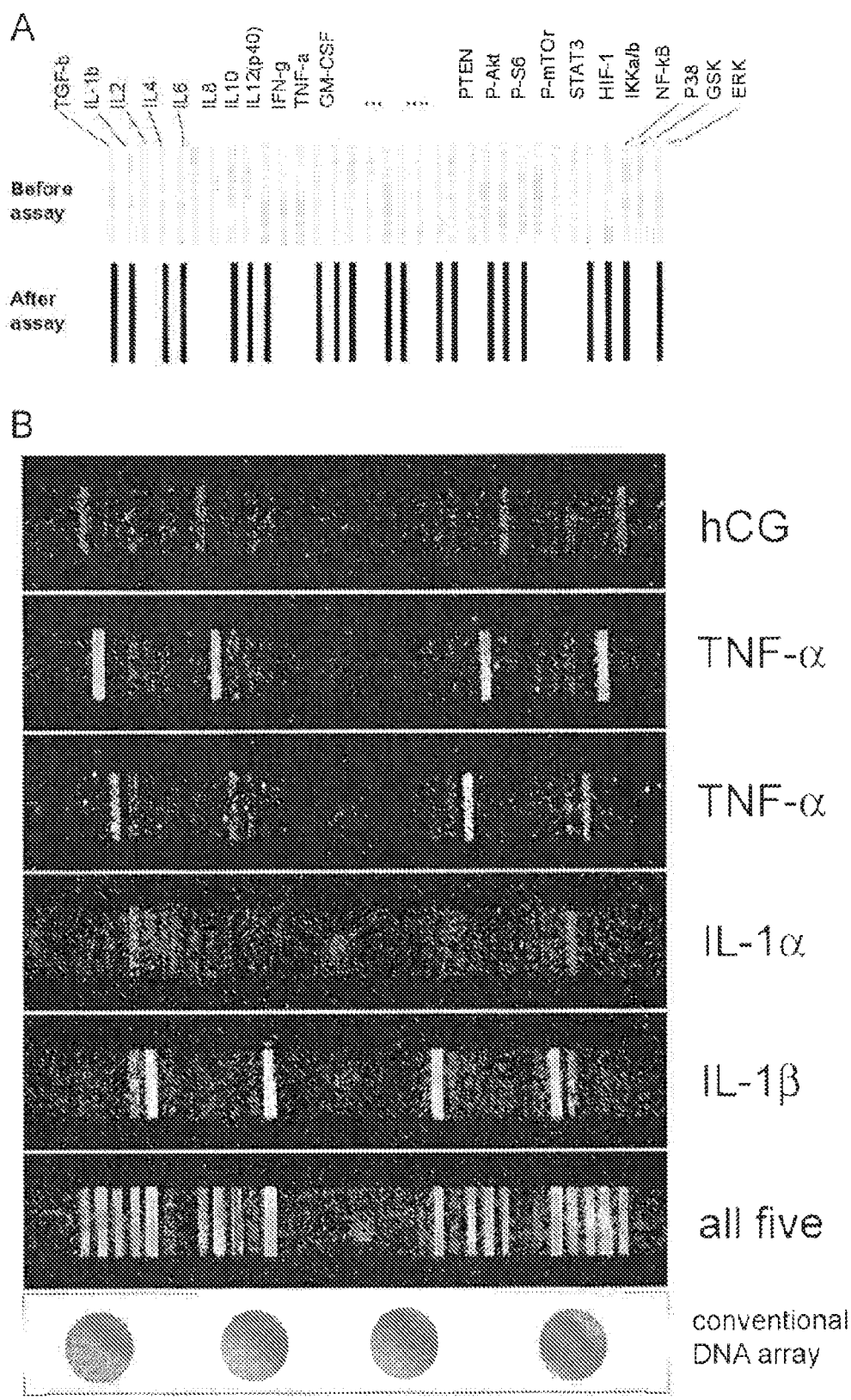
FIG. 19 shows an exemplary detection of multiple targets in a sample using a barcoded array according to an embodiment herein disclosed, and its comparison to the conventional array.

A barcoded array integrated with DEAL technology was used to detect multiple proteins as illustrated in FIG. 19. In particular FIG. 19 shows the use of DEAL bar-code immunoassay for the detection of five different proteins. The proteins are detected within an area that is less than would be required for the detection of a single protein using a conventional spotted microarray.

The results illustrated in FIG. 19 show in particular multiple proteins simultaneously detected using a DEAL bio-barcode. Panel A shows a schematic illustration of DEAL bar-code array for co-detection of a variety of proteins at the same time, including cytokines, chemokines, growth factors, intracellular signaling molecules and cancer markers. Panel B shows a multiparameter DEAL Bar-code immunoassays of 5 proteins at the same time, detected from human reference serum that was spiked with the five proteins: hCG, TNF-α, IL-2, IL-a, and IL-1β. In principle, bar-code array can provide high density assay of a much greater number of protein s simply by increasing the number of microchannel s used in flow patterning.

Figure 20:
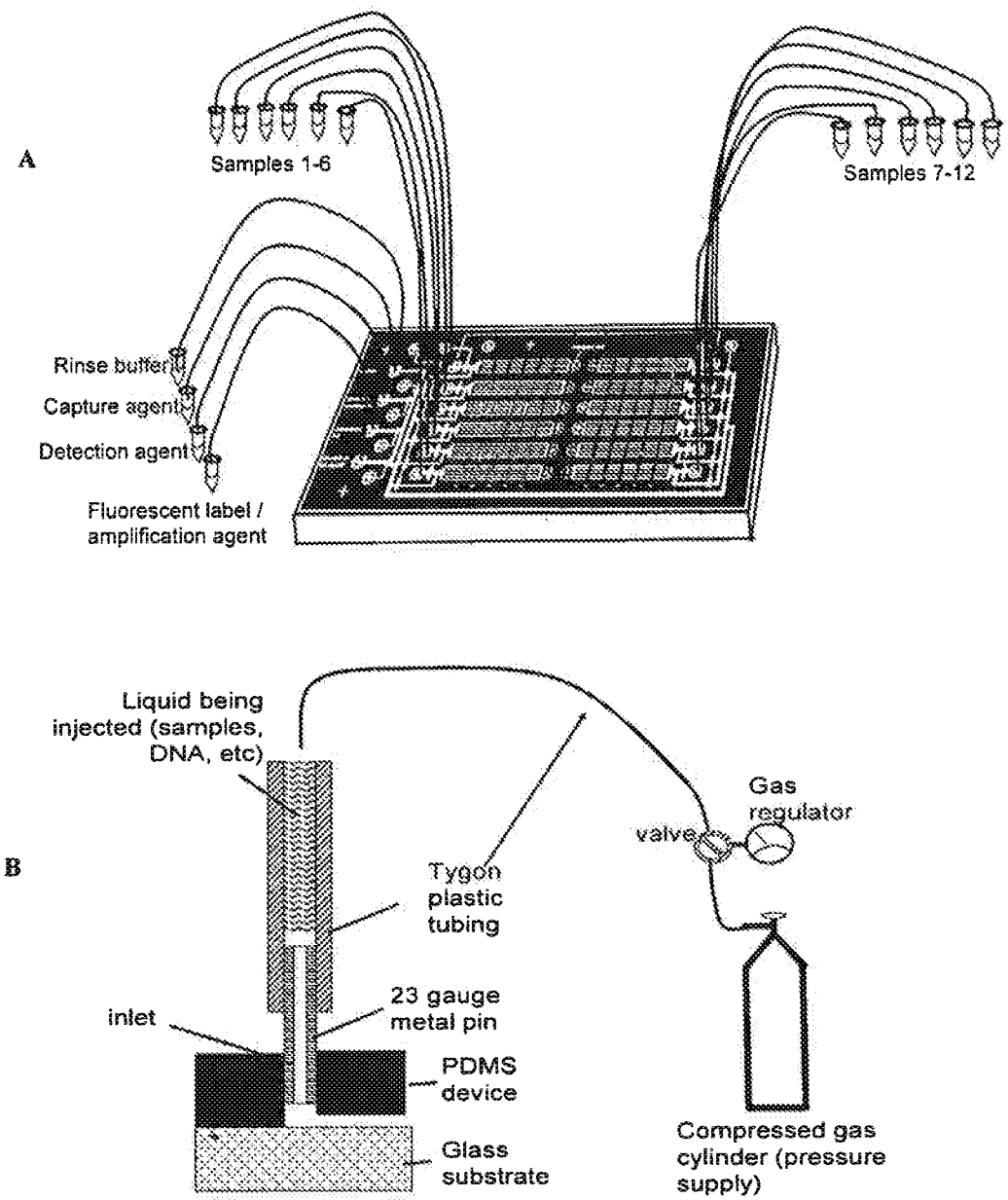
FIG. 20 shows a schematic representation of a method and system to detect targets according to an embodiment herein disclosed.

The detection of multiple targets was performed according to the schematic representation of FIG. 20 that shows the microfluidic device used in patient serum measurement In particular, FIG. 20 panel A shows. the schematic of the operation of a microfluidic device that is bonded onto a barcode array glass slide.

FIG. 20 Panel B shows a schematic illustrating the method to introduce fluid into microfluidic devices for molecular detection and in particular interfacing the outside sample loading/injection systems to the microfluidic device using plastic tubing and metal pins.)

Figure 21:
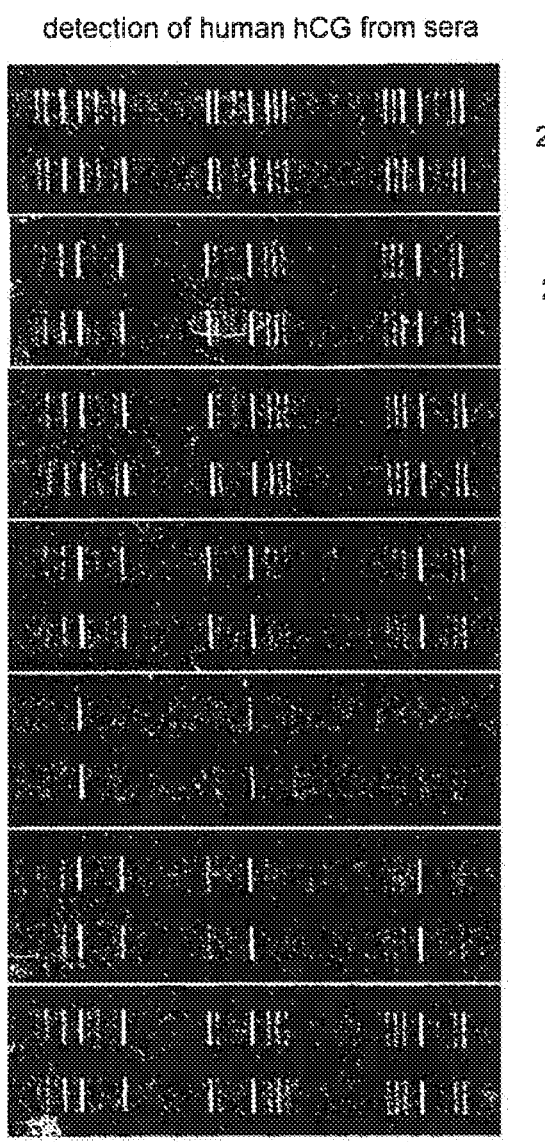
FIG. 21 shows an exemplary detection of a target in a series of samples according to an embodiment herein disclosed.

Example 8: Use of a Barcoded Array to Detect Proteins Over a Broad Dynamic Concentration Range A bio-barcode integrated with DEAL technology was used to detect biomarkers as illustrated in FIG. 21. In particular FIG. 21 illustrates the increased dynamic range of a barcoded array when it is utilized with DEAL technology. The data show measurements of hCG, a pregnancy test marker, in human serum using the DEAL bar-code immunoassay that can cover the huge dynamic range >4 orders of magnitude.

In particular, the results illustrated in FIG. 21, show that an expanded range of concentrations that can be detected from a single DEAL-based bio-barcode, demonstrated here for the detection of hCG. hCG is a pregnancy test marker, as well as a serum cancer marker. By varying the primary DNA oligomer concentration that binds the 1° antibody capture agent during the initial flow patterning step, a single set of bar-code can distinguish the hCG concentration spanning from 25000 mIU/mL to 0.25 mIU/mL (not shown) in a single step.

Example 9: Barcoded Array for Detecting a Biological Profile: Detection of Human Chorionic Gonadotropin (hCG) Over a Period of Time Applicants performed a test on a series of standard human chorionic gonadotropin (hCG) spiked human serum samples provided by the National Cancer Institute (NCI). hCG is widely used for pregnancy testing, and also serves as a biomarker for gestational trophoblastic tumors and germ cell cancers of the ovaries and testes.

Figure 22:
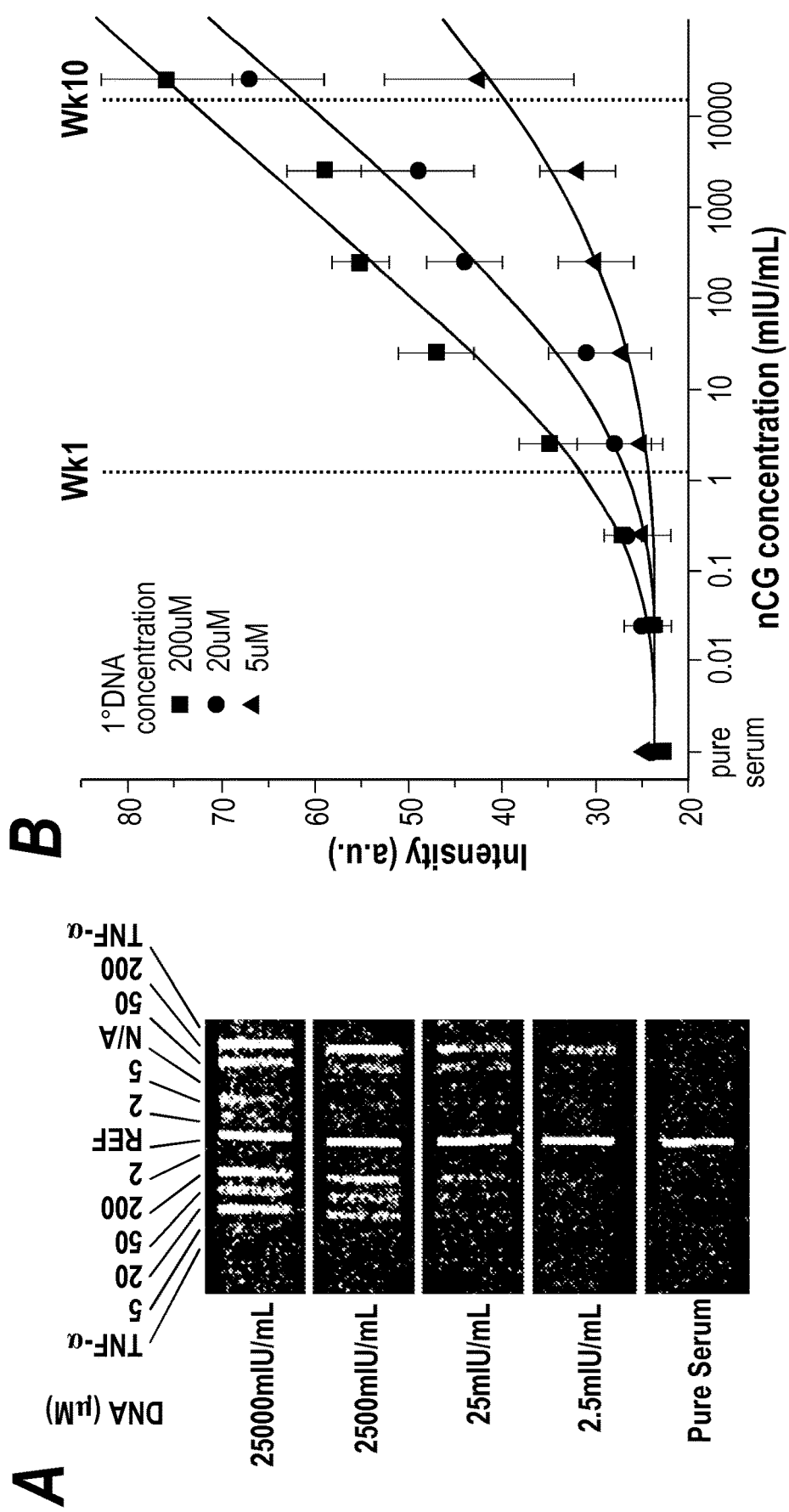
FIG. 22 an exemplary detection of a protein target in a series of samples over a large concentration range according to an embodiment herein disclosed.

The results from these hCG assays are shown in FIG. 22, which illustrate measurement of human chorionic gonadotropin (hCG) spiked in sera using a microfluidic DEAL barcode chip on an integrated platform including a barcoded array manufactured as described in U.S. Application entitled "Microfluidic Devices, Methods and Systems for Detecting Target Molecules" Ser. No. 11/164,737 filed on Jul. 16, 2008, herein incorporated by reference in its entirety.

In Panel a of FIG. 22, fluorescence images of DEAL barcodes used in measuring standard hCG samples and two unknowns, are shown. The bars used to measure hCG were patterned with DNA strand A at different concentrations. TNF-α encoded by strand B was employed as a negative control. The lane indicated with REF represents the reference marker, while the other lanes indicate hCG test results in which the DNA was patterned from solutions at concentrations that varied from 2 µM-200 µM. A negative control using TNF-α was also included.

ELISA-like sensitivity (~1 mIU/mL), but with a broader detectable concentration range (~$10^5$), was demonstrated by quantitating fluorescence intensity. Moreover, even without photon integration, the analyte concentrations over a large range can be readily estimated by eye through pattern-recognition of the full barcode (See also indication in Example 5).

Quantitation of fluorescence signals obtained at different DNA loading was also performed as indicated in panel (b) of FIG. 22. In such a barcoded array, the bar with high DNA-loading rendered great sensitivity at low analyte concentrations, whereas the bar with low DNA-loading was used to readily discriminate samples with high analyte concentrations. The two unknowns were also assayed and the results are in good agreement with ELISA tests run at NCI Laboratories.

Applicants noted that the hCG level is tracked during pregnancy, with concentrations in the blood increasing from ~5 mIU/mL in the first week of pregnancy to ~$2\times10^5$ mIU/mL in ten weeks. The microfluidic barcoded arrays used in the experiments herein described can accurately cover such a broad physiological hCG range.

Figure 23:
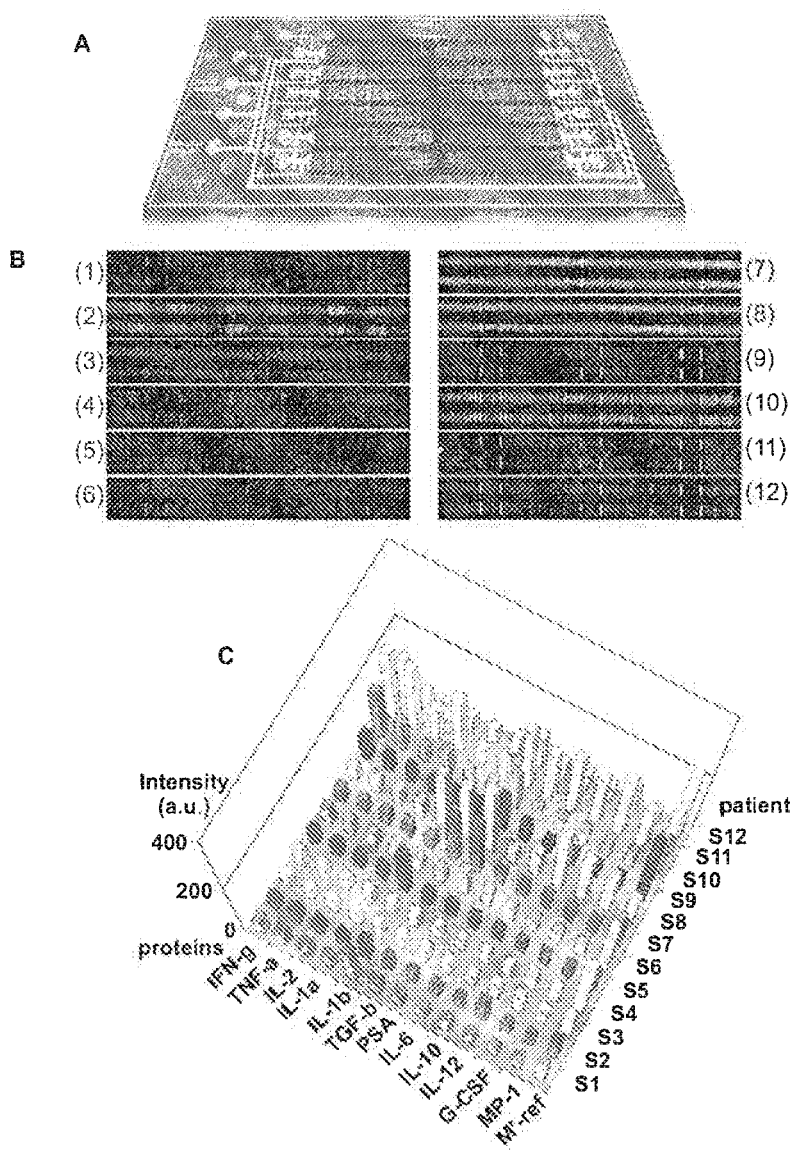
FIG. 23 shows an exemplary detection of a biological profile according to an embodiment herein disclosed.

Example 10: Barcoded Array for Detecting a Biological Profile: Protein Profiling in Cancer Patients A barcoded array was used to detect a biological profile as illustrated in FIG. 23. In particular, FIG. 23 shows the use of an integrated microfluidic DEAL barcoded device for human serum protein profiling. The serum samples from 12 cancer patients were measured in such prototype clinic test platform.

The protein profile obtained from this experiment exhibits unique patterns for individual patients, suggesting the efficacy of DEAL bar-code assay for serum-based cancer diagnosis and personalized medicine. This result displays a great indication for using a barcoded device and in particular an integrated DEAL barcode device for diagnostics and in particular human disease diagnostics.

In particular, the results of FIG. 23 show that the integrated DEAL Bio bar-code device can be used for rapid, sensitive and high-throughput protein measurements out of cancer patient sera. Panel A illustrates the design of the integrated microfluidic device that can conduct a dozen of serum assays at the same time in a highly automated fashion. Blue denotes the microfluidic channels for delivery of all reagents and samples. Magenta shows the control channel for pressure-actuated valves where they intersect the microfluidic channels. Overlay is a representative image of DEAL bar-code chip visualized by Cy5 fluorescence probes.

Measurement of 12 proteins out of 11 cancer patient serum samples and reference serum is illustrated in Panel B. The number denotes each individual lanes used for protein detection out of a patient sample.

Statistics of 12 protein level present in the serum samples from 12 different patients (S I-S 12), among which S1-5 are breast cancer patients while S6-S 11 are prostate cancer patients, is shown in Panel C. Each patient displays a unique pattern of serum proteins that are thought to be associated with their unique molecular origin of cancer.

A chart listing the specification and medical history of cancer patients is shown in panel D. Several unique signatures can be seen by comparing the medical record and the serum protein profile measured from DEAL bar-code assay.

Example 11: Barcoded Array for Detecting a Biological Profile: Additional Protein Profiling in Cancer Patients To further assess the utility and reproducibility of barcoded array for clinical blood samples, applicants measured a panel of 12 proteins from small amounts of serum from 24 cancer patients in a DEAL barcoded microfluidic device. The proteins in this panel included prostate specific antigen (PSA), as well as eleven proteins secreted by various white blood cells. Each barcode was measured many times for each serum sample.

The stored serum samples from 11 breast cancer patients (all female) and 11 prostate cancer patients (all male) were acquired from Asterand. Two unknowns were acquired from Sigma-Aldrich. Nineteen out of 22 patients were Caucasian and the remaining three were Asian, Hispanic and African-American. The medical history is summarized in the supplementary materials.

Finger pricks were performed using BD Microtainer Contact-Activated Lancets. Blood was collected with SAFE-T-FILL capillary blood collection tubes (RAM Scientific), which we pre-filled with 80 µL of 25 mM EDTA solution. A 10 µL volume of fresh human blood from a healthy volunteer was collected in this EDTA-coated capillary, dispensed into the tube, and rapidly mixed by inverting a few times. The spiked blood sample was prepared in a similar means except that 40 µL of 25 mM EDTA solution and 40 µL of recombinant solution were mixed and pre-added in the collection tube. Then 2 µL of 0.5 M EDTA was added to bring the total EDTA concentration up to 25 mM.

Execution of blood separation and plasma protein measurement was performed using an integrated platform extensively described in U.S. entitled "Microfluidic Devices, Methods and Systems for Detecting Target Molecules" Ser. No. 11/167,737 filed on Jul. 16, 2008, herein incorporated by reference in its entirety.

The integrated platforms were first blocked with the buffer solution for 30-60 minutes. The buffer solution prepared was 1% w/v Bovine Serum Albumin Fraction V (Sigma) in 150 mM 1×PBS without calcium/magnesium salts (Irvine Scientific). Then DNA-antibody conjugates (~50-100 nM) were flowed through the plasma assay channels for ~30-45 min. This step transformed the DNA arrays into capture-antibody arrays. Unbound conjugates were washed off by flowing buffer solution through the channels. At this step, the integrated platform was ready for the blood test. Two blood samples prepared as mentioned above were flowed into the integrated platforms within 1 minute of collection. The integrated platform quickly separated plasma from whole blood, and the plasma proteins of interest were captured in the assay zone where DEAL barcode arrays were placed. This whole process from finger-prick to plasma protein capture took <10 minutes. In the cancer-patient serum experiment, the as-received serum samples were flowed into the integrated platforms without any pre-treatment (i.e. no purification or dilution). Afterwards, a mixture of biotin-labeled detection antibodies (~50-100 nM) for the entire protein panel and the fluorescence Cy5-streptavidin conjugates (~100 nM) were flowed sequentially into the integrated platforms to complete the DEAL immunoassay. The unbound fluorescence probes were rinsed off by flowing the buffer solution for 10 minutes. At last, the PDMS chip was removed from the glass slide. The slide was immediately rinsed in ½×PBS solution and deionized water, and then dried with a nitrogen gun. Finally, the DEAL barcode slide was scanned by an Axon Instruments Genepix Scanner.

The serum samples from 24 cancer patients were assayed using two chips, each containing 12 separate assay units that were operated in parallel. In every assay unit, 50 sets of DEAL barcodes were placed in the detection channel for statistical sampling of the serum. In all experiments, 25 µL of patient serum, or 500 nanoliters per barcode, was used for each assay. The white-blood cell secreted proteins included inflammatory molecules and cytokines. These proteins are employed by immune cells for intracellular communication, and have significant implications in tumor microenvironment formation, and in tumor progression and metastasis. Thus, this panel provides information on both cancer and the immune system.

Experiments were repeated at least 2-3 times. In every integrated platform, multiple sets of barcode arrays were patterned in a single assay channel to allow simultaneous parallel measurements. For example, 50 sets of barcode were used in assaying a cancer patient serum sample, with each barcode detecting the full panel of proteins. Quantitation of fluorescence signal was performed using either the Genepix software or imageJ (NIH). In processing the cancer-patient data, the background intensity for each channel was individually identified, and then re-assigned to a common background level of 20 arbitrary units. The intensities of all "bars" in a given channel are normalized to that channel's background. Therefore, the data in FIG. 10 corresponds to the bar's fluorescence intensity differences relative to its own channel's background, plus the common background level of 20. This treatment minimizes interference from non-specific background signal, but could make it indistinguishable between the positive results with high background (e.g. B10) and the true negative results (e.g. B9 and B11).

Figure 24:
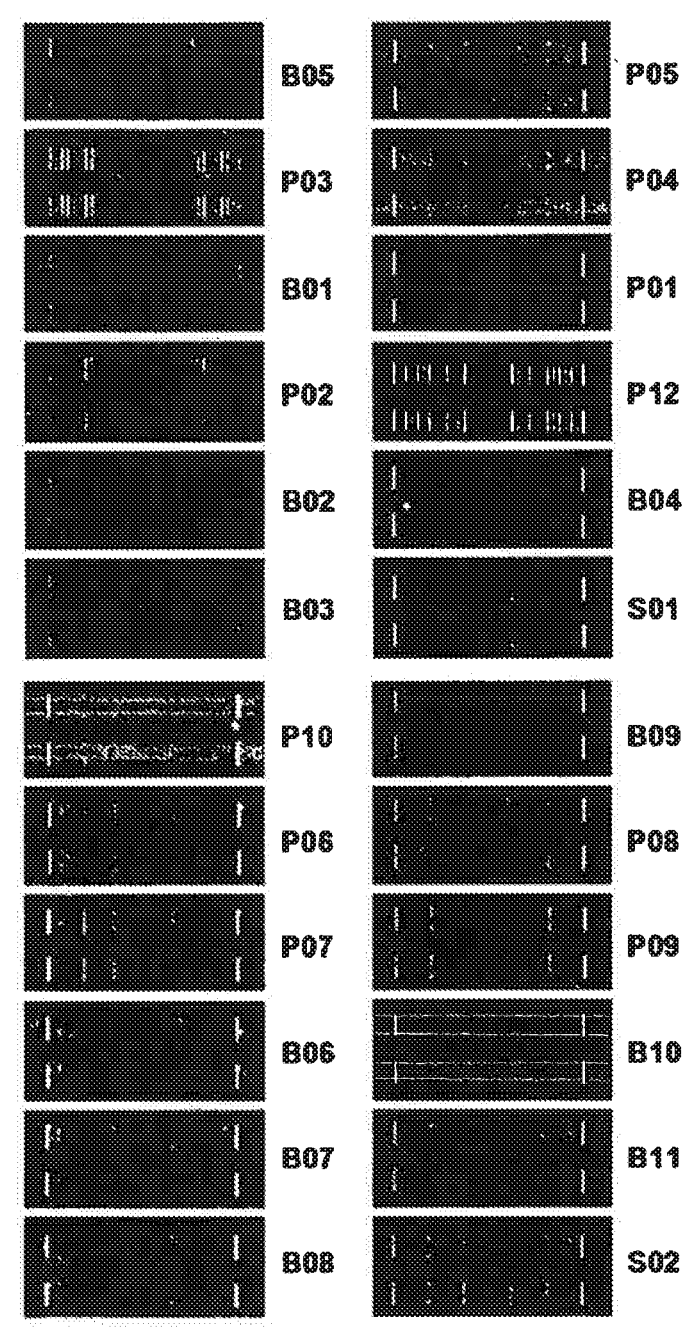
Figure 25:
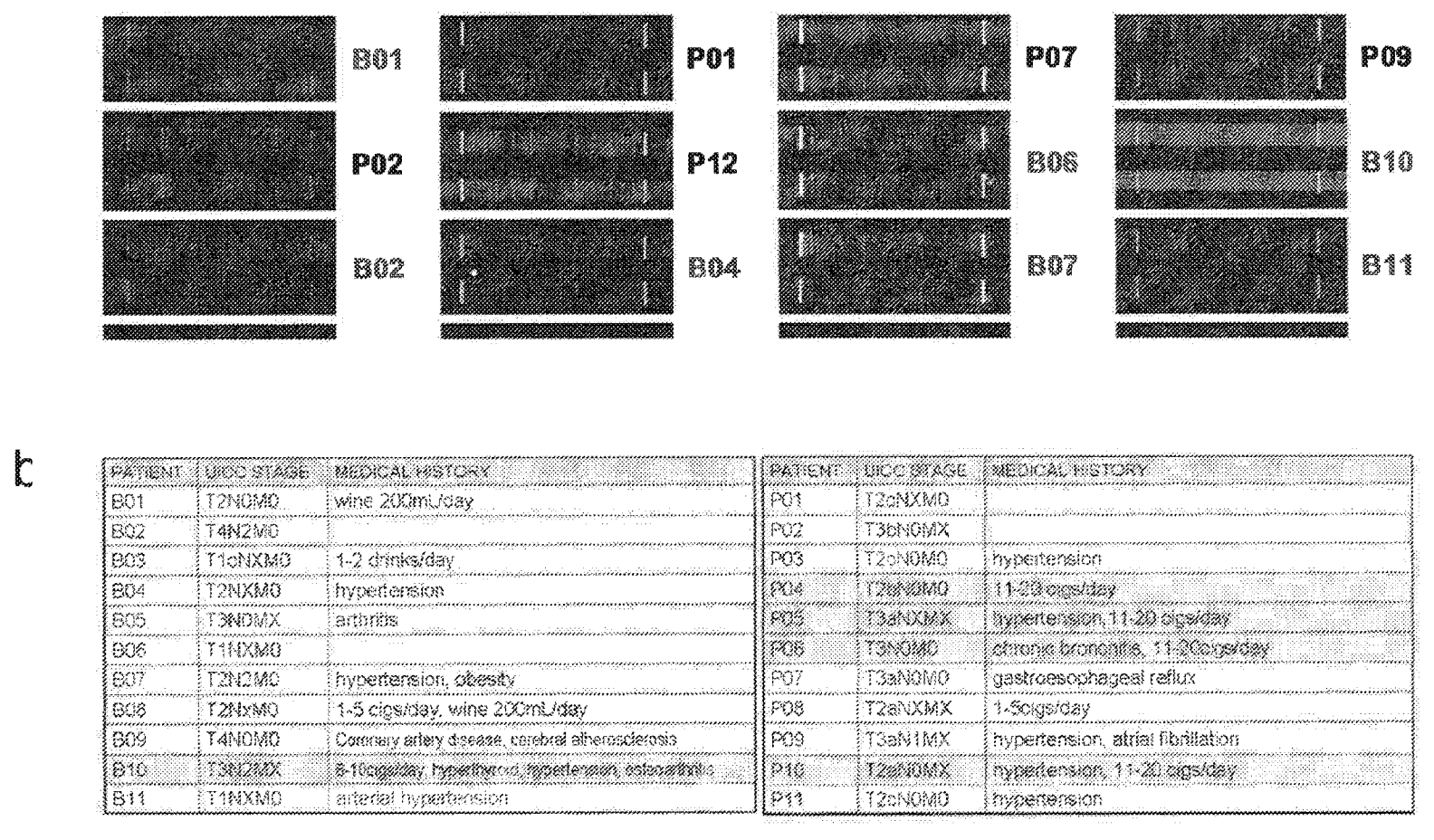

The results are illustrated in FIGS. 24 and 25, which show the related profile of cancer patients (FIG. 24) together with their medical history (FIG. 25).

In particular, fluorescence images each showing four sets of representative barcodes obtained from the 24 patient samples are shown in FIG. 24. The proteins measured include cancer marker PSA and eleven cytokines also indicated in details in FIG. 25. In the barcode image panel, the left two columns were performed on the same chip while the right two were from the other. The samples were randomly picked in the assay to minimize arbitrary bias. B01-B11 denote 11 samples from breast cancer patients, P01-P11 denote those from prostate cancer patients, whereas the S01 and S02 are unknown samples from a different supplier.

The medical records for all patients are summarized in FIG. 24 which shows a brief summary of cancer patient medical records. The two unknowns are not included in the table.

A more detailed medical history of the patients is included in the following table 1.

Many proteins were successfully detected with high signal-to-noise, and the barcode signatures are distinctive among patients. Most assays show a relatively low fluorescence background. However, the assays on P05, P04, P10 and B10 were characterized by a high, interfering background. These high background assays all correlate with patients that were heavy smokers (~11-20 cigs/day); only one serum sample from a heavy smoker did not exhibit a high background (P06). The reason for this high background fluorescence remains unclear. A possible cause is the elevated blood content of the fluorescent carboxyhemoglobin formed in lung. While this identification of smokers constitutes unexpected information from the IBBCs, it also means that, for these patients, some pre-purification of the plasma or serum will be required in order to assay serum protein levels.

The protein panels used in the cancer-patient serum experiment (panel 1) and finger-prick blood test (panel 2), the corresponding DNA codes, and their sequences are summarized in Tables 2 and 3. These DNA oligomers were synthesized by Integrated DNA Technologies (IDT), and purified by high pressure liquid chromatography (HPLC). The quality was confirmed by mass spectrometry.

TABLE 2

List of protein panels and corresponding DNA codes.

| DNA-code | Human Plasma Protein | Abbreviation |
|---|---|---|
| Panel (1) | | |
| A/A' | Interferon-gamma | IFN-γ |
| B/B' | Tumor necrosis factor-alpha | TNF-α |
| C/C' | Interleukin-2 | IL-2 |
| D/D' | Interleukin-1 alpha | IL-1α |
| E/E' | Interleukin-1beta | 1L-1β |
| F/F' | Transforming growth factor beta | TGF-β |
| G/G' | Prostate specific antigen (total) | PSA |
| H/H' | Interleukin-6 | IL-6 |

TABLE 1

Medical Record of cancer patients.

| PATIENT | CANCER | GENDER/AGE | RACE | UICC STAGE | GLEASONS SCORE | OTHERS |
|---|---|---|---|---|---|---|
| B01 | Breast | Female/62 | Caucasian | T2N0M0 | | wine 200 mL/day |
| B02 | Breast | Female/79 | Caucasian | T4N2M0 | | |
| B03 | Breast | Female/71 | Caucasian | T1cNXM0 | | 1-2 drinks/day |
| B04 | Breast | Female/72 | Caucasian | T2NXM0 | | hypertension |
| B05 | Breast | Female/89 | Caucasian | T3N0MX | | arthritis |
| B06 | Breast | Female/56 | Asian | T1NXM0 | | |
| B07 | Breast | Female/54 | Caucasian | T2N2M0 | | hypertension, obesity |
| B08 | Breast | Female/55 | Caucasian | T2NxM0 | | 1-5 cigs/day, wine 200 mL/day |
| B09 | Breast | Female/83 | Caucasian | T4N0M0 | | Coronary artery disease, cerebral atherosclerosis |
| B10 | Breast | Female/63 | Hispanic | T3N2MX | | 6-10 cigs/day, hyperthyroid, hypertension, osteoarthritis |
| B11 | Breast | Female/63 | Caucasian | T1NXM0 | | arterial hypertension |
| P01 | Prostate | Male/51 | Caucasian | T2cNXM0 | 4 + 3 = 7 | |
| P02 | Prostate | Male/64 | Caucasian | T3bN0MX | 3 + 4 = 7 | |
| P03 | Prostate | Male/47 | Caucasian | T2cN0M0 | 3 + 3 = 6 | hypertension |
| P04 | Prostate | Male/55 | Caucasian | T2bN0M0 | 3 + 3 = 6 | 11-20 cigs/day |
| P05 | Prostate | Male/73 | Caucasian | T3aNXMX | 4 + 4 = 8 | hypertension, 11-20 cigs/day |
| P06 | Prostate | Male/64 | Caucasian | T3N0M0 | | chronic bronchitis, 11-20 cigs/day |
| P07 | Prostate | Male/60 | Caucasian | T3aN0M0 | 3 + 4 = 7 | gastroesophageal reflux |
| P08 | Prostate | Male/72 | African Am. | T2aNXMX | 3 + 3 = 6 | 1-5 cigs/day |
| P09 | Prostate | Male/78 | Caucasian | T3aN1MX | 4 + 3 = 7 | hypertension, atrial fibrillation |
| P10 | Prostate | Male/66 | Caucasian | T2aN0MX | 3 + 3 = 6 | hypertension, 11-20 cigs/day |
| P11 | Prostate | Male/47 | Caucasian | T2cN0M0 | 3 + 3 = 6 | hypertension |
| S01 | Unknown | | | | | |
| S02 | Unknown | | | | | |

TABLE 2-continued

List of protein panels and corresponding DNA codes.

| DNA-code | Human Plasma Protein | Abbreviation |
|---|---|---|
| I/I' | Interleukin-10 | IL-10 |
| J/J' | Interleukin-12 | IL-12 |
| K/K' | Granulocyte-macrophage colony stimulating factor | GM-CSF |
| L/L' | Monocyte chemoattractant protein-1 | MCP-1 |
| M/M' | Blank control/reference | |

TABLE 2-continued

List of protein panels and corresponding DNA codes.

| DNA-code | Human Plasma Protein | Abbreviation |
|---|---|---|
| | Panel (2) | |
| AA/AA' | Interleukin-1beta | IL-1β |
| BB/BB' | Interleukin-6 | IL-6 |
| CC/CC' | Interleukin-10 | IL-10 |
| DD/DD' | Tumor necrosis factor-alpha | TNF-α |
| EE/EE' | Complement Component 3 | C3 |
| FF/FF' | C-reactive protein | CRP |
| GG/GG' | Plasminogen | Plasminogen |
| HH/HH' | Prostate specific antigen (total) | PSA |

TABLE 3

List of DNA sequences used for spatial encoding of antibodies

| Sequence Name | Sequence | SEQ ID NO | Tm (50 mM NaCl) °C. |
|---|---|---|---|
| A | 5'-AAA AAA AAA AAA AAT CCT GGA GCT AAG TCC GTA-3' | 1 | 57.9 |
| A' | 5' NH3-AAA AAA AAA ATA CGG ACT TAG CTC CAG GAT-3' | 2 | 57.2 |
| B | 5'-AAA AAA AAA AAA AGC CTC ATT GAA TCA TGC CTA-3' | 3 | 57.4 |
| B' | 5' NH3AAA AAA AAA ATA GGC ATG ATT CAA TGA GGC-3' | 4 | 55.9 |
| C | 5'-AAA AAA AAA AAA AGC ACT CGT CTA CTA TCG CTA-3' | 5 | 57.6 |
| C' | 5' NH3-AAA AAA AAA ATA GCG ATA GTA GAC GAG TGC-3' | 6 | 56.2 |
| D | 5'-AAA AAA AAA AAA AAT GGT CGA GAT GTC AGA GTA-3' | 7 | 56.5 |
| D' | 5' NH3-AAA AAA AAA ATA CTC TGA CAT CTC GAC CAT-3' | 8 | 55.7 |
| E | 5'-AAA AAA AAA AAA AAT GTG AAG TGG CAG TAT CTA-3' | 9 | 55.7 |
| E' | 5' NH3-AAA AAA AAA ATA GAT ACT GCC ACT TCA CAT-3' | 10 | 54.7 |
| F | 5'-AAA AAA AAA AAA AAT CAG GTA AGG TTC ACG GTA-3' | 11 | 56.9 |
| F' | 5' NH3-AAA AAA AAA ATA CCG TGA ACC TTA CCT GAT-3' | 12 | 56.1 |
| G | 5'-AAA AAA AAA AGA GTA GCC TTC CCG AGC ATT-3' | 13 | 59.3 |
| G' | 5' NH3-AAA AAA AAA AAA TGC TCG GGA AGG CTA CTC-3' | 14 | 58.6 |
| H | 5'-AAA AAA AAA AAT TGA CCA AAC TGC GGT GCG-3' | 15 | 59.9 |
| H' | 5' NH3-AAA AAA AAA ACG CAC CGC AGT TTG GTC AAT-3' | 16 | 60.8 |
| I | 5'-AAA AAA AAA ATG CCC TAT TGT TGC GTC GGA-3' | 17 | 60.1 |
| I' | 5' NH3-AAA AAA AAA ATC CGA CGC AAC AAT AGG GCA-3' | 18 | 60.1 |
| J | 5'-AAA AAA AAA ATC TTC TAG TTG TCG AGC AGG-3' | 19 | 56.5 |
| J' | 5' NH3-AAA AAA AAA ACC TGC TCG ACA ACT AGA AGA-3' | 20 | 57.5 |
| K | 5'-AAA AAA AAA ATA ATC TAA TTC TGG TCG CGG-3' | 21 | 55.4 |
| K' | 5' NH3-AAA AAA AAA ACC GCG ACC AGA ATT AGA TTA-3' | 22 | 56.3 |
| L | 5'-AAA AAA AAA AGT GAT AAG TC TGC TTC GGC-3' | 23 | 57.2 |
| L' | 5' NH3-AAA AAA AAA AGC CGA AGC AGA CTT AAT CAC-3' | 24 | 57.2 |
| M | 5'-Cy3-AAA AAA AAA AGT CGA GGA TTC TGA ACC TGT-3' | 25 | 57.6 |
| M' | 5' NH3-AAA AAA AAA AAC AGG TTC AGA ATC CTC GAC-3' | 26 | 56.9 |
| AA' | 5' NH3-AAAAAAAAAAGTCACAGACTAGCCACGAAG-3' | 27 | 58 |
| BB | 5'-AAAAAAAAAAGCGTGTGGACTCTCTCTA-3' | 28 | 58.7 |
| BB' | 5' NH3-AAAAAAAAAATAGAGAGAGTCCACACACGC-3' | 29 | 57.9 |
| CC | 5'-AAAAAAAAAATCTTCTAGTTGTCGAGCAGG-3' | 30 | 56.5 |
| CC' | 5' NH3-AAAAAAAAAACCTGCTCGACAACTAGAAGA-3' | 31 | 57.5 |
| DD | 5'-AAAAAAAAAAGATCGTATGGTCCGCTCTCA-3' | 32 | 58.8 |
| DD' | 5' NH3-AAAAAAAAAATGAGAGCGGACCATACGATC-3' | 33 | 58 |
| EE | 5'-AAAAAAAAAAGCACTAACTGGTCTGGGTCA-3' | 34 | 59.2 |
| EE' | 5' NH3-AAAAAAAAAATGACCCAGACCAGTTAGTGC-3' | 35 | 58.4 |
| FF | 5'-AAAAAAAAAATGCCCTATTGTTGCGTCGGA-3' | 36 | 60.1 |
| FF' | 5' NH3-AAAAAAAAAATCCGACGCAACAATAGGGCA-3' | 37 | 60.1 |
| GG | 5'-AAAAAAAAAACTCTGTGAACTGTCATCGGT-3' | 38 | 57.8 |
| GG' | 5' NH3-AAAAAAAAAAACCGATGACAGTTCACAGAG-3' | 39 | 57 |
| HH | 5'-AAAAAAAAAAGAGTAGCCTTCCCGAGCATT-3' | 40 | 59.3 |

TABLE 3-continued

List of DNA sequences used for spatial encoding of antibodies

| Sequence Name | Sequence | SEQ ID NO | Tm (50 mM NaCl) °C. |
|---|---|---|---|
| HH' | 5' NH3-AAAAAAAAAAAATGCTCGGGAAGGCTACTC-3' | 41 | 58.6 |

\* All amine-terminated strands were linked to antibodies to form DNA-antibody conjugates using SFB/SANH coupling chemistry as described by R. Bailey et al.
[1]Codes AA-HH were used in the experiment which examined fresh whole blood from a heathy volunteer. Codes A-M were used for the molecular analyses of cancer patient serum samples.

Example 12: Barcoded Array for Detecting a Biological Profile: Quantitative Protein Profiling in Cancer Patients The blood barcodes measured throughout the experiments illustrated in Example 10 were unique for each patient.

Figure 26:
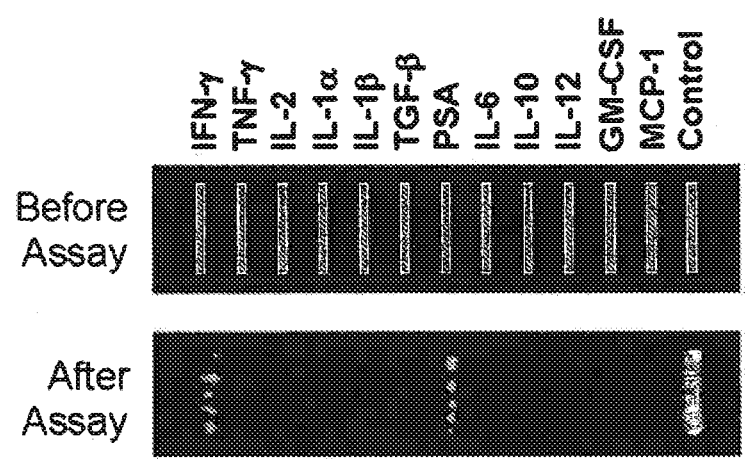
FIG. 26 shows detection of a protein profiling in a time span according to an embodiment herein disclosed.
Figure 27:
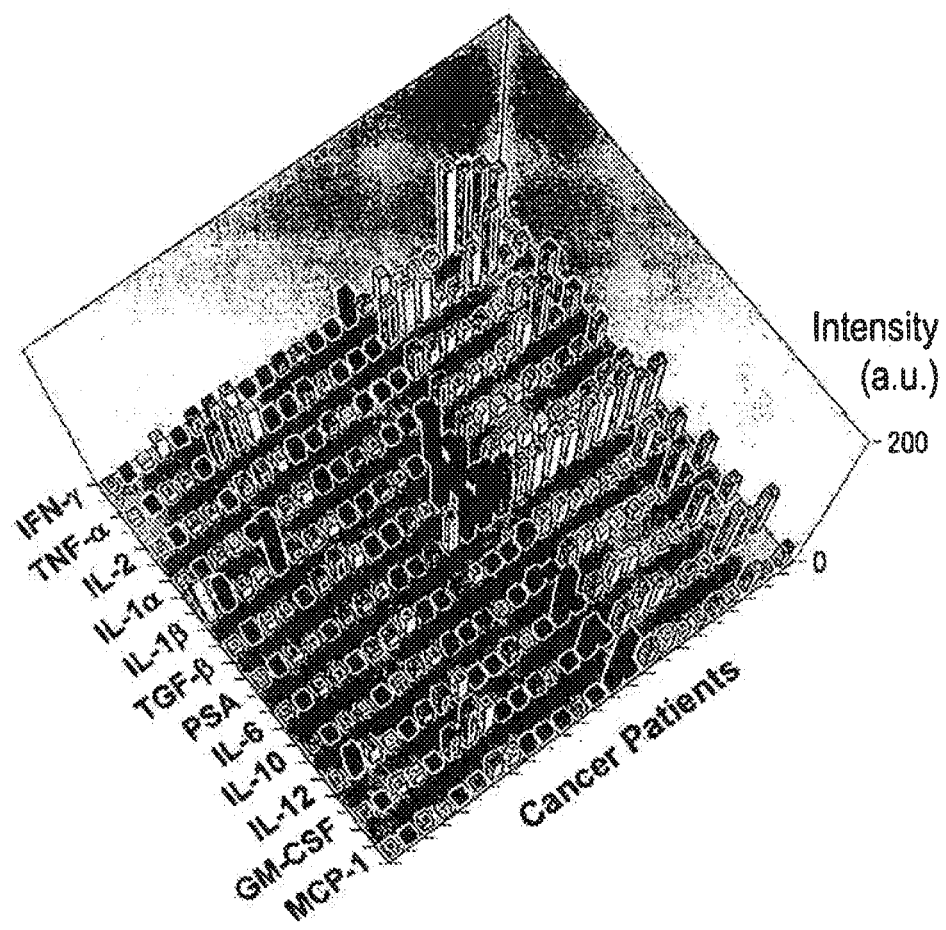
FIG. 27 shows an exemplary quantitative detection according to an embodiment herein disclosed.
Figure 28:
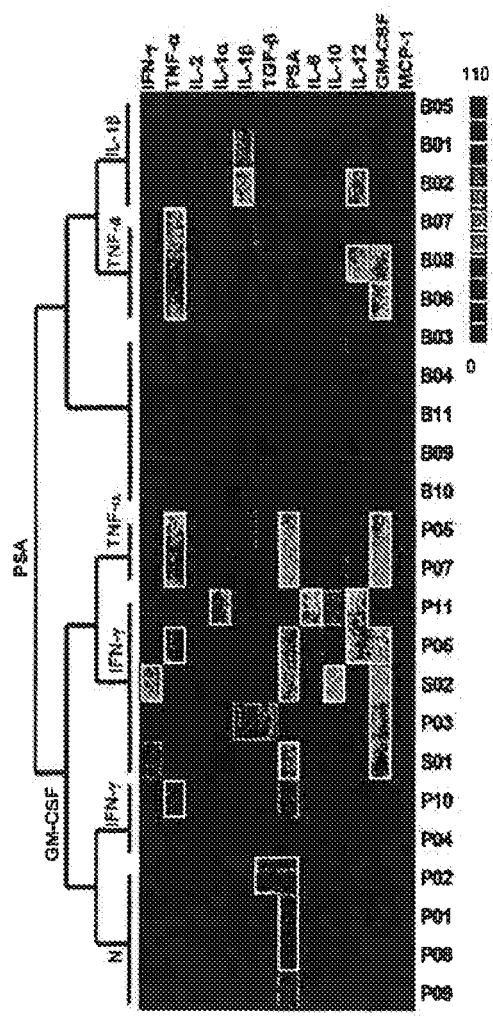
FIG. 28 shows an exemplary elaboration of biological profiles detected according to the exemplary embodiment illustrated in FIG. 21(A) embodiment herein disclosed.

FIGS. 26 to 28 show quantitation and clustering of cancer patient barcode data obtained using a barcode array designed as exemplified in Example 8. In particular, FIG. 26 shows layout of the barcode array used in this study. Strand M denotes the reference (control). FIG. 27 illustrates a plot showing quantitation of fluorescence signals of all proteins (left axis) detected as shown in FIG. 21A for all cancer patients (from left: B01-B11, P01-P11, S01 and S02). S01 and S02 are two unknown serum samples. FIG. 28 shows an exemplary manual clustering of cancer patients derived on the basis of protein patterns. First, all prostate cancer patients are clearly identified by PSA. Second, both breast and prostate cancer patients exhibit possible subpopulations with distinct cytokine profiles.

The fluorescence signals intensity for all the patient samples are plotted in FIG. 26. The cancer marker, PSA, clearly distinguishes between the breast and prostate cancer patients, and allowed for the unknown samples, S01 and S02, to be assigned to prostate cancer patients. Applicants then performed a manual clustering of patients on the basis of protein signals and generated the map schematically illustrated in FIG. 27 to assess the potential of this technology for patient stratification. This approach is only going to be as good as the biomarker panel itself, and the number of serum samples profiled is small. Nevertheless, the results are encouraging. For example, the measured profiles of breast cancer patients can be classified into three subsets—non-inflammatory, IL-1β positive, and TNF-α positive. The prostate cancer patient data exhibits a generally higher level of inflammation, and those inflammation-positive samples can also be classified as shown in FIG. 27. An interesting observation is the lack of IL-10 signal for most patients. IL-10 is a cytokine production suppressor that functions as an anti-inflammatory mediator, and its absence may reflect deviation from normal immune homeostasis in local tumor sites. Applicants have initiated studies involving a larger number of proteins and a much larger number of blood samples. Researches have been focused on developing technologies for multiplexed measurement of cytokines, and serum cytokine profiling has shown relevance in cancer diagnostics and prognostics. The results described above have clearly demonstrated that integrated platforms can be applied to the multiparameter analysis of human health-relevant proteins.

The principal goal behind developing the integrated platform was to be able to measure the levels of a large number of proteins in human blood within a few minutes of sampling that blood, so as to avoid protein degradation that can occur when plasma is stored. In a typical 96 well plate immunoassay, the biological sample of interest is added, and the protein diffuses to the surface-bound antibody. Under sufficient flow conditions, diffusion is no longer important, and the only parameter that limits the speed of the assay is the protein/antibody binding kinetics (the Langmuir isotherm), thus allowing the immunoassay to be completed in just a few minutes.

Example 13: Barcoded Array for Detecting a Biological Profile: Human Plasma Proteome Use of a barcoded array was tested to verify improved sensitivity for plasma protein assays.

The human plasma proteome is comprised of three major classes of proteins—classical plasma proteins, tissue leakage proteins, and cell-cell signaling molecules (cytokines and chemokines). Cell-cell signaling molecules are biologically informative in a variety of physiological and pathological processes, i.e. tumor host immunity and inflammation.

Figure 29:
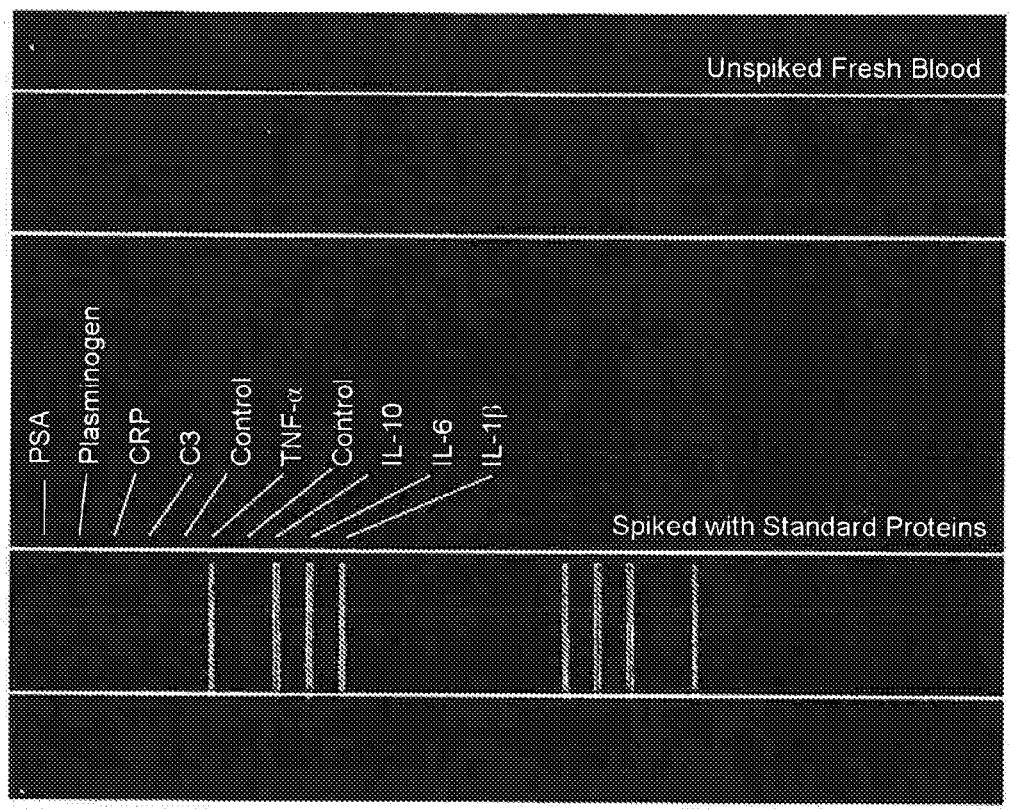
FIG. 29 shows an exemplary detection of target proteins in a drop of fresh human blood.

The results of a first series of experiments performed by the Applicants are illustrated in FIG. 29, wherein a detection of target protein other than cytokines TNF-α, and Interleukins such as IL-6, IL-10 is shown. In particular, FIG. 29, shows detection of molecules such as CRP, C3 and plasminogen associated with biological profile such inflammation response (CRP), complement system (C3) and liver toxicity response (CRP and plasminogen).

Figure 30:
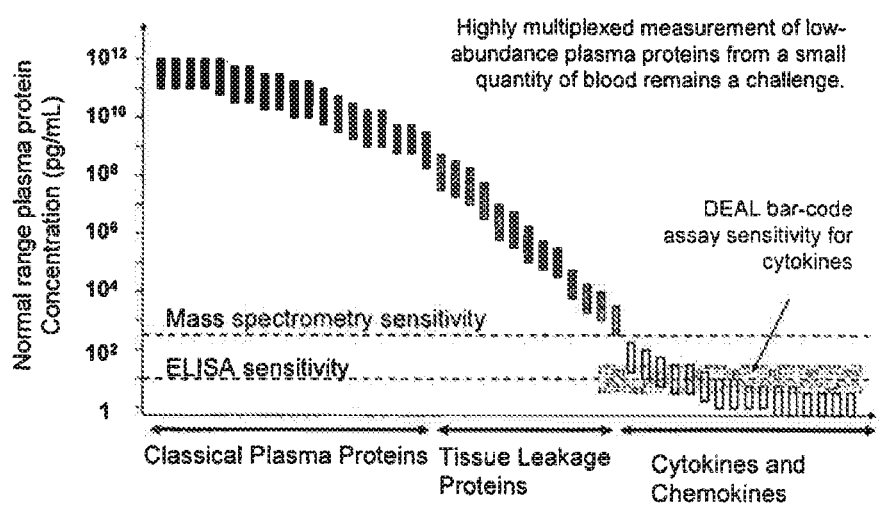
FIG. 30 shows an exemplary detection of a human plasma proteome according to an embodiment herein disclosed.

The results of a second series of experiments performed by the Applicants is summarized in the diagram of FIG. 30, showing a schematic of human plasma proteome (refer to N. L. Anderson and N. G. Anderson, Molecular & Cellular Proteomics 11, 845, 2001).

As shown in FIG. 30, the concentration range of plasma proteins spans 12 orders of magnitude and the lowest end is approximately at the detection limit of mass spectrometry—a high-throughput protein profiling technique. The state-of-the-art for clinical protein measurements is still the ELISA assay. Yet ELISA is a low-throughput process, requiring a large amount of sample and long duration to complete a multiparameter plasma protein measurement. The high performance of the DEAL barcode chip, especially its increased sensitivity, is a key to realizing highly multiplexed measurements of a panel of proteins, including the low abundance cytokines, from small quantities of clinical blood samples.

Applicants therefore concluded that the DEAL barcode assay has a markedly high sensitivity, comparable to ELISA, leading to the feasibility of multiplexed detection of plasma proteins including low-abundance cell-cell signaling molecules, e.g. cytokines and chemokines, from a small quantity of sample.

Example 14: Assay Performed in a Barcoded Array

For the assays shown in the Examples 3-13 illustrated in the related figures, a DEAL immunoassay was used. To detect each protein, a pair of antibodies was chosen. One is conjugated to the secondary DNA strands that are complementary to the primary DNA strands flow-patterned on glass slides. This antibody also serves to capture proteins being detected, and then the biotin-labeled detection came in to bind to the same protein creating immunosandwich structure. Finally, Cy-3 or Cy5 labeled fluorescent streptavidin was used to visualize the results of bar-code through streptavidin-biotin binding.

Detection of human cytokine proteins prepared at different concentrations was first tested (FIG. 15). The results show the detection is highly specific, and exhibits increased sensitivity comparable to ELISA. Then, a multiparameter (up to 5 proteins) detection was demonstrated as in FIG. 16. TNF-a exhibits the best signal intensity due to the high affinity of the 10 anti-TNF-a AB. Having the high loading of primary DNA oligomers and by varying DNA concentrations in flow-pattering step, it is shown the a single bar-code can detect protein like hCG across a huge dynamic range, several orders of magnitude better than any conventional protein detection methods (FIG. 21). Finally, an integrated microfluidic device was fabricated, which comprises of a two-layer PDMS microfluidic chip bonded on to a bar-DEAL barcode glass chip, that allows rapid, sensitive detection of 13 different proteins at the same time out of 12 different human serum samples. The DEAL bar-code devices for the first time provide a highly multiplexed (as in protein microarray and mass spectrometry) method for protein detection at an ultra-high sensitivity as good as the state-of-art ELISA assay.

Barcoded array patterning is a generic technique that can be exploited to pattern DNA, protein, or even sera and tissue lysates. The inverse-phase bar-code array (serum or lysate array) can be used for high throughput drug screening and biomarker discovering.

Example 15: Manufacturing a Barcoded Array for Magnetic ID

A schematic representation of a method to manufacture a magnetic ID barcode on a small object such as a ring is shown in FIG. 31.

A PDMS microfluidic channels with a small exposed contact area can be manufactured using two-layer lithography (it means there are two layers of fluidic channels. The bottom layer can be contacted with the substrate e.g. the small-sized product and the fluid can be introduced from the upper layer that contains embedded fluidic channels to join the bottom layer channels at the small contact area to the large inlets at the sides of the PDMS device.

Once this PDMS device is attached onto the small subject, a number of distinct different molecules were flowed to the contact area to create a DNA barcoded array. Next, a library of complementary DNA-magnetic nanoparticle conjugates can be synthesized.

Therefore, the fabrication of magnetic barcode can be realized by simply immersing the small-sized subject patterned with DNA barcodes into a solution that contains several complementary DNA-magnetic nanoparticle conjugates. The different combination of complementary DNA-magnetic nanoparticle conjugates gives rise to a distinct magnetic ID barcode that can be readily read with a magnetoresistive scan head.

The examples set forth above are provided to give those of ordinary skill in the art a complete disclosure and description of how to make and use the embodiments of the devices, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Detailed Description, and Examples is hereby incorporated herein by reference. Further, the hard copy of the sequence listing submitted herewith and the corresponding computer readable form are both incorporated herein by reference in their entireties.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains. Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Anderson, N. L. & Anderson, N. G. The human plasma proteome—History, character, and diagnostic prospects. *Molecular & Cellular Proteomics* 1, 845-867 (2002).
2. Fujii, K. et al. Clinical-scale high-throughput human plasma proteome clinical analysis: Lung adenocarcinoma. *Proteomics* 5, 1150-1159 (2005).
3. Lathrop, J. T., Anderson, N. L., Anderson, N. G. & Hammond, D. J. Therapeutic potential of the plasma proteome. *Current Opinion in Molecular Therapeutics* 5, 250-257 (2003).
4. Chen, J. H. et al. Plasma proteome of severe acute respiratory syndrome analyzed by two-dimensional gel electrophoresis and mass spectrometry. *Proceedings of the National Academy of Sciences of the United States of America* 101, 17039-17044 (2004).
5. Hsieh, S. Y., Chen, R. K., Pan, Y. H. & Lee, H. L. Systematical evaluation of the effects of sample collection procedures on low-molecular-weight serum/plasma proteome profiling. *Proteomics* 6, 3189-3198 (2006).
6. Sia, S. K. & Whitesides, G. M. Microfluidic devices fabricated in poly(dimethylsiloxane) for biological studies. *Electrophoresis* 24, 3563-3576 (2003).
7. Whitesides, G. M., Ostuni, E., Takayama, S., Jiang, X. Y. & Ingber, D. E. Soft lithography in biology and biochemistry. *Annual Review of Biomedical Engineering* 3, 335-373 (2001).
8. Quake, S. R. & Scherer, A. From micro- to nanofabrication with soft materials. *Science* 290, 1536-1540 (2000).

9. Huang, B. et al. Counting low-copy number proteins in a single cell. *Science* 315, 81-84 (2007).
10. Ottesen, E. A., Hong, J. W., Quake, S. R. & Leadbetter, J. R. Microfluidic digital PCR enables multigene analysis of individual environmental bacteria. *Science* 314, 1464-1467 (2006).
11. Huang, L. R., Cox, E. C., Austin, R. H. & Sturm, J. C. Continuous particle separation through deterministic lateral displacement. *Science* 304, 987-990 (2004).
12. Chou, C. F. et al. Sorting biomolecules with microdevices. *Electrophoresis* 21, 81-90 (2000).
13. Toner, M. & Irimia, D. Blood-on-a-chip. *Annual Review of Biomedical Engineering* 7, 77-103 (2005).
14. Crowley, T. A. & Pizziconi, V. Isolation of plasma from whole blood using planar microfilters for lab-on-a-chip applications. *Lab on a Chip* 5, 922-929 (2005).
15. Nagrath, S. et al. Isolation of rare circulating tumour cells in cancer patients by microchip technology. *Nature* 450, 1235-U1210 (2007).
16. Yang, S., Undar, A. & Zahn, J. D. A microfluidic device for continuous, real time blood plasma separation. *Lab on a Chip* 6, 871-880 (2006).
17. Svanes, K. & Zweifach, B. W. Variations in small blood vessel hematocrits produced in hypothermic rates by micro-occlusion. *Microvascular Research* 1, 210-220 (1968).
18. Fung, Y. C. Stochastic flow in capilary blood vessels. *Microvasc. Res.* 5, 34-38 (1973).
19. Bailey, R. C., Kwong, G. A., Radu, C. G., Witte, O. N. & Heath, J. R. DNA-encoded antibody libraries: A unified platform for multiplexed cell sorting and detection of genes and proteins. *Journal of the American Chemical Society* 129, 1959-1967 (2007).
20. Boozer, C., Ladd, J., Chen, S. F. & Jiang, S. T. DNA-directed protein immobilization for simultaneous detection of multiple analytes by surface plasmon resonance biosensor. *Analytical Chemistry* 78, 1515-1519 (2006).
21. Niemeyer, C. M. Functional devices from DNA and proteins. *Nano Today* 2, 42-52 (2007).
22. Niemeyer, C. M., Adler, M. & Wacker, R. Lmmuno-PCR: high sensitivity detection of proteins by nucleic acid amplification. *Trends in Biotechnology* 23, 208-216 (2005).
23. Michel, B. et al. Printing meets lithography: Soft approaches to high-resolution patterning. *Chimia* 56, 527-542 (2002).
24. Lange, S. A., Benes, V., Kern, D. P., Horber, J. K. H. & Bernard, A. Microcontact printing of DNA molecules. *Analytical Chemistry* 76, 1641-1647 (2004).
25. Delamarche, E., Bernard, A., Schmid, H., Michel, B. & Biebuyck, H. Patterned delivery of immunoglobulins to surfaces using microfluidic networks. *Science* 276, 779-781 (1997).
26. Bernard, A., Michel, B. & Delamarche, E. Micromosaic immunoassays. *Analytical Chemistry* 73, 8-12 (2001).
27. Pirrung, M. C. How to make a DNA chip. *Angewandte Chemie-International Edition* 41, 1277-+(2002).
28. Coussens, L. M. & Werb, Z. Inflammation and cancer. *Nature* 420, 860-867 (2002).
29. Lin, W. W. & Karin, M. A cytokine-mediated link between innate immunity, inflammation, and cancer. *Journal of Clinical Investigation* 117, 1175-1183 (2007).
30. De Marzo, A. M. et al. Inflammation in prostate carcinogenesis. *Nature Reviews Cancer* 7, 256-269 (2007).
31. Ashton, H. & Telford, R. Smoking and carboxhemoglobin. *Lancet* 2, 857-858 (1973).
32. Schweitzer, B. et al. Multiplexed protein profiling on microarrays by rolling-circle amplification. *Nature Biotechnology* 20, 359-365 (2002).
33. Phillips, T. M. Rapid analysis of inflammatory cytokines in cerebrospinal fluid using chip-based immunoaffinity electrophoresis. *Electrophoresis* 25, 1652-1659 (2004).
34. Lambeck, A. J. A. et al. Serum cytokine profiling as a diagnostic and prognostic tool in ovarian cancer: A potential role for interleukin 7. *Clinical Cancer Research* 13, 2385-2391 (2007).
35. Gorelik, E. et al. Multiplexed immunobead-based cytokine profiling for early detection of ovarian cancer. *Cancer Epidemiology Biomarkers & Prevention* 14, 981-987 (2005).
36. Dehqanzada, Z. A. et al. Assessing serum cytokine profiles in breast cancer patients receiving a HER2/neu vaccine using Luminex (R) technology. *Annals of Surgical Oncology* 12, S47-S48 (2005).
37. Heath, J. R. & Davis, M. E. Nanotechnology and cancer. *Annual Review of Medicine* 59, 405 (2007).
38. Zimmermann, M., Delamarche, E., Wolf, M. & Hunziker, P. Modeling and optimization of high-sensitivity, low-volume microfluidic-based surface immunoassays. *Biomedical Microdevices* 7, 99-110 (2005).

What is claimed is:

1. A method for multiplexed sample analysis, the method comprising:
   providing a device comprising:
      a surface retaining at least four separate lines of capture antibodies arranged parallel to one another and in a serpentine-like pattern over the surface, wherein each line of capture antibodies comprises a specific and different antibody, relative to antibodies of adjacent lines of capture antibodies, configured to bind to a different target molecule;
      and
      a substrate that couples with the surface, the substrate comprising a plurality of open chambers, wherein:
         the coupling of the substrate and the surface is such that a portion of the surface covers and encloses each chamber of the plurality of chambers to form a plurality of respective enclosures resulting in each enclosure of the plurality of enclosures being enclosed on all sides,
         each enclosure of the plurality of enclosures includes a biological sample,
         the biological sample comprises one or more components selected from the group consisting of a biological fluid, a cell, a plurality of cells, a tissue, and a combination thereof,
         the portion of the surface covering each chamber of the plurality of chambers to form each enclosure of the plurality of enclosures includes at least one antibody set comprising a portion of each of the lines of capture antibodies attached to the surface;
   providing reaction conditions that allow for specific interaction between the one or more components of the biological sample and at least one capture antibody from the plurality of lines of capture antibodies, or, between at least one target molecule of the one or more components of the biological sample and the at least one capture antibody, so as to form at least one capture antibody complex;
   providing at least one labeled secondary antibody that specifically binds to the at least one capture antibody complex, wherein:
      the at least one labeled secondary antibody detects a specific interaction between the at least one capture antibody and the one or more components of the biological sample or between at least one target molecule and the at least one capture antibody, providing a detectable signal corresponding to the specific interaction, and
      the detectable signal comprises a signature corresponding to the biological sample; and
   visualizing at least one signature to identify one or more components of the biological sample.

2. The method of claim 1, wherein at least one target molecule is present in at least a portion of the plurality of enclosures.

3. The method of claim 1, wherein at least one target molecule is present in each enclosure of the plurality of enclosures.

4. The method of claim 1, wherein the one or more components of the biological sample includes one or more cell(s) and at least one target molecule is produced by the one or more cell(s).

5. The method of claim 4, wherein at least one target molecule comprises a chemokine, a cytokine, a growth factor, or a transcription factor.

6. The method of claim 1, wherein at least one target molecule comprises a chemokine, a cytokine, a growth factor, or a transcription factor.

7. The method of claim 1, wherein the biological sample includes at least one target molecule and the biological sample is provided in a buffer solution.

8. The method of claim 1, wherein the biological sample includes at least one target molecule and a biological fluid.

9. The method of claim 8, wherein the biological fluid comprises blood, plasma, serum, saliva, joint fluid, cell lysate, or tissue lysate.

10. The method of claim 1, wherein the biological sample includes a component of at least one cell.

11. The method of claim 1, wherein the labeled secondary antibodies comprise fluorescent, gold or silver labels.

12. The method of claim 1, wherein the method further comprises quantifying one or more components of the at least one signature.

13. The method of claim 12, wherein the quantifying step comprises measuring an intensity and/or a density of the labeled secondary antibody.

14. The method of claim 1, wherein the separate lines of capture antibodies comprises between 4 and 50 separate lines of capture antibodies, each of which specifically bind to a different target molecule.

15. The method of claim 1, wherein the at least one signature indicates a health or disease state of a subject.

16. The method of claim 1, wherein the method further comprises analyzing two or more signatures to generate a pattern of expression and/or abundance of one or more components of the biological sample.

* * * * *

SEQUENCE LISTING

```
<160> NUMBER OF SEQ ID NOS: 41

<210> SEQ ID NO 1
<211> LENGTH: 33
<212> TYPE: DNA
<213> ORGANISM: artificial sequence
<220> FEATURE:
<223> OTHER INFORMATION: Synthetic Polynucleotide

<400> SEQUENCE: 1
aaaaaaaaaa aaaatcctgg agctaagtcc gta                              33

<210> SEQ ID NO 2
<211> LENGTH: 30
<212> TYPE: DNA
<213> ORGANISM: artificial sequence
<220> FEATURE:
<223> OTHER INFORMATION: Synthetic Polynucleotide
```

<400> SEQUENCE: 2
aaaaaaaaaa tacggactta gctccaggat                                              30

<210> SEQ ID NO 3
<211> LENGTH: 33
<212> TYPE: DNA
<213> ORGANISM: artificial sequence
<220> FEATURE:
<223> OTHER INFORMATION: Synthetic Polynucleotide

<400> SEQUENCE: 3
aaaaaaaaaa aaagcctcat tgaatcatgc cta                                          33

<210> SEQ ID NO 4
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 4
aaaaaaaaaa taggcatgat tcaatgaggc                                              30

<210> SEQ ID NO 5
<211> LENGTH: 33
<212> TYPE: DNA
<213> ORGANISM: artificial sequence
<220> FEATURE:
<223> OTHER INFORMATION: Synthetic Polynucleotide

<400> SEQUENCE: 5
aaaaaaaaaa aaagcactcg tctactatcg cta                                          33

<210> SEQ ID NO 6
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 6
aaaaaaaaaa tagcgatagt agacgagtgc                                              30

<210> SEQ ID NO 7
<211> LENGTH: 33
<212> TYPE: DNA
<213> ORGANISM: artificial sequence
<220> FEATURE:
<223> OTHER INFORMATION: Synthetic Polynucleotide

<400> SEQUENCE: 7
aaaaaaaaaa aaaatggtcg agatgtcaga gta                                          33

<210> SEQ ID NO 8
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 8
aaaaaaaaaa tactctgaca tctcgaccat                                              30

<210> SEQ ID NO 9

```
<211> LENGTH: 33
<212> TYPE: DNA
<213> ORGANISM: artificial sequence
<220> FEATURE:
<223> OTHER INFORMATION: Synthetic Polynucleotide

<400> SEQUENCE: 9
aaaaaaaaaa aaaatgtgaa gtggcagtat cta                                    33

<210> SEQ ID NO 10
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 10
aaaaaaaaaa tagatactgc cacttcacat                                        30

<210> SEQ ID NO 11
<211> LENGTH: 33
<212> TYPE: DNA
<213> ORGANISM: artificial sequence
<220> FEATURE:
<223> OTHER INFORMATION: Synthetic Polynucleotide

<400> SEQUENCE: 11
aaaaaaaaaa aaaatcaggt aaggttcacg gta                                    33

<210> SEQ ID NO 12
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 12
aaaaaaaaaa taccgtgaac cttacctgat                                        30

<210> SEQ ID NO 13
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 13
aaaaaaaaaa gagtagcctt cccgagcatt                                        30

<210> SEQ ID NO 14
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 14
aaaaaaaaaa aatgctcggg aaggctactc                                        30

<210> SEQ ID NO 15
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 15
```
aaaaaaaaaa attgaccaaa ctgcggtgcg              30

<210> SEQ ID NO 16
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 16
aaaaaaaaaa cgcaccgcag tttggtcaat              30

<210> SEQ ID NO 17
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 17
aaaaaaaaaa tgccctattg ttgcgtcgga              30

<210> SEQ ID NO 18
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 18
aaaaaaaaaa tccgacgcaa caatagggca              30

<210> SEQ ID NO 19
<211> LENGTH: 29
<212> TYPE: DNA
<213> ORGANISM: artificial sequence
<220> FEATURE:
<223> OTHER INFORMATION: Synthetic Polynucleotide

<400> SEQUENCE: 19
aaaaaaaaat cttctagttg tcgagcagg               29

<210> SEQ ID NO 20
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 20
aaaaaaaaaa cctgctcgac aactagaaga              30

<210> SEQ ID NO 21
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 21
aaaaaaaaaa taatctaatt ctggtcgcgg              30

<210> SEQ ID NO 22
<211> LENGTH: 30
<212> TYPE: DNA

<213> ORGANISM: artificial sequence
<220> FEATURE:
<223> OTHER INFORMATION: Synthetic Polynucleotide

<400> SEQUENCE: 22
aaaaaaaaaa ccgcgaccag aattagatta                            30

<210> SEQ ID NO 23
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 23
aaaaaaaaaa gtgattaagt ctgcttcggc                            30

<210> SEQ ID NO 24
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 24
aaaaaaaaaa gccgaagcag acttaatcac                            30

<210> SEQ ID NO 25
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 25
aaaaaaaaaa gtcgaggatt ctgaacctgt                            30

<210> SEQ ID NO 26
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 26
aaaaaaaaaa acaggttcag aatcctcgac                            30

<210> SEQ ID NO 27
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 27
aaaaaaaaaa gtcacagact agccacgaag                            30

<210> SEQ ID NO 28
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 28
aaaaaaaaaa gcgtgtgtgg actctctcta                            30

<210> SEQ ID NO 29
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 29
aaaaaaaaaa tagagagagt ccacacacgc                                   30

<210> SEQ ID NO 30
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 30
aaaaaaaaaa tcttctagtt gtcgagcagg                                   30

<210> SEQ ID NO 31
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 31
aaaaaaaaaa cctgctcgac aactagaaga                                   30

<210> SEQ ID NO 32
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 32
aaaaaaaaaa gatcgtatgg tccgctctca                                   30

<210> SEQ ID NO 33
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 33
aaaaaaaaaa tgagagcgga ccatacgatc                                   30

<210> SEQ ID NO 34
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 34
aaaaaaaaaa gcactaactg gtctgggtca                                   30

<210> SEQ ID NO 35
<211> LENGTH: 30
<212> TYPE: DNA
<213> ORGANISM: artificial sequence
<220> FEATURE:

<223> OTHER INFORMATION: Synthetic Polynucleotide

<400> SEQUENCE: 35
aaaaaaaaaa tgacccagac cagttagtgc                               30

<210> SEQ ID NO 36
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 36
aaaaaaaaaa tgccctattg ttgcgtcgga                               30

<210> SEQ ID NO 37
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 37
aaaaaaaaaa tccgacgcaa caatagggca                               30

<210> SEQ ID NO 38
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 38
aaaaaaaaaa ctctgtgaac tgtcatcggt                               30

<210> SEQ ID NO 39
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 39
aaaaaaaaaa accgatgaca gttcacagag                               30

<210> SEQ ID NO 40
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 40
aaaaaaaaaa gagtagcctt cccgagcatt                               30

<210> SEQ ID NO 41
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 41
aaaaaaaaaa aatgctcggg aaggctactc                               30